(12) United States Patent
Webel et al.

(10) Patent No.: US 9,724,380 B2
(45) Date of Patent: Aug. 8, 2017

(54) METHOD AND COMPOSITIONS FOR SYNCHRONIZING TIME OF INSEMINATION IN GILTS

(71) Applicant: JBS UNITED ANIMAL HEALTH II LLC, Sheridan, IN (US)

(72) Inventors: Stephen Kent Webel, Baylis, IL (US); Mark E. Swanson, Princeton Junction, NJ (US); Robert R. Kraeling, Sheridan, IN (US); Michael E. Johnston, Noblesville, IN (US)

(73) Assignee: JBS UNITED ANIMAL HEALTH II LLC, Sheridian, IN (US)

( * ) Notice: Subject to any disclaimer, the term of this patent is extended or adjusted under 35 U.S.C. 154(b) by 0 days.

(21) Appl. No.: 14/648,182

(22) PCT Filed: Nov. 27, 2013

(86) PCT No.: PCT/US2013/072359
§ 371 (c)(1),
(2) Date: May 28, 2015

(87) PCT Pub. No.: WO2014/085674
PCT Pub. Date: Jun. 5, 2014

(65) Prior Publication Data
US 2015/0306169 A1   Oct. 29, 2015

Related U.S. Application Data

(60) Provisional application No. 61/730,763, filed on Nov. 28, 2012.

(51) Int. Cl.
*A61K 38/09* (2006.01)
*A61P 5/02* (2006.01)
*A61P 15/08* (2006.01)

(52) U.S. Cl.
CPC ........ *A61K 38/09* (2013.01); *A01K 2227/108* (2013.01)

(58) Field of Classification Search
CPC .......................... A01K 2227/108; A61K 38/09
See application file for complete search history.

(56) References Cited

U.S. PATENT DOCUMENTS

| | | | |
|---|---|---|---|
| 3,860,701 A | 1/1975 | Short | |
| 3,991,750 A | 11/1976 | Vickery | |
| 4,005,063 A | 1/1977 | Gendrich et al. | |
| 4,008,209 A | 2/1977 | Fujino et al. | |
| 4,400,316 A | 8/1983 | Katsuragi et al. | |
| 4,732,763 A | 3/1988 | Beck et al. | |
| 4,756,907 A | 7/1988 | Beck et al. | |
| 4,780,451 A | 10/1988 | Donaldson | |
| 4,804,626 A | 2/1989 | Bellet et al. | |
| 4,931,279 A | 6/1990 | Bawa et al. | |
| 4,975,280 A | 12/1990 | Schacht et al. | |
| 5,180,711 A | 1/1993 | Hodgen | |
| 5,236,704 A | 8/1993 | Fujioka et al. | |
| 5,418,228 A | 5/1995 | Bennink | |
| 5,434,136 A | 7/1995 | Mathias | |
| 5,434,146 A | 7/1995 | Labrie et al. | |
| 5,444,167 A | 8/1995 | Pettersson | |
| 5,512,303 A | 4/1996 | Garza Flores et al. | |
| 5,585,370 A | 12/1996 | Casper | |
| 5,589,457 A | 12/1996 | Wiltbank et al. | |
| 5,605,702 A | 2/1997 | Teillaud et al. | |
| 5,633,014 A | 5/1997 | Garza Flores et al. | |
| 5,650,173 A | 7/1997 | Ramstack et al. | |
| 5,686,097 A | 11/1997 | Taskovish et al. | |
| 5,688,506 A | 11/1997 | Grimes et al. | |
| 5,747,058 A | 5/1998 | Tipton et al. | |
| 6,028,057 A | 2/2000 | Burns | |
| 6,051,558 A | 4/2000 | Burns et al. | |
| 6,087,352 A | 7/2000 | Trout | |
| 6,469,139 B1 | 10/2002 | Roitt et al. | |
| 6,503,534 B1 | 1/2003 | Pellet | |
| 6,908,623 B2 | 6/2005 | Deaver et al. | |
| 7,205,281 B2 | 4/2007 | Lauderdale | |
| 7,456,207 B2 | 11/2008 | Bentley et al. | |
| 8,530,419 B2 | 9/2013 | Lauderdale | |
| 8,905,913 B2 | 12/2014 | Webel | |
| 8,927,496 B2 | 1/2015 | Lauderdale | |
| 8,937,044 B2 | 1/2015 | Lauderdale | |
| 9,018,165 B2 | 4/2015 | Lauderdale | |
| 9,351,818 B2 | 5/2016 | Lauderdale | |
| 9,352,011 B2 * | 5/2016 | Webel et al. | .......... A61K 38/09 |

(Continued)

FOREIGN PATENT DOCUMENTS

| | | |
|---|---|---|
| CN | 1913924 | 2/2007 |
| CN | 102596215 | 2/2012 |

(Continued)

OTHER PUBLICATIONS

Methocel Dow. accessed online at http://www.dow.com/dowwolff/en/industrial_solutions/product/methocel.htm on Apr. 28, 2016. p. 1 or 1.*
Martinant-Botte et al. Synchronization of oestrus in gilts with altrenogest: effects on ovulation rate and foetal survival. Animal Reproduction Science, 1995. pp. 267-274.*
Ramakrishnappa et al., "GnRH in non-hypothalamic reproductive Tissue", Anim Reprod Sci 2005; 88:95-113.
Walmer and Huhn, "New aspects of the Management of Reproduction in Pig", Reprod Dom Anim. 1996;31:477-482.
Barb et al., "Evaluation of the saber delivery system for the controlled release of deslorelin: Effect of dose in estrogen primed ovarectomized gilts", Proceed. Int'l Symp. Control. Rel. Bioacr. Mater., 26: 1170-1171 (1999).
Betteridge and Raeside, "Observation of the ovary by peritoneal cannulation in pigs", Res. Vet. Sci. 3:390-398 (1962).
Britt et al., "Induction of fertile estnis in perpuberal gilts by treatment with a combination of pregnant mare's serum gonadotrophin and human chorionic gonadotropin", J. Anim. Sci., 67:1148-53 (1989).

(Continued)

*Primary Examiner* — Marcela M Cordero Garcia
(74) *Attorney, Agent, or Firm* — Barnes & Thornburg LLP

(57) ABSTRACT

Methods and compositions for synchronizing the time of insemination in gilts are provided. More particularly, methods and compositions for synchronizing the time of insemination in gilts using a gonadotropin-releasing hormone and a hormone for synchronizing estrus are provided.

22 Claims, 4 Drawing Sheets

(56) References Cited

U.S. PATENT DOCUMENTS

| | | |
|---|---|---|
| 2004/0266697 A1 | 12/2004 | McSweeney |
| 2005/0130894 A1 | 6/2005 | Lauderdale |
| 2006/0264372 A1 | 11/2006 | Webel |
| 2007/0031500 A1 | 2/2007 | Cherif-Cheikh |
| 2007/0173450 A1 | 7/2007 | Lauderdale |
| 2007/0197435 A1 | 8/2007 | Webel |
| 2009/0036384 A1 | 2/2009 | Bell |
| 2010/0312137 A1 | 12/2010 | Gilmour |
| 2012/0046519 A1 | 2/2012 | Webel |
| 2013/0041210 A1 | 2/2013 | Lauderdale |
| 2013/0085321 A1 | 4/2013 | Lauderdale |
| 2013/0085322 A1 | 4/2013 | Lauderdale |
| 2014/0155327 A1 | 6/2014 | Lauderdale |
| 2015/0057225 A1 | 2/2015 | Webel |
| 2015/0087587 A1 | 3/2015 | Lauderdale |
| 2016/0375090 A1 | 12/2016 | Webel |
| 2017/0035834 A1 | 2/2017 | Swanson |

FOREIGN PATENT DOCUMENTS

| | | | |
|---|---|---|---|
| GB | 2 166 951 | 5/1986 | |
| SU | 573159 | 9/1977 | |
| WO | WO 97/32572 | 9/1997 | |
| WO | WO 97/37642 | 10/1997 | |
| WO | WO 97/45113 | 12/1997 | |
| WO | WO 98/53837 | 12/1998 | |
| WO | WO 99/42110 | 8/1999 | |
| WO | WO 00/78335 | 12/2000 | |
| WO | 03006049 | 1/2003 | |
| WO | WO 2005/035717 | 4/2005 | |
| WO | 2008018796 | 2/2008 | |
| WO | WO2010124220 | * 4/2010 | ............ A61K 38/00 |
| WO | WO 2010/124220 | 10/2010 | |
| WO | 2013119633 | 8/2013 | |

OTHER PUBLICATIONS

Brussow et al., "Control of ovulation with a GnRH analog in gilts and sows", Theriogenology, 46:925-934 (1996).
Burns and Douglas, "Effects of daily administration of estradiol-17 (β on follicular growth, ovulation, and plasma hormones in mares", Biology of Reproduction, 24:1026-1031 (1981).
Burns et al., "Evaluation of biodegradable microspheres for the controlled release of progesterone and estradiol in an ovulation control program for cycling mares", J. Equine Vet. Sci. 13(9):521-24 (1993).
Cook et al., "Effects of the exogenous estradiol treatment in cyclic mares following PGF induced luteal regression", Proceeding of the 13$^{th}$ Equine Nutrition & Physiology Symposium, Abstract 126, 1993.
De Rensis et al., "Fertility of sows following artificial insemination at a gonadotrophin-induced estrus coincident with weaning", Animal Reproduction Science, 76:245-250 (2003).
Donbrow, ed., "Microcapsules and Nanoparticles in Medicine and Pharmacy", (CRC Press, Boca Raton 1992) (Table of Contents only).
Du Mesnil et al., "Reproductive physiology and artificial insemination in pigs", Vet Rec., 87:562-568 (1970).
Flowers and Alhusen, "Reproductive performance and estimates of labor requirements associates with combinations of artificial insemination and natural service in swine", J. Animal Science, 70:615-621 (1992).
Geisert et al., "Length of pseudopregnancy and pattern of uterine release as influenced by time and duration of estrogen administration in the pig", J. Reprod. Fert., 79:163-72 (1987).
Jackson and Hutchinson, "Slow release formulations of prostaglandin and luteolysis in the pig", Veterinary Record, 106:33-34 (1980).
Martinat-Botte et al., "Control of pig reproduction in a breeding programme", J. Reprod. Fert. Suppl., 33:211-228 (1985).
Niswender et al., "Radioimmunoassay of serum levels of lutenizing hormone throughtout the estrous cycle in pigs", Endocrinology, 87:576-580 (1970).
Peters et al., "Effect of gonadotrophin-releasing hormone on the fertility of sows kept outdoors", Vet. Record, 147:649-652 (2000).
Polge et al., "Synchronisation of ovulation and artificial insemination in pigs", Veterinary Record, 83, 136-142 (1968).
Prokofeva, "Composition for oestrus cycle control in sows-continaing hydroxyl-progesterone caproste, oestradiol valerate, oil, and benzoate to improve heat synchronization", Derwent Publications, Limited SU-549118 (1977).
Pusateri et al., "Maternal Recognition of Pregnancy in Swine.I. Minimal Requirement for Exogenous Estradiol-17B to Induce Either Short or Long Pseudopregnancy in Cycling Gilts", Biol. Reproduction, 55:582-89 (1996).
Sechin et al., "Effect of equine chorionic gonadatropin on weaning to first service interval and litter size of female swine", Theriogenology, 51:1175-1182 (1999).
Sheffield et al., "Effect of estradiol and relaxin on collagen and non-collagen protein sythesis by mammary fibroblasts", Life Sci., 35 (22): 2199-2203 (1984).
Soede et al., "In Synchronized pigs, the duration of ovulation is not affected by insemination and is not a determinant for early embryonic diversity", Theriogenology, 39:1043-1053 (1993).
Stevenson et al., "Role of the Ovary in Controlling Luteinizing Hormone, Follice Stimulating Hormone, and Prolactin Secretion During and After Lactation in Pigs", Biol. Reproduction, 24:341-53 (1981).
Stork, M.G., "Seasonal reproduction inefficiency in large pig breeding units in Britain", Veterinary Record, 104:49-52 (1979).
Tilton et al., "Evaluation of Response to Hormonal Therapy in Prepubertal Gilts of Different Genetic Lines", J. Anim Sci., 73:3062-68 (1995).
Ulberg et al., "The effects of progesterone upon ovarian function in gilts", J. Animal Sci., 10:665-671 (1951).
Van Der Meulen et al., "Effects of intra-uterine oestradiol-17 beta administration of inter-oestrous interval in the pig", Animal Reproduction Science, 24:305-313 (1991).
Gordon, L.R., Controlled Reporduction in Pigs CAB International: Wallingford, Oxon, UK; New York, ISBN:0851991165 (table of contents only) (1997).
Asdell, Patterns of Mammalian Reproduction, 2nd ed., Cornell University Press, Ithaca, USA, pp. 670 (1964).
Dziuk, Reproduction in the pig. In: Cupps, P. T. (ed.) Reproduction in Domestic Animals, 4th ed., Academic Press, New York, pp. 471-489 (1991).
Day, et al., Effect of intravaginal progesterone (P4) insert-porcine (IPI-P) on synchronization of estrus, ovulation rate, fertility and P4 blood levels in gilts. In: Control of Reproduction in the Female Pig. 30th Annual Meeting, American Association of Swine Practitioners, Workshop #6, St. Louis, Mo. Feb. 27, 1999, pp. 23-39 (ref. unavailable).
Estill et al., "Estrus sychronization of gilts using steriod-containing implants and a PGF2α analogue," Society for Teriogenology Proceedings for Annual Meeting (1997).
Webel, S.K. and B.N. Day. 1982. The control of ovulation. In: D.J.A. Cole and G.R. Foxcroft (Eds.) Control of Pig Reproduction. Butterworths, London. pp. 197-210.
Nissen et al., "The influence of time of insemination relative to time of ovulation on farrowing frequency and litter size in sow, as investigated by ultrasonography," Theriogenology, 47: 1571-1582 (1997).
Waberski et al., "Effect of time of insemination relative to ovulation on fertility with liquid and frozen boar semen," Theriogenology, 42: 831-840 (1994).
Soede et al., "Timing of insemination relative to ovulation in pigs: Effects on sex ratio of offspring," Theriogenology, 53: 1003-1011 (2000).
Knox et al., "Controlling Estrus and Ovulation", National Hog Farmer, Nov. 15, 2003, 18-20.
Knox et al., "Intravaginal administration of GnRH agonist gel advances time of ovulation and facilitates timed AI in weaned sows," 34th Annual AASV Meeting: Orlando, Florida, USA (2003), available at www.aasv.org.

(56) References Cited

OTHER PUBLICATIONS

Busch et al., "Investigations of Estrus Synchronization in swine with the Gestagen Altrenogest (Regumale)", Vet. Med. Monthly, 47:307-316 (1992).
Fleury et al., "Regulation of estrus and ovulation in cyclic mares with progesterone and estradiol biodegradable microspheres", J. Equine Vet. Sci., 13(9):525-28 (1993).
Knox et al., "Administration of P.G. 600 to Sows at Weaning and the Time of Ovulation as Determined by Transrectal Ultrasound", J. Animal. Sci., 79:796-802 (2001).
LaForest et al., "Effect of Topical Application of Estradiol-17B and PGE2 on PGE-binding sites in the Porcine Endometrium", Reprod. Nutr. Dev., 32(2): 93-104 (1992).
Dixon et al., "The effects of estradiol cypionate on expression of estrus in a follicular synchronization program," J. Animal Science, 82 (supp. 1): 369, W225 (2004).
Kirkwood, "Pharmacological intervention in swine reproduction", Swine Health Prod., 7(1): 29-35 (1999).
Langendijk, "Synchronization of ovulation with GnRH or hCG in weaned sows, without pre-treatment with eCG", J. Reprod. Fertil., Abstract Series No. 26, Abstract #93, p. 35 (2000).
Gerrits et al., "Effect of synchronization of estrus on fertility in gilts", J. Animal Sci., 21:1022 (1962).
Guthrie et al., "Treatment of pregnant gilts with a prostaglandin analogue, Cloprostenol, to control estrus and fertility", J. Reprod. Fert., 52:271-73 (1978).
Guthrie et al., "Changes in plasma estrogen, luteinizing hormone, follicle-stimulating hormone and 13, 14-dihydro-15-ketoprostaglandin F2 during blockade of luteolysis in pigs after human chorionic gonadotropin treatment", J. Anim. Sci., 57:993-100 (1983).
Hansel et al., "Corpora lutea of the large domestic animals", Biology of Reproduction, 8:222-245 (1973).
Hodson et al., "Effect of gonadotropin dose and postpartum status on induced ovulation and pregnancy in lactating sows", J. Animimal Sci., 52(4):688-695 (1981).
Howard, et al., "Prostaglandin F2 causes regression of an hCG induced corpus luteum before Day 5 of its lifespan in cattle," J. Reprod. Fert., 90:245-53 (1990).
Hunter and Polge, "Maturation of follicular oocytes in the pig after injection of human chorionic gonadotrophin," J. Repro. Fert. 12: 525-531 (1966).
Hunter, "Physiological factors influencing ovulation, fertilization, early embryonic development and establishment of pregnancy in pigs," Brit. Vet. J., 133: 461-470 (1977).
Hurtgen and Leman, "Seasonal influence on the fertility of sows and gilts," J Amer Vet. Med. Ass., 177: 631-635 (1980).
Betteridge and Raeside, "Investigation of Cervical Mucus as an indicator of ovarian activity in pigs," J. Reprod. Fertility., 3:410-421 (1962).
Coffey, "Manipulation of the Estrous Cycle in Swine," available t.ca.uky.edulagc/pubs/asc/asc15asc152.htm, Nov. 10, 2007.
Broaddus, "Insemination of diary cows without heat detection," Journal of Diary Science vol. 79, Suppl. 1, 1996.
Webel, "Estrus Control in Horses with a Progestin," #564, p. 385 (1975).
Webel, "Response of the Cycling Gilt to TRH," #566, p. 385 (1975).
Soede et al., "Effects of time of insemination relative to ovulation, as determined by ultrasonography, on fertilization rate and accessory sperm count in sows," Journal for Reproduction and Fertility (1995) 104, 99-106.
Larson et al., "Synchronization of estrus in replacement beef heifers using GnRH, prostaglandin F2-alpha (PG), and progesterone (CIDR): a multi-location study," J. Animal Science, 82 (supp. 1): 369, W223 (2004).
Webel and Rippel, et al., "Ovulation in the pig with releasing hormones," J Animal Science, 41:385, Abs tract No. 565 (1975).
Yavas, at al., "Postpartum acyclicity in suckled beef cows: A review", Theriogenology, 54(1):25255 (2000).

Yavas, at al., "Induction of ovulation in postpartum suckled beef cows: A review", Theriogenology, 54(1):1-23 (2000).
Roski et al., "Ovulatory and reproductive characteristics of sows treated with an intravaginal GnRh agonist gel", J. Anim. Sci., vol. 82 Supplement 1, Jul. 28, 2004.
Filicori, Drugs 1994; 48: 41-58.
Crowley, Annu Rev. Med. 1994; 45: 391-405.
Boime and Ben-Menahem, Recent Progr. Horm Res. 1999; 54: 271-288.
Garcia-Campayo and Boime, Trends Endocrinol. Metabl 2001; 12: 72-77.
PG600, MSD Animal Health, product sheet, health://www.msd-animal-health.ph/products/131_118602/productsdetails_131_118778, printed May 25, 2012.
Handelsman et al, "Pharmacokinetics of Gonadotropin-Releasing Hormone and Its Analogs", Endocrine Review, vol. 7, No. 1, 95-105 (1986).
Conn, "Gonadotropin-Releasing Hormone and Its Analogues", The New England Journal of Medicine, vol. 324, 93-103 (1991).
S. K. Webel, "Ovulation Control in the Pig", Easter School in Agriculture Science, $26^{th}$, 1978.
Kim & Park, Journal of Controlled Release, 2002; 80: 69-77.
Bos et al., "Hydrogels for the Controlled Release of Pharmaceutical Proteins", Pharmaceutical Technology, 79:110-120 (2001).
Goodman & Gilman's The Pharmacological Basis of Therapeutics, Ninth Ed., 1996; From Benet et al., Chapter 1, Pharmacokinetics'; p. 8.
Gupta et al., DDT, 2002; 7: 569-579.
Wenzel et al., "Pluronic® F127 gel formulations of Deslorelin and GnRH reduce drug degradation and sustain drug release and effect in cattle", J Controlled Release, 85: 51-59 (2002).
Baer et al., "The Effects of Intravaginal Applied GnRH-agonist on the Time of Ovulation and Subsequent Reproductive Performance of Weaned Multiparous Sows", Reprod Dom Anim 39, 293-297 (2004).
Belstra et al., "Factors affecting temporal relationships between estrus and ovulation in commercial sow farms", Animal Reproduction Science 84 (2004) 377-394.
Brussow et al., "Lutenizing hormone release after administration of the gonadotropin-releasing hormone agonist Fertilan (goserelin) for synchronization of ovulation of pigs", J. Anim. Sci. 2007, 85:129-137.
H. D. Guthrie, "Induction of Ovulation and Fertility in Prepuberal Gilts", J Anim Sci 1977, 45:1360-1367.
Guthrie et al., "Attempts to Induce Conception in Lactating Sows", J Anim Sci 1978, 47:1145-1151.
Baker et al., "Induction of Ovulation in Pigs with Gonadotrophin Releasing Hormone", J Anim Sci Dec. 1973, vol. 37, No. 6, 1376-1379. (summary only).
Langendijk et al., "Role of myometrial activity in sperm transport through the genital tract and in fertilization in sows", Reproduction (2002) 123, 683-690.
Tek et al., "The effect of Gonadotrophins on estrus induction and fertility in prepubertal gilts", Revue Med. Vet., 2003, 154, 2, 133-138.
Taibl et al., "Effect of Synchronizing Ovulation in Weaned Sows Using Ovugel with Single Fixed Time AI on Pregnancy Rate and Litter Size", VIII International Conference on Pig Reproduction, Jun. 1-3, 2009.
Madan et al., "IN Situ Forming Polymeric Drug Delivery Systems", Indian J. Ph arm Sci., 71: 242-26 (2009).
Berger et al., Mol Cell Endocrinol. 1996; 125: 33-43.
Gooneratne et al., Can. J. Anim. Sci., 1989, 69:123-129.
Taibl, J.N., et al. "Induction of ovulation using a GnRH agonist for use with a fixed time AI in weaned sows", Theriogenology, 2008, 70(8), 1400.
Schneider, F., et al. "Gonadotropin-releasing hormone (GnRII) and its natural analogues: A review", Theriogenology, 2006, 66(4), 691-709.
European Search Report from European Patent Application No. 10767846.8 issued Apr. 11, 2013.

(56) References Cited

OTHER PUBLICATIONS

Archived website downloaded Jan. 13, 2013 at web.archive.org/web/20040831011300/http://nationalhogfarmer.com/mag/farming (Aug. 31, 2004).
PCT International Search Report from PCT/US2013/072359 completed Feb. 28, 2014.
Guthrie, HD, et al. "Changes in concentrations of follicular inhibin alpha and beta a subunit messenger ribonucleic acids and inhibin immunoactivity during preovulatory maturation in the pig." Biol Reprod. Dec. 1992;47(6):1018-25.
Brussow et al., "Studies on fixed-time ovulation induction in the pig," *Soc Reprod Fertil Suppl.*, 2009; 66:187-95.
Martinat-Botte et al., "Induction and synchronization of ovulations of nulliparous and multiparous sows with an injection of gonadotropin-releasing hormone agonist (Receptal)," *Theriogenelogy*, 2010; 73: 332-342.
Kraeling et al., "Failure of the orally active progestin, Regu-mate, to overcome confinement-induced delayed puberty in gilts," *Theriogenelogy*, 1982; 17:183-187.
Szabo et al., "Effect of Treatment with Prolan or with a GnRH Superactive Analog on thwe Sexual Function of Sows After Weaning", Acta Veterinaria Hungarica 39 (1-2), pp. 3-11 (1991).
Swarts et al., "Synchronization of estrus and ovulation by an Altrenogest/Buserelin treatment in gilts results in good fertility and prolificacy following a single fixed time AI," $22^{nd}$ International Pig Veterinary Society Congrees, Reproduction, IPVS 2012, Korea, RO-020, p. 90.
Driancourt et al., "Induction of an LH surge and ovulation by buserelin (as Receptal) allows breeding of weaned sows with a single fixed-time insemination," Theriogenology, 2013, 80: 391-9.
Jouyban et al., "Review of Pharmaceutical Applications of N-Methyl-2-Pyrrolidone," J. Pharm Pharmaceut Sci, 2010, 13(4): 524-535.
Redmer et al., "Ovarian activity and hormonal patterns in gilts fed allyl trenbolone" Journal of Animal Science, vol. 53, No. 4, 1981.

\* cited by examiner

METHOD AND COMPOSITIONS FOR SYNCHRONIZING TIME OF INSEMINATION IN GILTS

CROSS REFERENCE TO RELATED APPLICATIONS

This application is a U.S. national stage application under 35 U.S.C. §371(b) of International Application No. PCT/US2013/072359 filed Nov. 27, 2013, and claims priority under 35 U.S.C. §119(e) to U.S. Provisional Application Ser. No. 61/730,763, filed Nov. 28, 2012, the disclosures of which are incorporated herein by reference.

FIELD OF THE INVENTION

The invention relates to methods and compositions for synchronizing the time of insemination in gilts. More particularly, the invention relates to methods and compositions for synchronizing the time of insemination in gilts using a gonadotropin-releasing hormone and a hormone for synchronizing estrus.

BACKGROUND OF THE INVENTION

Gonadotropin-releasing hormone is a peptide of 10 amino acids and is also known as luteinizing-hormone releasing hormone (LHRH). Gonadotropin-releasing hormone is produced in the hypothalamus, and is responsible for the release of follicle-stimulating hormone and luteinizing hormone from the pituitary gland. Gonadotropin-releasing hormone is released from neurons in the hypothalmus, and plays a role in the complex regulation of follicle-stimulating hormone and luteinizing hormone release. Follicle-stimulating hormone and luteinizing hormone, in combination, regulate the functioning of the gonads to produce testosterone in the testes and progesterone and estrogen in the ovaries, and regulate the production and maturation of gametes. For example, follicle-stimulating hormone stimulates the growth and recruitment of immature ovarian follicles in the ovary, and luteinizing hormone triggers ovulation.

There are differences in gonadotropin-releasing hormone secretion between females and males. In males, gonadotropin-releasing hormone is secreted in pulses at a constant frequency, but in females the frequency of the pulses varies during the estrus cycle and there is a large surge of gonadotropin-releasing hormone just before ovulation. Gonadotropin-releasing hormone secretion is pulsatile in all vertebrates, and is necessary for correct reproductive function. Thus, gonadotropin-releasing hormone controls a complex process of follicular growth, ovulation, and corpus luteum maintenance in the female, and spermatogenesis in the male.

Gonadotropin-releasing hormone has been isolated and characterized as a decapeptide. Synthetic forms of gonadotropin-releasing hormone are available and modifications of the decapeptide structure of gonadotropin-releasing hormone have led to multiple gonadotropin-releasing hormone analogs that either stimulate or suppress the release of the gonadotropins, such as luteinizing hormone and follicle-stimulating hormone.

It is important to commercial swine production to maximize reproductive efficiency to make swine production more profitable. Labor intensive methods are presently required, such as daily checks for estrus, to increase the probability of success with artificial insemination in swine, such as gilts and sows. Devoting time, manual labor, and materials costs to daily checks for estrus detection is currently necessary because it is difficult to predict the time of estrus (i.e., to predict the best time for insemination) without using methods requiring daily estrus detection. Accordingly, simpler, less labor intensive, but equally effective methods are needed to optimize the success of insemination of swine, including gilts and sows, to reduce the labor costs, costs of materials, and to increase the profitability of swine production.

High sow replacement rates place significant pressures on replacement gilt management to maintain consistent swine production flow. The variation associated with the ovulatory process in gilts is one of the critically important issues related to optimizing reproductive performance. Therefore, effective treatments to more precisely control ovulation are needed so that all gilts in a group may be inseminated without the need for a daily regimen for monitoring estrus.

SUMMARY OF THE INVENTION

Applicants have discovered effective treatments to more precisely control ovulation in gilts so that the gilts in a group may be inseminated without the need for a daily regimen for monitoring estrus. The methods and compositions described herein are much simpler than daily estrus detection, but are unexpectedly as effective as a daily regimen for monitoring estrus, in optimizing reproductive performance of gilts, including, but not limited to, litter size and total piglets born alive.

In one embodiment, a method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration of the hormone for synchronizing estrus, and 3) inseminating the gilt without estrus detection only one time on the sixth day after the last daily administration of the hormone for synchronizing estrus.

In another embodiment, a method for synchronizing time of insemination in a gilt is provided. The method comprises the steps of 1) administering to the gilt a hormone for synchronizing estrus, administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus, 2) monitoring estrus on the fifth day after the last daily administration of the hormone for synchronizing estrus, and then inseminating the gilt on the fifth day after the last daily administration of the hormone for synchronizing estrus, if the gilt is in estrus, wherein the gilt is inseminated in combination with administration of the gonadotropin-releasing hormone, and 3) if the gilt is in estrus or is not in estrus on the fifth day after the last daily administration of the hormone for synchronizing estrus, inseminating the gilt on the sixth day after the last daily administration of the hormone for synchronizing estrus wherein estrus is not monitored on the sixth day after the last daily administration of the hormone for synchronizing estrus.

In yet another embodiment, a method for synchronizing time of insemination in a gilt is provided. The method comprises the steps of 1) administering to the gilt a hormone for synchronizing estrus, administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus, 2) inseminating the gilt a first time at about 2 to about 7 hours after administration of the gonadotropin-releasing hormone, and 3) inseminating the gilt a second time on the sixth day after the last daily administration of the hormone for synchronizing estrus wherein the first and second inseminations are done without monitoring estrus.

The embodiments described in the clauses below, or any combinations thereof, are also contemplated for use in the invention.

1. A method for synchronizing time of insemination in a gilt, the method comprising the steps of:
administering to the gilt a hormone for synchronizing estrus;
administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration of the hormone for synchronizing estrus; and
inseminating the gilt, without monitoring estrus, only one time on the sixth day after the last daily administration of the hormone for synchronizing estrus.

2. The method according to clause 1 wherein the gonadotropin releasing hormone has the formula

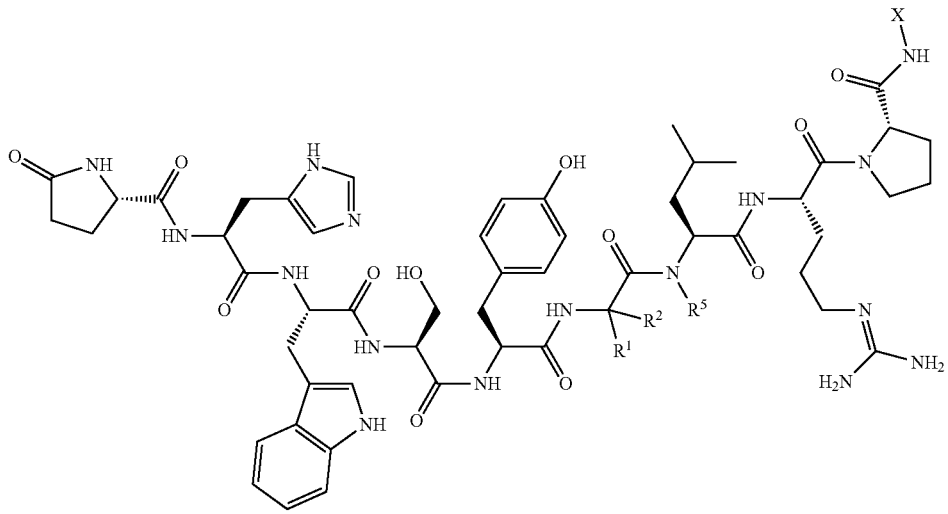

or a solvate, a hydrate, or a pharmaceutically acceptable salt thereof wherein
$R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
$R^5$ is hydrogen or alkyl; and
X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

3. The method according to clause 2 wherein the gonadotropin-releasing hormone is selected from the group consisting of compounds of the formula of claim 2 wherein
a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
b) $R^1$ is hydrogen, $R^2$ is hydrogen, X is $CH_2(CO)NH_2$; and $R^5$ is hydrogen;
c) $R^1$ is 1H-1-benzyl-imidazol-4-yl-methyl, $R^2$ is hydrogen, X is ethyl; and $R^5$ is hydrogen;
d) $R^1$ is 2-methylpropyl, $R^2$ is hydrogen, X is ethyl; and $R^5$ is hydrogen;
e) $R^1$ is 2-naphthlymethyl, $R^2$ is hydrogen, X is $CH_2(CO)NH_2$; and $R^5$ is hydrogen;
f) $R^1$ is t-butoxymethyl, $R^2$ is hydrogen, X is ethyl; $R^5$ is hydrogen; and the configuration of the carbon to which $R^1$ is attached is R;
g) $R^1$ is benzyl, $R^2$ is hydrogen, X is $CH_2(CO)NH_2$; $R^5$ is hydrogen; and the configuration of the carbon to which $R^1$ is attached is R;
h) $R^1$ is t-butoxymethyl, $R^2$ is hydrogen, X is $HN(CO)NH_2$; and $R^5$ is hydrogen;
i) $R^1$ is 1H-indol-3-yl-methyl, $R^2$ is hydrogen, X is ethyl; and $R^5$ is hydrogen;
j) $R^1$ is methyl, $R^2$ is hydrogen, X is hydrogen; $R^5$ is hydrogen; and the configuration of the carbon to which $R^1$ is attached is R;
k) $R^1$ is 1H-indol-3-yl-methyl, $R^2$ is hydrogen, X is ethyl; $R^5$ is methyl; and the configuration of the carbon to which $R^1$ is attached is R;
l) $R^1$ is methyl, $R^2$ is hydrogen, X is $CH_2(CO)NH_2$; $R^5$ is hydrogen; and the configuration of the carbon to which $R^1$ is attached is R;
m) $R^1$ is 4-aminobutyl, $R^2$ is hydrogen, X is $HN(CO)NH_2$; $R^5$ is hydrogen; and the configuration of the carbon to which $R^1$ is attached is R;
n) $R^1$ is methyl, $R^2$ is methyl, X is $HN(CO)NH_2$; and $R^5$ is hydrogen; and
o) $R^1$ is ethyl, $R^2$ is hydrogen, X is hydrogen; $R^5$ is hydrogen; and the configuration of the carbon to which $R^1$ is attached is R.

4. The method according to any one of clauses 1 to 3 wherein the insemination is an artificial insemination.

5. The method according to any one of clauses 1 to 4 wherein the gonadotropin-releasing hormone is administered in an effective amount and the effective amount of the gonadotropin-releasing hormone is about 1 µg to about 500 µg.

6. The method according to any one of clauses 1 to 5 wherein the gonadotropin-releasing hormone is administered in an effective amount and the effective amount of the gonadotropin-releasing hormone is about 100 µg to about 300 µg.

7. The method according to any one of clauses 1 to 6 wherein the gonadotropin-releasing hormone is administered in an effective amount and the effective amount of the gonadotropin-releasing hormone is about 200 µg.

8. The method according to any one of clauses 1 to 7 wherein the gonadotropin-releasing hormone is at a concentration of about 50 µg/mL to about 200 µg/mL.

9. The method according to any one of clauses 1 to 8 wherein the gonadotropin-releasing hormone is at a concentration of about 50 µg/mL to about 150 µg/mL.

10. The method of any one of clauses 1 to 9 wherein the gonadotropin-releasing hormone is at a concentration of about 100 µg/mL.

11. The method according to any one of clauses 1 to 10 wherein the dose of the gonadotropin-releasing hormone is administered using a method selected from the group consisting of use of a deposition catheter, manual administration, and injection.

12. The method of clause 11 wherein the gonadotropin-releasing hormone is administered using a deposition catheter.

13. The method of clause 11 wherein the gonadotropin-releasing hormone is administered by injection.

14. The method according to any one of clauses 1 to 13 wherein the hormone is in acetate form.

15. The method according to any one of clauses 1 to 12 or 14 wherein the hormone is administered in a composition comprising a gel.

16. The method according to clause 15 wherein the gel is a polysaccharide selected from the group consisting of celluloses, dextrans, and alginates.

17. The method according to clause 16 wherein the polysaccharide is a cellulose and the cellulose is methylcellulose.

18. The method of clause 17 wherein the gel comprises about 0.5 weight % to about 4.0 weight % of methylcellulose.

19. The method of clause 18 wherein the gel is 1.2% methylcellulose.

20. The method according to clause 15 wherein the gel has a viscosity of about 200 cP to about 5,000 cP.

21. The method of any one of clauses 1 to 12 or 14 to 20 wherein the gonadotropin-releasing hormone is administered intravaginally.

22. The method of clause 21 wherein the gonadotropin-releasing hormone is administered into the anterior vagina.

23. The method according to any one of clauses 1 to 22 wherein the method results in fertility of the gilt.

24. The method according to any one of clauses 2 to 23 wherein in the formula X is $H_2CC(O)NH_2$, $R_1$ is hydrogen, and $R_2$ is

25. The method of any one of clauses 1 to 24 wherein the gonadotropin-releasing hormone is triptorelin.

26. The method of any one of clauses 1 to 25 wherein the hormone that synchronizes estrus is altrenogest.

27. The method according to any one of clauses 1 to 12 or 14 to 26 wherein the gonadotropin-releasing hormone is in a composition and the composition further comprises a stabilizer wherein the stabilizer is L-methionine.

28. The method of any one of clauses 1 to 12 or 14 to 27 wherein the gonadotropin-releasing hormone is in a composition with a pH of about 5 to about 6.

29. The method of any one of clauses 1 to 12 or 14 to 28 wherein the gonadotropin-releasing hormone is in a composition further comprising a preservative.

30. The method of clause 29 wherein the preservative is selected from the group consisting of methylparaben and propylparaben.

31. The method of any one of clauses 1 to 12 or 14 to 30 wherein the gonadotropin-releasing hormone is in a composition and the composition comprises methylparaben, propylparaben, sodium chloride, sodium citrate, L-methionine, citric acid, triptorelin, and methylcellulose.

32. The method of clause 31 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount that provides a viscosity of about 250 cP to about 400 cP.

33. The method according to any one of clauses 1 to 14 or 21 to 26 wherein the gonadotropin-releasing hormone is in an excipient selected from the group consisting of buffered saline, a liquid alcohol, a glycol, a glucose solution, an ester, an amide, and sterile water.

34. The method of clause 33 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

35. The method of any one of clauses 1 to 34 further comprising the step of exposing the gilt to a boar.

36. The method of any one of clauses 1 to 35 wherein the hormone for synchronizing estrus is administered by feeding.

37. The method of any one of clauses 1 to 36 wherein the gonadotropin-releasing hormone is administered about 118 to about 124 hours after the last daily administration of the hormone for synchronizing estrus.

38. The method of any one of clauses 1 to 36 wherein the gonadotropin-releasing hormone is administered about 124 to about 132 hours after the last daily administration of the hormone for synchronizing estrus.

39. The method of any one of clauses 1 to 38 wherein the gilt is inseminated about 24 to about 28 hours after administration of the gonadotropin-releasing hormone.

40. A method for synchronizing time of insemination in a gilt, the method comprising the steps of:
administering to the gilt a hormone for synchronizing estrus;
administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus;
monitoring estrus on the fifth day after the last daily administration of the hormone for synchronizing estrus, and then inseminating the gilt on the fifth day after the last daily administration of the hormone for synchronizing estrus, if the gilt is in estrus, wherein the gilt is inseminated in combination with administration of the gonadotropin-releasing hormone; and
if the gilt is in estrus or is not in estrus on the fifth day after the last daily administration of the hormone for synchronizing estrus, inseminating the gilt on the sixth day after the last daily administration of the hormone for synchronizing estrus wherein estrus is not monitored on the sixth day after the last daily administration of the hormone for synchronizing estrus.

41. The method according to clause 40 wherein the gonadotropin-releasing hormone has the formula 42. The method according to clause 41 wherein the gonadotropin-releasing hormone is selected from the group consisting of compounds of the formula of claim 41 wherein
a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
b) $R^1$ is hydrogen, $R^2$ is hydrogen, X is $CH_2(CO)NH_2$; and $R^5$ is hydrogen;
c) $R^1$ is 1H-1-benzyl-imidazol-4-yl-methyl, $R^2$ is hydrogen, X is ethyl; and $R^5$ is hydrogen;
d) $R^1$ is 2-methylpropyl, $R^2$ is hydrogen, X is ethyl; and $R^5$ is hydrogen;
e) $R^1$ is 2-naphthlymethyl, $R^2$ is hydrogen, X is $CH_2(CO)NH_2$; and $R^5$ is hydrogen;
f) $R^1$ is t-butoxymethyl, $R^2$ is hydrogen, X is ethyl; $R^5$ is hydrogen; and the configuration of the carbon to which $R^1$ is attached is R;
g) $R^1$ is benzyl, $R^2$ is hydrogen, X is $CH_2(CO)NH_2$; $R^5$ is hydrogen; and the configuration of the carbon to which $R^1$ is attached is R;
h) $R^1$ is t-butoxymethyl, $R^2$ is hydrogen, X is $HN(CO)NH_2$; and $R^5$ is hydrogen;
i) $R^1$ is 1H-indol-3-yl-methyl, $R^2$ is hydrogen, X is ethyl; and $R^5$ is hydrogen;
j) $R^1$ is methyl, $R^2$ is hydrogen, X is hydrogen; $R^5$ is hydrogen; and the configuration of the carbon to which $R^1$ is attached is R;
k) $R^1$ is 1H-indol-3-yl-methyl, $R^2$ is hydrogen, X is ethyl; $R^5$ is methyl; and the configuration of the carbon to which $R^1$ is attached is R;

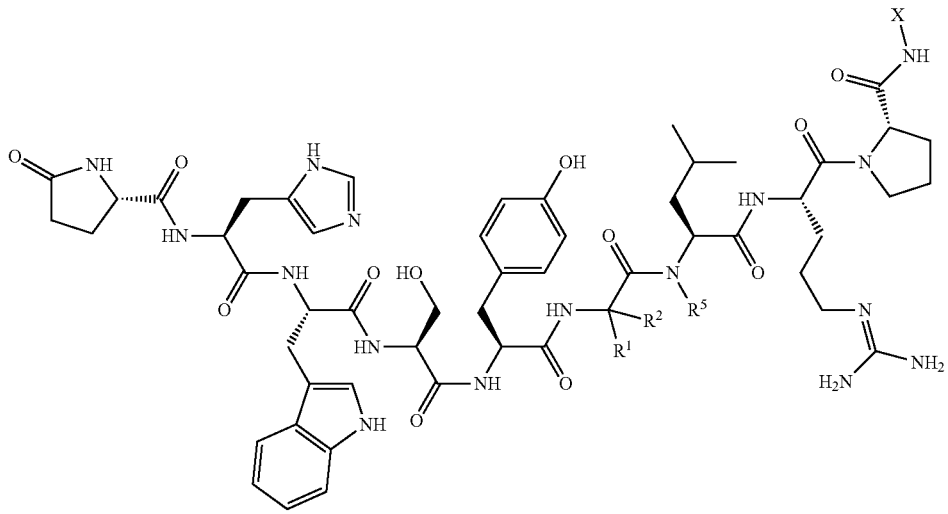

or a solvate, a hydrate, or a pharmaceutically acceptable salt thereof wherein
$R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
$R^5$ is hydrogen or alkyl; and
X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

l) $R^1$ is methyl, $R^2$ is hydrogen, X is $CH_2(CO)NH_2$; $R^5$ is hydrogen; and the configuration of the carbon to which $R^1$ is attached is R;
m) $R^1$ is 4-aminobutyl, $R^2$ is hydrogen, X is $HN(CO)NH_2$; $R^5$ is hydrogen; and the configuration of the carbon to which $R^1$ is attached is R;
n) $R^1$ is methyl, $R^2$ is methyl, X is $HN(CO)NH_2$; and $R^5$ is hydrogen; and
o) $R^1$ is ethyl, $R^2$ is hydrogen, X is hydrogen; $R^5$ is hydrogen; and the configuration of the carbon to which $R^1$ is attached is R.

43. The method according to any one of clauses 40 to 42 wherein the insemination is an artificial insemination.

44. The method according to any one of clauses 40 to 43 wherein the gonadotropin-releasing hormone is administered in an effective amount and the effective amount of the gonadotropin-releasing hormone is about 1 μg to about 500 μg.

45. The method according to any one of clauses 40 to 44 wherein the gonadotropin-releasing hormone is administered in an effective amount and the effective amount of the gonadotropin-releasing hormone is about 100 μg to about 300 μg.

46. The method according to any one of clauses 40 to 45 wherein the gonadotropin-releasing hormone is administered in an effective amount and the effective amount of the gonadotropin-releasing hormone is about 200 μg.

47. The method according to any one of clauses 40 to 46 wherein the gonadotropin-releasing hormone is at a concentration of about 50 μg/mL to about 200 μg/mL.

48. The method according to any one of clauses 40 to 47 wherein the gonadotropin-releasing hormone is at a concentration of about 50 μg/mL to about 150 μg/mL.

49. The method of any one of clauses 40 to 48 wherein the gonadotropin-releasing hormone is at a concentration of about 100 μg/mL.

50. The method according to any one of clauses 40 to 49 wherein the dose of the gonadotropin-releasing hormone is administered using a method selected from the group consisting of use of a deposition catheter, manual administration, and injection.

51. The method of clause 50 wherein the gonadotropin-releasing hormone is administered using a deposition catheter.

52. The method of clause 50 wherein the gonadotropin-releasing hormone is administered by injection.

53. The method according to any one of clauses 40 to 52 wherein the gonadotropin-releasing hormone in acetate form.

54. The method according to any one of clauses 40 to 51 or 53 wherein the gonadotropin-releasing hormone is administered in a composition comprising a gel.

55. The method according to clause 54 wherein the gel is a polysaccharide selected from the group consisting of celluloses, dextrans, and alginates.

56. The method according to clause 55 wherein the polysaccharide is a cellulose and the cellulose is methylcellulose.

57. The method of clause 56 wherein the gel comprises about 0.5 weight % to about 4.0 weight % of methylcellulose.

58. The method of clause 57 wherein the gel is 1.2% methylcellulose.

59. The method according to clause 54 wherein the gel has a viscosity of about 200 cP to about 5,000 cP.

60. The method of any one of clauses 40 to 51 or 53 to 59 wherein the gonadotropin-releasing hormone is administered intravaginally.

61. The method of clause 60 wherein the gonadotropin-releasing hormone is administered into the anterior vagina.

62. The method of any one of clauses 40 to 61 wherein the method results in fertility of the gilt.

63. The method according to any one of clauses 41 to 62 wherein in the formula X is $H_2CC(O)NH_2$, $R_1$ is hydrogen, and $R_2$ is

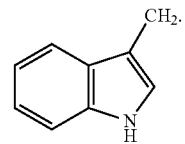

64. The method of any one of clauses 40 to 63 wherein the gonadotropin-releasing hormone is triptorelin.

65. The method of any one of clauses 40 to 64 wherein the hormone that synchronizes estrus is altrenogest.

66. The method according to any one of clauses 40 to 51 or 53 to 65 wherein the gonadotropin-releasing hormone is in a composition and the composition further comprises a stabilizer wherein the stabilizer is L-methionine.

67. The method of any one of clauses 40 to 51 or 53 to 66 wherein the gonadotropin-releasing hormone is in a composition with a pH of about 5 to about 6.

68. The method of any one of clauses 40 to 51 or 53 to 67 wherein the gonadotropin-releasing hormone is in a composition further comprising a preservative.

69. The method of clause 68 wherein the preservative is selected from the group consisting of methylparaben and propylparaben.

70. The method of any one of clauses 40 to 51 or 53 to 69 wherein the gonadotropin-releasing hormone is in a composition and the composition comprises methylparaben, propylparaben, sodium chloride, sodium citrate, L-methionine, citric acid, triptorelin, and methylcellulose.

71. The method of clause 70 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount that provides a viscosity of about 250 cP to about 400 cP.

72. The method according to any one of clauses 40 to 53 or 60 to 65 wherein the gonadotropin-releasing hormone is in an excipient selected from the group consisting of buffered saline, a liquid alcohol, a glycol, a glucose solution, an ester, an amide, and sterile water.

73. The method of clause 72 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

74. The method of any one of clauses 40 to 73 further comprising the step of exposing the gilt to a boar.

75. The method of any one of clauses 40 to 74 wherein the hormone for synchronizing estrus is administered by feeding.

76. The method of any one of clauses 40 to 75 wherein the gonadotropin-releasing hormone is administered about 118 to about 124 hours after the last daily administration of the hormone for synchronizing estrus.

77. The method of any one of clauses 40 to 75 wherein the gonadotropin-releasing hormone is administered about 124 to about 132 hours after the last daily administration of the hormone for synchronizing estrus.

78. The method of any one of clauses 40 to 77 wherein the gilt is inseminated the first time within about two hours of the time of administration of the gonadotropin-releasing hormone, if the gilt is in estrus on the fifth day after the last daily administration of the hormone for synchronizing estrus.

79. The method of any one of clauses 40 to 78 wherein the gilt is inseminated on the sixth day about 24 to about 28 hours after administration of the gonadotropin-releasing hormone.

80. A method for synchronizing time of insemination in a gilt, the method comprising the steps of:
administering to the gilt a hormone for synchronizing estrus;
administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus;
inseminating the gilt a first time at about 2 to about 7 hours after administration of the gonadotropin-releasing hormone; and
inseminating the gilt a second time on the sixth day after the last daily administration of the hormone for synchronizing estrus wherein the first and second inseminations are done without monitoring estrus.

81. The method according to clause 80 wherein the gonadotropin-releasing hormone has the formula 82. The method according to clause 81 wherein the gonadotropin-releasing hormone is selected from the group consisting of compounds of the formula of claim 81 wherein
a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
b) $R^1$ is hydrogen, $R^2$ is hydrogen, X is $CH_2(CO)NH_2$; and $R^5$ is hydrogen;
c) $R^1$ is 1H-1-benzyl-imidazol-4-yl-methyl, $R^2$ is hydrogen, X is ethyl; and $R^5$ is hydrogen;
d) $R^1$ is 2-methylpropyl, $R^2$ is hydrogen, X is ethyl; and $R^5$ is hydrogen;
e) $R^1$ is 2-naphthlymethyl, $R^2$ is hydrogen, X is $CH_2(CO)NH_2$; and $R^5$ is hydrogen;
f) $R^1$ is t-butoxymethyl, $R^2$ is hydrogen, X is ethyl; $R^5$ is hydrogen; and the configuration of the carbon to which $R^1$ is attached is R;
g) $R^1$ is benzyl, $R^2$ is hydrogen, X is $CH_2(CO)NH_2$; $R^5$ is hydrogen; and the configuration of the carbon to which $R^1$ is attached is R;
h) $R^1$ is t-butoxymethyl, $R^2$ is hydrogen, X is $HN(CO)NH_2$; and $R^5$ is hydrogen;
i) $R^1$ is 1H-indol-3-yl-methyl, $R^2$ is hydrogen, X is ethyl; and $R^5$ is hydrogen;
j) $R^1$ is methyl, $R^2$ is hydrogen, X is hydrogen; $R^5$ is hydrogen; and the configuration of the carbon to which $R^1$ is attached is R;
k) $R^1$ is 1H-indol-3-yl-methyl, $R^2$ is hydrogen, X is ethyl; $R^5$ is methyl; and the configuration of the carbon to which $R^1$ is attached is R;

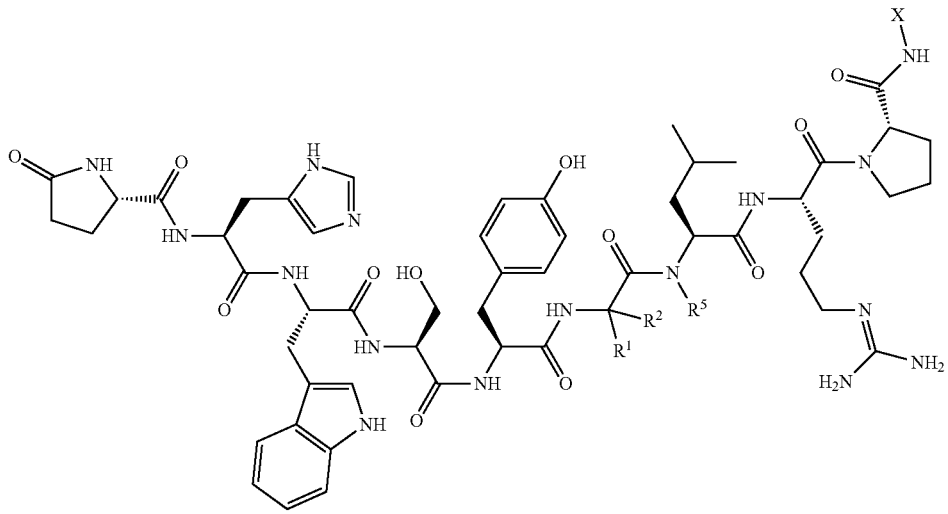

or a solvate, a hydrate, or a pharmaceutically acceptable salt thereof wherein
$R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
$R^5$ is hydrogen or alkyl; and
X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

l) $R^1$ is methyl, $R^2$ is hydrogen, X is $CH_2(CO)NH_2$; $R^5$ is hydrogen; and the configuration of the carbon to which $R^1$ is attached is R;
m) $R^1$ is 4-aminobutyl, $R^2$ is hydrogen, X is $HN(CO)NH_2$; $R^5$ is hydrogen; and the configuration of the carbon to which $R^1$ is attached is R;
n) $R^1$ is methyl, $R^2$ is methyl, X is $HN(CO)NH_2$; and $R^5$ is hydrogen; and
o) $R^1$ is ethyl, $R^2$ is hydrogen, X is hydrogen; $R^5$ is hydrogen; and the configuration of the carbon to which $R^1$ is attached is R.

83. The method according to any one of clause 80 to 82 wherein the insemination is an artificial insemination.

84. The method according to any one of clauses 80 to 83 wherein the gonadotropin-releasing hormone is administered in an effective amount and the effective amount of the gonadotropin-releasing hormone is about 1 µg to about 500 µg.

85. The method according to any one of clauses 80 to 84 wherein the gonadotropin-releasing hormone is administered in an effective amount and the effective amount of the gonadotropin-releasing hormone is about 100 µg to about 300 µg.

86. The method according to any one of clauses 80 to 85 wherein the gonadotropin-releasing hormone is administered in an effective amount and the effective amount of the gonadotropin-releasing hormone is about 200 µg.

87. The method according to any one of clauses 80 to 86 wherein the gonadotropin-releasing hormone is at a concentration of about 50 µg/mL to about 200 µg/mL.

88. The method according to any one of clauses 80 to 87 wherein the gonadotropin-releasing hormone is at a concentration of about 50 µg/mL to about 150 µg/mL.

89. The method of any one of clauses 80 to 88 wherein the gonadotropin-releasing hormone is at a concentration of about 100 µg/mL.

90. The method according to any one of clauses 80 to 89 wherein the dose of the gonadotropin-releasing hormone is administered using a method selected from the group consisting of use of a deposition catheter, manual administration, and injection.

91. The method of clause 90 wherein the gonadotropin-releasing hormone is administered using a deposition catheter.

92. The method of clause 90 wherein the gonadotropin-releasing hormone is administered by injection.

93. The method according to any one of clauses 80 to 92 wherein the gonadotropin-releasing hormone in acetate form.

94. The method according to any one of clauses 80 to 91 or 93 wherein the gonadotropin-releasing hormone is administered in a composition comprising a gel.

95. The method according to clause 94 wherein the gel is a polysaccharide selected from the group consisting of celluloses, dextrans, and alginates.

96. The method according to clause 95 wherein the polysaccharide is a cellulose and the cellulose is methylcellulose.

97. The method of clause 96 wherein the gel comprises about 0.5 weight % to about 4.0 weight % of methylcellulose.

98. The method of clause 97 wherein the gel is 1.2% methylcellulose.

99. The method according to clause 94 wherein the gel has a viscosity of about 200 cP to about 5,000 cP.

100. The method of any one of clauses 90 to 91 or 93 to 99 wherein the gonadotropin-releasing hormone is administered intravaginally.

101. The method of clause 100 wherein the gonadotropin-releasing hormone is administered into the anterior vagina.

102. The method according to any one of clauses 80 to 101 wherein the method results in fertility of the gilt.

103. The method according to any one of clauses 81 to 102 wherein in the formula X is $H_2CC(O)NH_2$, $R_1$ is hydrogen, and $R_2$ is

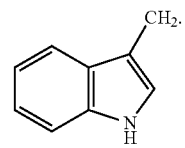

104. The method of any one of clauses 80 to 103 wherein the gonadotropin-releasing hormone is triptorelin.

105. The method of any one of clauses 80 to 104 wherein the hormone that synchronizes estrus is altrenogest.

106. The method according to any one of clauses 80 to 91 or 93 to 105 wherein the gonadotropin-releasing hormone is in a composition and the composition further comprises a stabilizer wherein the stabilizer is L-methionine.

107. The method of any one of clauses 80 to 91 or 93 to 106 wherein the gonadotropin-releasing hormone is in a composition with a pH of about 5 to about 6.

108. The method of any one of clauses 80 to 91 or 93 to 107 wherein the gonadotropin-releasing hormone is in a composition further comprising a preservative.

109. The method of clause 108 wherein the preservative is selected from the group consisting of methylparaben and propylparaben.

110. The method of any one of clauses 80 to 91 or 93 to 109 wherein the gonadotropin-releasing hormone is in a composition and the composition comprises methylparaben, propylparaben, sodium chloride, sodium citrate, L-methionine, citric acid, triptorelin, and methylcellulose.

111. The method of clause 110 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount that provides a viscosity of about 250 cP to about 400 cP.

112. The method according to any one of clauses 80 to 93 or 100 to 105 wherein the gonadotropin-releasing hormone is in an excipient selected from the group consisting of buffered saline, a liquid alcohol, a glycol, a glucose solution, an ester, an amide, and sterile water.

113. The method of clause 112 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

114. The method of any one of clauses 80 to 113 further comprising the step of exposing the gilt to a boar.

115. The method of any one of clauses 80 to 114 wherein the hormone for synchronizing estrus is administered by feeding.

116. The method of any one of clauses 80 to 115 wherein the gonadotropin-releasing hormone is administered about 118 to about 124 hours after the last daily administration of the hormone for synchronizing estrus.

117. The method of any one of clauses 80 to 115 wherein the gonadotropin-releasing hormone is administered about 124 to about 132 hours after the last daily administration of the hormone for synchronizing estrus.

118. The method of any one of clauses 80 to 117 wherein the gilt is inseminated the first time about 2 to about 4 hours after administration of the gonadotropin-releasing hormone.

119. The method of any one of clauses 80 to 118 wherein the gilt is inseminated the second time about 24 to about 28 hours after administration of the gonadotropin-releasing hormone.

120. The method of any one of clauses 80 to 119 wherein the gilt is inseminated the first time about 2 to about 3 hours after administration of the gonadotropin-releasing hormone.

121. The method of any one of clauses 1 to 120 wherein the litter size of the gilt is similar to the litter size of control gilts inseminated based on daily estrus detection.

122. The method of any one of clauses 1 to 121 wherein the total piglets born alive to the gilt is similar to the total piglets born alive to control gilts inseminated based on daily estrus detection.

DETAILED DESCRIPTION OF THE ILLUSTRATIVE EMBODIMENTS

Figure 1:
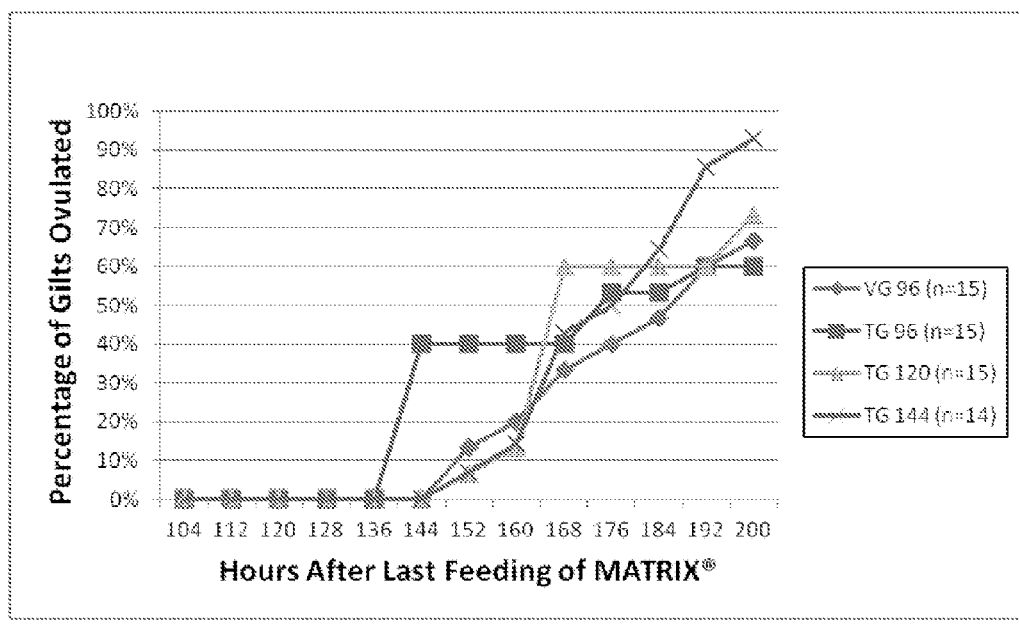
FIG. 1 shows the cumulative percentage of gilts, which ovulated after administration of vehicle gel at 96 hours (VG 96) or triptorelin gel containing 200 μg triptorelin at 96 hours (TG 96), 120 hours (TG 120) or 144 hours (TG 144) after last MATRIX® feeding in replicate 1.

Applicants have discovered the methods, kits, and compositions described herein that provide for effective treatments to more precisely control ovulation in gilts so that the gilts in a group can be inseminated without the need for a daily regimen for monitoring estrus. The methods and compositions described herein are much simpler than daily estrus detection, but are unexpectedly as effective in optimizing reproductive performance as a daily regimen for monitoring estrus, including, but not limited to, litter size and total piglets born alive.

In one embodiment, a method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration of the hormone for synchronizing estrus, and 3) inseminating the gilt, without monitoring estrus, only one time on the sixth day after the last daily administration of the hormone for synchronizing estrus.

In another embodiment, a method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus, 3) monitoring estrus on the fifth day after the last daily administration of the hormone for synchronizing estrus, and then inseminating the gilt on the fifth day after the last daily administration of the hormone for synchronizing estrus, if the gilt is in estrus, wherein the gilt is inseminated in combination with administration of the gonadotropin-releasing hormone, and 4) if the gilt is in estrus or is not in estrus on the fifth day after the last daily administration of the hormone for synchronizing estrus, inseminating the gilt on the sixth day after the last daily administration of the hormone for synchronizing estrus wherein estrus is not monitored on the sixth day after the last daily administration of the hormone for synchronizing estrus.

In yet another embodiment, a method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus, 3) inseminating the gilt a first time at about 2 to about 7 hours after administration of the gonadotropin-releasing hormone, and 4) inseminating the gilt a second time on the sixth day after the last daily administration of the hormone for synchronizing estrus wherein the first and second inseminations are done without monitoring estrus. For each of the above-described embodiments any of the features, or combinations thereof, described in the Detailed Description of the Illustrative Embodiments section of this patent application are applicable.

For example, the embodiments described in the clauses below, or any combinations thereof, are contemplated for use in the methods and compositions of the invention.

1. A method for synchronizing time of insemination in a gilt, the method comprising the steps of:

administering to the gilt a hormone for synchronizing estrus;

administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration of the hormone for synchronizing estrus; and inseminating the gilt, without monitoring estrus, only one time on the sixth day after the last daily administration of the hormone for synchronizing estrus.

2. The method according to clause 1 wherein the gonadotropin releasing hormone has the formula

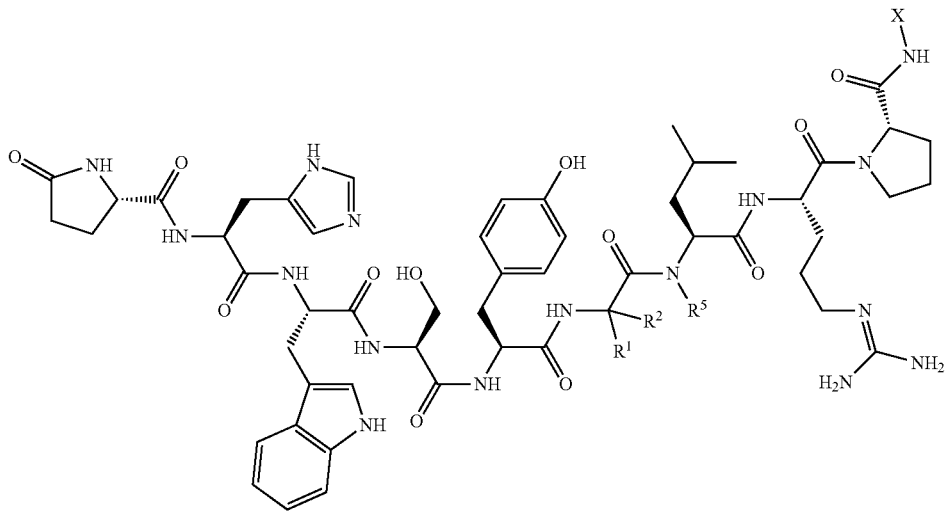

or a solvate, a hydrate, or a pharmaceutically acceptable salt thereof wherein

R¹ and R² are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or R¹ and R² and the attached carbon form a carbocycle or heterocycle;

R⁵ is hydrogen or alkyl; and

X is hydrogen, or X is selected from the group consisting of alkyl, cycloalkyl, heteroalkyl, optionally substituted alkylene-carboxamide, and HNC(O)NR³R⁴, where R³ and R⁴ are in each instance independently selected from the group consisting of hydrogen, alkyl, heteroalkyl and haloalkyl.

3. The method according to clause 2 wherein the gonadotropin-releasing hormone is selected from the group consisting of compounds of the formula of claim 2 wherein
   a) R¹ is 1H-indol-3-yl-methyl, R² is hydrogen, X is CH₂(CO)NH₂; R⁵ is hydrogen; and the configuration of the carbon to which R¹ is attached is R;
   b) R¹ is hydrogen, R² is hydrogen, X is CH₂(CO)NH₂; and R⁵ is hydrogen;
   c) R¹ is 1H-1-benzyl-imidazol-4-yl-methyl, R² is hydrogen, X is ethyl; and R⁵ is hydrogen;
   d) R¹ is 2-methylpropyl, R² is hydrogen, X is ethyl; and R⁵ is hydrogen;
   e) R¹ is 2-naphthlymethyl, R² is hydrogen, X is CH₂(CO)NH₂; and R⁵ is hydrogen;
   f) R¹ is t-butoxymethyl, R² is hydrogen, X is ethyl; R⁵ is hydrogen; and the configuration of the carbon to which R¹ is attached is R;
   g) R¹ is benzyl, R² is hydrogen, X is CH₂(CO)NH₂; R⁵ is hydrogen; and the configuration of the carbon to which R¹ is attached is R;
   h) R¹ is t-butoxymethyl, R² is hydrogen, X is HN(CO)NH₂; and R⁵ is hydrogen;
   i) R¹ is 1H-indol-3-yl-methyl, R² is hydrogen, X is ethyl; and R⁵ is hydrogen;
   j) R¹ is methyl, R² is hydrogen, X is hydrogen; R⁵ is hydrogen; and the configuration of the carbon to which R¹ is attached is R;
   k) R¹ is 1H-indol-3-yl-methyl, R² is hydrogen, X is ethyl; R⁵ is methyl; and the configuration of the carbon to which R¹ is attached is R;
   l) R¹ is methyl, R² is hydrogen, X is CH₂(CO)NH₂; R⁵ is hydrogen; and the configuration of the carbon to which R¹ is attached is R;
   m) R¹ is 4-aminobutyl, R² is hydrogen, X is HN(CO)NH₂; R⁵ is hydrogen; and the configuration of the carbon to which R¹ is attached is R;
   n) R¹ is methyl, R² is methyl, X is HN(CO)NH₂; and R⁵ is hydrogen; and
   o) R¹ is ethyl, R² is hydrogen, X is hydrogen; R⁵ is hydrogen; and the configuration of the carbon to which R¹ is attached is R.

4. The method according to any one of clauses 1 to 3 wherein the insemination is an artificial insemination.

5. The method according to any one of clauses 1 to 4 wherein the gonadotropin-releasing hormone is administered in an effective amount and the effective amount of the gonadotropin-releasing hormone is about 1 µg to about 500 µg.

6. The method according to any one of clauses 1 to 5 wherein the gonadotropin-releasing hormone is administered in an effective amount and the effective amount of the gonadotropin-releasing hormone is about 100 µg to about 300 µg.

7. The method according to any one of clauses 1 to 6 wherein the gonadotropin-releasing hormone is administered in an effective amount and the effective amount of the gonadotropin-releasing hormone is about 200 µg.

8. The method according to any one of clauses 1 to 7 wherein the gonadotropin-releasing hormone is at a concentration of about 50 µg/mL to about 200 µg/mL.

9. The method according to any one of clauses 1 to 8 wherein the gonadotropin-releasing hormone is at a concentration of about 50 µg/mL to about 150 µg/mL.

10. The method of any one of clauses 1 to 9 wherein the gonadotropin-releasing hormone is at a concentration of about 100 µg/mL.

11. The method according to any one of clauses 1 to 10 wherein the dose of the gonadotropin-releasing hormone is administered using a method selected from the group consisting of use of a deposition catheter, manual administration, and injection.

12. The method of clause 11 wherein the gonadotropin-releasing hormone is administered using a deposition catheter.

13. The method of clause 11 wherein the gonadotropin-releasing hormone is administered by injection.

14. The method according to any one of clauses 1 to 13 wherein the hormone is in acetate form.

15. The method according to any one of clauses 1 to 12 or 14 wherein the hormone is administered in a composition comprising a gel.

16. The method according to clause 15 wherein the gel is a polysaccharide selected from the group consisting of celluloses, dextrans, and alginates.

17. The method according to clause 16 wherein the polysaccharide is a cellulose and the cellulose is methylcellulose.

18. The method of clause 17 wherein the gel comprises about 0.5 weight % to about 4.0 weight % of methylcellulose.

19. The method of clause 18 wherein the gel is 1.2% methylcellulose.

20. The method according to clause 15 wherein the gel has a viscosity of about 200 cP to about 5,000 cP.

21. The method of any one of clauses 1 to 12 or 14 to 20 wherein the gonadotropin-releasing hormone is administered intravaginally.

22. The method of clause 21 wherein the gonadotropin-releasing hormone is administered into the anterior vagina.

23. The method according to any one of clauses 1 to 22 wherein the method results in fertility of the gilt.

24. The method according to any one of clauses 2 to 23 wherein in the formula X is $H_2CC(O)NH_2$, $R_1$ is hydrogen, and $R_2$ is

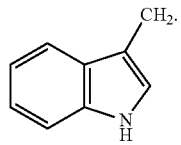

25. The method of any one of clauses 1 to 24 wherein the gonadotropin-releasing hormone is triptorelin.

26. The method of any one of clauses 1 to 25 wherein the hormone that synchronizes estrus is altrenogest.

27. The method according to any one of clauses 1 to 12 or 14 to 26 wherein the gonadotropin-releasing hormone is in a composition and the composition further comprises a stabilizer wherein the stabilizer is L-methionine.

28. The method of any one of clauses 1 to 12 or 14 to 27 wherein the gonadotropin-releasing hormone is in a composition with a pH of about 5 to about 6.

29. The method of any one of clauses 1 to 12 or 14 to 28 wherein the gonadotropin-releasing hormone is in a composition further comprising a preservative.

30. The method of clause 29 wherein the preservative is selected from the group consisting of methylparaben and propylparaben.

31. The method of any one of clauses 1 to 12 or 14 to 30 wherein the gonadotropin-releasing hormone is in a composition and the composition comprises methylparaben, propylparaben, sodium chloride, sodium citrate, L-methionine, citric acid, triptorelin, and methylcellulose.

32. The method of clause 31 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount that provides a viscosity of about 250 cP to about 400 cP.

33. The method according to any one of clauses 1 to 14 or 21 to 26 wherein the gonadotropin-releasing hormone is in an excipient selected from the group consisting of buffered saline, a liquid alcohol, a glycol, a glucose solution, an ester, an amide, and sterile water.

34. The method of clause 33 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

35. The method of any one of clauses 1 to 34 further comprising the step of exposing the gilt to a boar.

36. The method of any one of clauses 1 to 35 wherein the hormone for synchronizing estrus is administered by feeding.

37. The method of any one of clauses 1 to 36 wherein the gonadotropin-releasing hormone is administered about 118 to about 124 hours after the last daily administration of the hormone for synchronizing estrus.

38. The method of any one of clauses 1 to 36 wherein the gonadotropin-releasing hormone is administered about 124 to about 132 hours after the last daily administration of the hormone for synchronizing estrus.

39. The method of any one of clauses 1 to 38 wherein the gilt is inseminated about 24 to about 28 hours after administration of the gonadotropin-releasing hormone.

40. A method for synchronizing time of insemination in a gilt, the method comprising the steps of:

administering to the gilt a hormone for synchronizing estrus;

administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus;

monitoring estrus on the fifth day after the last daily administration of the hormone for synchronizing estrus, and then inseminating the gilt on the fifth day after the last daily administration of the hormone for synchronizing estrus, if the gilt is in estrus, wherein the gilt is inseminated in combination with administration of the gonadotropin-releasing hormone; and if the gilt is in estrus or is not in estrus on the fifth day after the last daily administration of the hormone for synchronizing estrus, inseminating the gilt on the sixth day after the last daily administration of the hormone for synchronizing estrus wherein estrus is not monitored on the sixth day after the last daily administration of the hormone for synchronizing estrus.

41. The method according to clause 40 wherein the gonadotropin-releasing hormone has the formula

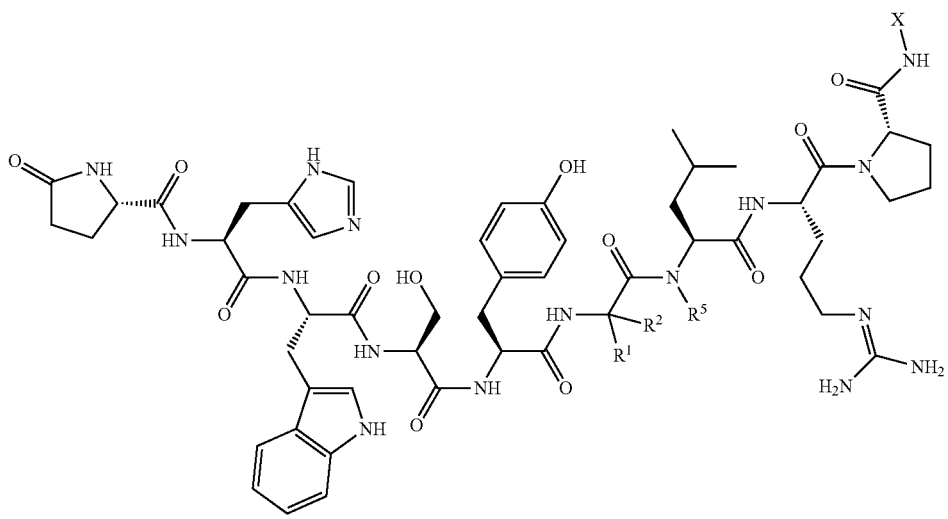

or a solvate, a hydrate, or a pharmaceutically acceptable salt thereof wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;

$R^5$ is hydrogen or alkyl; and

X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

42. The method according to clause 41 wherein the gonadotropin-releasing hormone is selected from the group consisting of compounds of the formula of claim 41 wherein
  a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
  b) $R^1$ is hydrogen, $R^2$ is hydrogen, X is $CH_2(CO)NH_2$; and $R^5$ is hydrogen;
  c) $R^1$ is 1H-1-benzyl-imidazol-4-yl-methyl, $R^2$ is hydrogen, X is ethyl; and $R^5$ is hydrogen;
  d) $R^1$ is 2-methylpropyl, $R^2$ is hydrogen, X is ethyl; and $R^5$ is hydrogen;
  e) $R^1$ is 2-naphthlymethyl, $R^2$ is hydrogen, X is $CH_2(CO)NH_2$; and $R^5$ is hydrogen;
  f) $R^1$ is t-butoxymethyl, $R^2$ is hydrogen, X is ethyl; $R^5$ is hydrogen; and the configuration of the carbon to which $R^1$ is attached is R;
  g) $R^1$ is benzyl, $R^2$ is hydrogen, X is $CH_2(CO)NH_2$; $R^5$ is hydrogen; and the configuration of the carbon to which $R^1$ is attached is R;
  h) $R^1$ is t-butoxymethyl, $R^2$ is hydrogen, X is $HN(CO)NH_2$; and $R^5$ is hydrogen;
  i) $R^1$ is 1H-indol-3-yl-methyl, $R^2$ is hydrogen, X is ethyl; and $R^5$ is hydrogen;
  j) $R^1$ is methyl, $R^2$ is hydrogen, X is hydrogen; $R^5$ is hydrogen; and the configuration of the carbon to which $R^1$ is attached is R;
  k) $R^1$ is 1H-indol-3-yl-methyl, $R^2$ is hydrogen, X is ethyl; $R^5$ is methyl; and the configuration of the carbon to which $R^1$ is attached is R;
  l) $R^1$ is methyl, $R^2$ is hydrogen, X is $CH_2(CO)NH_2$; $R^5$ is hydrogen; and the configuration of the carbon to which $R^1$ is attached is R;
  m) $R^1$ is 4-aminobutyl, $R^2$ is hydrogen, X is $HN(CO)NH_2$; $R^5$ is hydrogen; and the configuration of the carbon to which $R^1$ is attached is R;
  n) $R^1$ is methyl, $R^2$ is methyl, X is $HN(CO)NH_2$; and $R^5$ is hydrogen; and
  o) $R^1$ is ethyl, $R^2$ is hydrogen, X is hydrogen; $R^5$ is hydrogen; and the configuration of the carbon to which $R^1$ is attached is R.

43. The method according to any one of clauses 40 to 42 wherein the insemination is an artificial insemination.

44. The method according to any one of clauses 40 to 43 wherein the gonadotropin-releasing hormone is administered in an effective amount and the effective amount of the gonadotropin-releasing hormone is about 1 μg to about 500 μg.

45. The method according to any one of clauses 40 to 44 wherein the gonadotropin-releasing hormone is administered in an effective amount and the effective amount of the gonadotropin-releasing hormone is about 100 μg to about 300 μg.

46. The method according to any one of clauses 40 to 45 wherein the gonadotropin-releasing hormone is administered in an effective amount and the effective amount of the gonadotropin-releasing hormone is about 200 μg.

47. The method according to any one of clauses 40 to 46 wherein the gonadotropin-releasing hormone is at a concentration of about 50 μg/mL to about 200 μg/mL.

48. The method according to any one of clauses 40 to 47 wherein the gonadotropin-releasing hormone is at a concentration of about 50 μg/mL to about 150 μg/mL.

49. The method of any one of clauses 40 to 48 wherein the gonadotropin-releasing hormone is at a concentration of about 100 μg/mL.

50. The method according to any one of clauses 40 to 49 wherein the dose of the gonadotropin-releasing hormone is administered using a method selected from the group consisting of use of a deposition catheter, manual administration, and injection.

51. The method of clause 50 wherein the gonadotropin-releasing hormone is administered using a deposition catheter.

52. The method of clause 50 wherein the gonadotropin-releasing hormone is administered by injection.

53. The method according to any one of clauses 40 to 52 wherein the gonadotropin-releasing hormone in acetate form.

54. The method according to any one of clauses 40 to 51 or 53 wherein the gonadotropin-releasing hormone is administered in a composition comprising a gel.

55. The method according to clause 54 wherein the gel is a polysaccharide selected from the group consisting of celluloses, dextrans, and alginates.

56. The method according to clause 55 wherein the polysaccharide is a cellulose and the cellulose is methylcellulose.

57. The method of clause 56 wherein the gel comprises about 0.5 weight % to about 4.0 weight % of methylcellulose.

58. The method of clause 57 wherein the gel is 1.2% methylcellulose.

59. The method according to clause 54 wherein the gel has a viscosity of about 200 cP to about 5,000 cP.

60. The method of any one of clauses 40 to 51 or 53 to 59 wherein the gonadotropin-releasing hormone is administered intravaginally.

61. The method of clause 60 wherein the gonadotropin-releasing hormone is administered into the anterior vagina.

62. The method according to any one of clauses 40 to 61 wherein the method results in fertility of the gilt.

63. The method according to any one of clauses 41 to 62 wherein in the formula X is $H_2CC(O)NH_2$, $R_1$ is hydrogen, and $R_2$ is

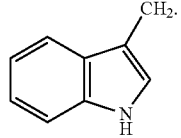

64. The method of any one of clauses 40 to 63 wherein the gonadotropin-releasing hormone is triptorelin.

65. The method of any one of clauses 40 to 64 wherein the hormone that synchronizes estrus is altrenogest.

66. The method according to any one of clauses 40 to 51 or 53 to 65 wherein the gonadotropin-releasing hormone is in a composition and the composition further comprises a stabilizer wherein the stabilizer is L-methionine.

67. The method of any one of clauses 40 to 51 or 53 to 66 wherein the gonadotropin-releasing hormone is in a composition with a pH of about 5 to about 6.

68. The method of any one of clauses 40 to 51 or 53 to 67 wherein the gonadotropin-releasing hormone is in a composition further comprising a preservative.

69. The method of clause 68 wherein the preservative is selected from the group consisting of methylparaben and propylparaben.

70. The method of any one of clauses 40 to 51 or 53 to 69 wherein the gonadotropin-releasing hormone is in a composition and the composition comprises methylparaben, propylparaben, sodium chloride, sodium citrate, L-methionine, citric acid, triptorelin, and methylcellulose.

71. The method of clause 70 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount that provides a viscosity of about 250 cP to about 400 cP.

72. The method according to any one of clauses 40 to 53 or 60 to 65 wherein the gonadotropin-releasing hormone is in an excipient selected from the group consisting of buffered saline, a liquid alcohol, a glycol, a glucose solution, an ester, an amide, and sterile water.

73. The method of clause 72 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

74. The method of any one of clauses 40 to 73 further comprising the step of exposing the gilt to a boar.

75. The method of any one of clauses 40 to 74 wherein the hormone for synchronizing estrus is administered by feeding.

76. The method of any one of clauses 40 to 75 wherein the gonadotropin-releasing hormone is administered about 118 to about 124 hours after the last daily administration of the hormone for synchronizing estrus.

77. The method of any one of clauses 40 to 75 wherein the gonadotropin-releasing hormone is administered about 124 to about 132 hours after the last daily administration of the hormone for synchronizing estrus.

78. The method of any one of clauses 40 to 77 wherein the gilt is inseminated the first time within about two hours of the time of administration of the gonadotropin-releasing hormone, if the gilt is in estrus on the fifth day after the last daily administration of the hormone for synchronizing estrus.

79. The method of any one of clauses 40 to 78 wherein the gilt is inseminated on the sixth day about 24 to about 28 hours after administration of the gonadotropin-releasing hormone.

80. A method for synchronizing time of insemination in a gilt, the method comprising the steps of:
  administering to the gilt a hormone for synchronizing estrus;
  administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus;
  inseminating the gilt a first time at about 2 to about 7 hours after administration of the gonadotropin-releasing hormone; and
  inseminating the gilt a second time on the sixth day after the last daily administration of the hormone for synchronizing estrus wherein the first and second inseminations are done without monitoring estrus.

81. The method according to clause 80 wherein the gonadotropin-releasing hormone has the formula

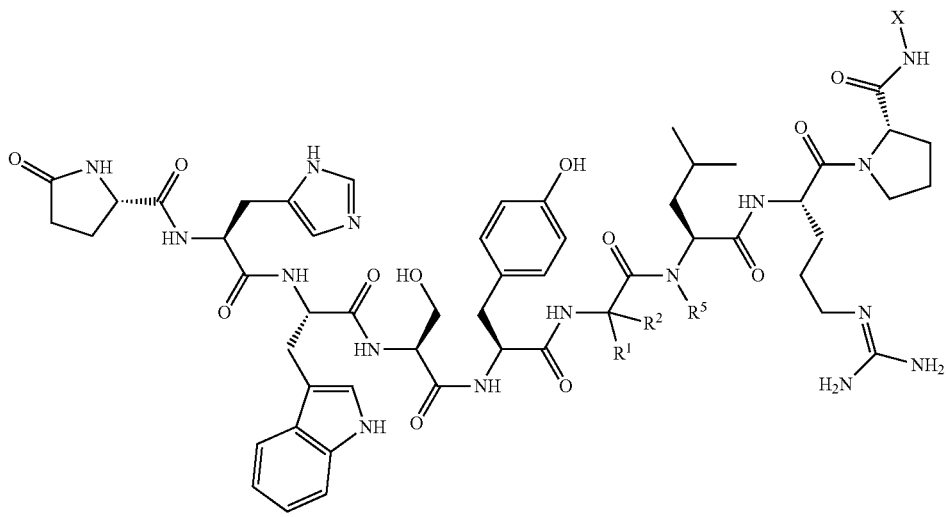

or a solvate, a hydrate, or a pharmaceutically acceptable salt thereof wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;

$R^5$ is hydrogen or alkyl; and

X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

82. The method according to clause 81 wherein the gonadotropin-releasing hormone is selected from the group consisting of compounds of the formula of claim 81 wherein
a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
b) $R^1$ is hydrogen, $R^2$ is hydrogen, X is $CH_2(CO)NH_2$; and $R^5$ is hydrogen;
c) $R^1$ is 1H-1-benzyl-imidazol-4-yl-methyl, $R^2$ is hydrogen, X is ethyl; and $R^5$ is hydrogen;
d) $R^1$ is 2-methylpropyl, $R^2$ is hydrogen, X is ethyl; and $R^5$ is hydrogen;
e) $R^1$ is 2-naphthlymethyl, $R^2$ is hydrogen, X is $CH_2(CO)NH_2$; and $R^5$ is hydrogen;
f) $R^1$ is t-butoxymethyl, $R^2$ is hydrogen, X is ethyl; $R^5$ is hydrogen; and the configuration of the carbon to which $R^1$ is attached is R;
g) $R^1$ is benzyl, $R^2$ is hydrogen, X is $CH_2(CO)NH_2$; $R^5$ is hydrogen; and the configuration of the carbon to which $R^1$ is attached is R;
h) $R^1$ is t-butoxymethyl, $R^2$ is hydrogen, X is $HN(CO)NH_2$; and $R^5$ is hydrogen;
i) $R^1$ is 1H-indol-3-yl-methyl, $R^2$ is hydrogen, X is ethyl; and $R^5$ is hydrogen;
j) $R^1$ is methyl, $R^2$ is hydrogen, X is hydrogen; $R^5$ is hydrogen; and the configuration of the carbon to which $R^1$ is attached is R;
k) $R^1$ is 1H-indol-3-yl-methyl, $R^2$ is hydrogen, X is ethyl; $R^5$ is methyl; and the configuration of the carbon to which $R^1$ is attached is R;
l) $R^1$ is methyl, $R^2$ is hydrogen, X is $CH_2(CO)NH_2$; $R^5$ is hydrogen; and the configuration of the carbon to which $R^1$ is attached is R;
m) $R^1$ is 4-aminobutyl, $R^2$ is hydrogen, X is $HN(CO)NH_2$; $R^5$ is hydrogen; and the configuration of the carbon to which $R^1$ is attached is R;
n) $R^1$ is methyl, $R^2$ is methyl, X is $HN(CO)NH_2$; and $R^5$ is hydrogen; and
o) $R^1$ is ethyl, $R^2$ is hydrogen, X is hydrogen; $R^5$ is hydrogen; and the configuration of the carbon to which $R^1$ is attached is R.

83. The method according to any one of clause 80 to 82 wherein the insemination is an artificial insemination.

84. The method according to any one of clauses 80 to 83 wherein the gonadotropin-releasing hormone is administered in an effective amount and the effective amount of the gonadotropin-releasing hormone is about 1 μg to about 500 μg.

85. The method according to any one of clauses 80 to 84 wherein the gonadotropin-releasing hormone is administered in an effective amount and the effective amount of the gonadotropin-releasing hormone is about 100 μg to about 300 μg.

86. The method according to any one of clauses 80 to 85 wherein the gonadotropin-releasing hormone is administered in an effective amount and the effective amount of the gonadotropin-releasing hormone is about 200 μg.

87. The method according to any one of clauses 80 to 86 wherein the gonadotropin-releasing hormone is at a concentration of about 50 μg/mL to about 200 μg/mL.

88. The method according to any one of clauses 80 to 87 wherein the gonadotropin-releasing hormone is at a concentration of about 50 μg/mL to about 150 μg/mL.

89. The method of any one of clauses 80 to 88 wherein the gonadotropin-releasing hormone is at a concentration of about 100 μg/mL.

90. The method according to any one of clauses 80 to 89 wherein the dose of the gonadotropin-releasing hormone is administered using a method selected from the group consisting of use of a deposition catheter, manual administration, and injection.

91. The method of clause 90 wherein the gonadotropin-releasing hormone is administered using a deposition catheter.

92. The method of clause 90 wherein the gonadotropin-releasing hormone is administered by injection.

93. The method according to any one of clauses 80 to 92 wherein the gonadotropin-releasing hormone in acetate form.

94. The method according to any one of clauses 80 to 91 or 93 wherein the gonadotropin-releasing hormone is administered in a composition comprising a gel.

95. The method according to clause 94 wherein the gel is a polysaccharide selected from the group consisting of celluloses, dextrans, and alginates.

96. The method according to clause 95 wherein the polysaccharide is a cellulose and the cellulose is methylcellulose.

97. The method of clause 96 wherein the gel comprises about 0.5 weight % to about 4.0 weight % of methylcellulose.

98. The method of clause 97 wherein the gel is 1.2% methylcellulose.

99. The method according to clause 94 wherein the gel has a viscosity of about 200 cP to about 5,000 cP.

100. The method of any one of clauses 90 to 91 or 93 to 99 wherein the gonadotropin-releasing hormone is administered intravaginally.

101. The method of clause 100 wherein the gonadotropin-releasing hormone is administered into the anterior vagina.

102. The method according to any one of clauses 80 to 101 wherein the method results in fertility of the gilt.

103. The method according to any one of clauses 81 to 102 wherein in the formula X is $H_2CC(O)NH_2$, $R_1$ is hydrogen, and $R_2$ is

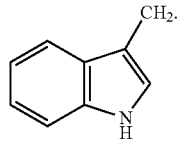

104. The method of any one of clauses 80 to 103 wherein the gonadotropin-releasing hormone is triptorelin.

105. The method of any one of clauses 80 to 104 wherein the hormone that synchronizes estrus is altrenogest.

106. The method according to any one of clauses 80 to 91 or 93 to 105 wherein the gonadotropin-releasing hormone is in a composition and the composition further comprises a stabilizer wherein the stabilizer is L-methionine.

107. The method of any one of clauses 80 to 91 or 93 to 106 wherein the gonadotropin-releasing hormone is in a composition with a pH of about 5 to about 6.

108. The method of any one of clauses 80 to 91 or 93 to 107 wherein the gonadotropin-releasing hormone is in a composition further comprising a preservative.

109. The method of clause 108 wherein the preservative is selected from the group consisting of methylparaben and propylparaben.

110. The method of any one of clauses 80 to 91 or 93 to 109 wherein the gonadotropin-releasing hormone is in a composition and the composition comprises methylparaben, propylparaben, sodium chloride, sodium citrate, L-methionine, citric acid, triptorelin, and methylcellulose.

111. The method of clause 110 wherein the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methylcellulose in an amount that provides a viscosity of about 250 cP to about 400 cP.

112. The method according to any one of clauses 80 to 93 or 100 to 105 wherein the gonadotropin-releasing hormone is in an excipient selected from the group consisting of buffered saline, a liquid alcohol, a glycol, a glucose solution, an ester, an amide, and sterile water.

113. The method of clause 112 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

114. The method of any one of clauses 80 to 113 further comprising the step of exposing the gilt to a boar.

115. The method of any one of clauses 80 to 114 wherein the hormone for synchronizing estrus is administered by feeding.

116. The method of any one of clauses 80 to 115 wherein the gonadotropin-releasing hormone is administered about 118 to about 124 hours after the last daily administration of the hormone for synchronizing estrus.

117. The method of any one of clauses 80 to 115 wherein the gonadotropin-releasing hormone is administered about 124 to about 132 hours after the last daily administration of the hormone for synchronizing estrus.

118. The method of any one of clauses 80 to 117 wherein the gilt is inseminated the first time about 2 to about 4 hours after administration of the gonadotropin-releasing hormone.

119. The method of any one of clauses 80 to 118 wherein the gilt is inseminated the second time about 24 to about 28 hours after administration of the gonadotropin-releasing hormone.

120. The method of any one of clauses 80 to 119 wherein the gilt is inseminated the first time about 2 to about 3 hours after administration of the gonadotropin-releasing hormone.

121. The method of any one of clauses 1 to 120 wherein the litter size of the gilt is similar to the litter size of control gilts inseminated based on daily estrus detection.

122. The method of any one of clauses 1 to 121 wherein the total piglets born alive to the gilt is similar to the total piglets born alive to control gilts inseminated based on daily estrus detection.

As used herein, "control gilts inseminated based on daily estrus detection" means gilts inseminated based on standard procedures used on farms (i.e., a daily regimen for monitoring estrus) where gilts are monitored for estrus for two to eight or more days to predict the optimal time for insemination. All of the illustrative embodiments, modifications, and alternative forms described below may be applied to the embodiments described in the preceding paragraphs of this Detailed Description of Illustrative Embodiments section and to the embodiments described in the Summary of Invention.

The methods for synchronizing the time of insemination in gilts described herein include the step of administering to the gilt, a dose of a gonadotropin-releasing hormone. In accordance with one embodiment, the hormone is administered to any porcine species, e.g., sows or gilts (i.e., female pigs prior to first mating), including pubertal gilts, and including gilts that are sexually mature (i.e., have had at least one estrus cycle) or are sexually immature (i.e., have not had an estrus cycle). The methods described herein may result in fertility of the gilt. The methods described herein are typically as effective in optimizing reproductive performance of gilts as a daily regimen for monitoring estrus, including, but not limited to, litter size and total piglets born alive.

In one embodiment, a method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration of the hormone for synchronizing estrus, and 3) inseminating the gilt, without monitoring estrus, only one time on the sixth day after the last daily administration of the hormone for synchronizing estrus.

Illustratively, in the embodiment of the preceding paragraph, gilts typically receive a single dose of the gonadotropin-releasing hormone, without administration of any other hormone for synchronizing ovulation, on the fifth day after the last daily administration to the gilt of a hormone for synchronizing estrus (e.g., altrenogest). In this embodiment, the gonadotropin-releasing hormone can be administered, for example, on the fourth day after the last daily administration to the gilt of the hormone for synchronizing estrus. In another illustrative embodiment, the gonadotropin-releasing hormone can be administered on the fifth day after the last daily administration to the gilt of the hormone for synchronizing estrus, e.g., about 120 or about 128 hours after the last daily administration to the gilt of the hormone for synchronizing estrus. As used herein, the phrases "the fourth day after the last daily administration of the hormone for synchronizing estrus", "the fifth day after the last daily administration of the hormone for synchronizing estrus", and "the sixth day after the last daily administration of the hormone for synchronizing estrus" mean day 4, day 5, or day 6, respectively, after the last daily administration to the gilt of the hormone for synchronizing estrus, where the last daily administration to the gilt of the hormone for synchronizing estrus is day 0.

In another embodiment, the gonadotropin-releasing hormone can be administered at about 105 to about 120, at about 105 to about 136, at about 116 to about 126, about 117 to about 125, about 117 to about 124, about 118 to about 122, about 119 to about 121, or about 120 hours after the last daily administration to the gilt of the hormone for synchronizing estrus. In alternative embodiments the gonadotropin-releasing hormone can be administered at about 117, about 118, about 119, about 120, about 121, about 122, about 123, or about 124 hours after the last daily administration to the gilt of the hormone for synchronizing estrus.

In another embodiment, the gonadotropin-releasing hormone can be administered at about 124 to about 134, about 125 to about 133, about 125 to about 132, about 126 to about 130, about 127 to about 129, or about 128 hours after the last daily administration to the gilt of the hormone for synchronizing estrus. In alternative embodiments the gonadotropin-releasing hormone can be administered at about 125, about 126, about 127, about 128, about 129, about 130, about 131, or about 132 hours after the last daily administration to the gilt of the hormone for synchronizing estrus.

In another embodiment, gilts receiving treatment with the gonadotropin-releasing hormone are typically inseminated a single time at 20 hours (or 20 hours±2 hr), 22 hours (or 22 hours±2 hr), 23 hours (or 23 hours±2 hr), 24 hours (or 24 hours±2 hr), 25 hours (or 25 hours±2 hr), 26 hours (or 26 hours±2 hr), 27 hours (or 27 hours±2 hr), 28 hours (or 28 hours±2 hr), 29 hours (or 29 hours±2 hr), or 30 hours (or 30 hours±2 hr) post administration of the gonadotropin-releasing hormone.

In another embodiment, the gilt can also be inseminated one time, for example, about 24 to about 28 hours after administration of the gonadotropin-releasing hormone. In various additional illustrative embodiments, the gilt is inseminated about 22 to about 30 hours after administration of the gonadotropin-releasing hormone, about 10 to about 40 hours, about 23 to about 29 hours, about 24 to about 27 hours, or about 23 to about 30 hours after administration of the gonadotropin-releasing hormone. In this embodiment, the gilt is inseminated without monitoring estrus. As used herein the phrase "without monitoring estrus" means that tests well known in the art for detecting whether an animal is in estrus are not done.

A method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus. 3) monitoring estrus on the fifth day after the last daily administration of the hormone for synchronizing estrus, 4) then inseminating the gilt on the fifth day after the last daily administration of the hormone for synchronizing estrus, if the gilt is in estrus, wherein the gilt is inseminated in combination with administration of the gonadotropin-releasing hormone, and 5) if the gilt is in estrus or is not in estrus on the fifth day after the last daily administration of the hormone for synchronizing estrus, inseminating the gilt on the sixth day after the last daily administration of the hormone for synchronizing estrus wherein estrus is not monitored on the sixth day after the last daily administration of the hormone for synchronizing estrus.

Illustratively, in the embodiment of the preceding paragraph, gilts typically receive a single dose of the gonadotropin-releasing hormone, without administration of any other hormone for synchronizing ovulation, after the last daily administration to the gilt of a hormone for synchronizing estrus (e.g., altrenogest). In this embodiment, the gonadotropin-releasing hormone can be administered, for example, on the fourth day after the last daily administration to the gilt of the hormone for synchronizing estrus. In another illustrative embodiment, the gonadotropin-releasing hormone can be administered on the fifth day after the last daily administration to the gilt of the hormone for synchronizing estrus, e.g., about 120 or about 128 hours after the last daily administration to the gilt of the hormone for synchronizing estrus. For this embodiment, the phrases "the fourth day after the last daily administration of the hormone for synchronizing estrus", "the fifth day after the last daily administration of the hormone for synchronizing estrus", and "the sixth day after the last daily administration of the hormone for synchronizing estrus" mean day 4, day 5, or day 6, respectively, after the last daily administration to the gilt of the hormone for synchronizing estrus, where the last daily administration to the gilt of the hormone for synchronizing estrus is day 0.

In another embodiment, the gonadotropin-releasing hormone can be administered in this embodiment at about 105 to about 120, at about 105 to about 136, at about 116 to about 126, about 117 to about 125, about 117 to about 124, about 118 to about 122, about 119 to about 121, or about 120 hours after the last daily administration to the gilt of the hormone for synchronizing estrus. In alternative embodiments the gonadotropin-releasing hormone can be administered at about 117, about 118, about 119, about 120, about 121, about 122, about 123, or about 124 hours after the last daily administration to the gilt of the hormone for synchronizing estrus.

In another embodiment, the gonadotropin-releasing hormone can be administered at about 124 to about 134, about 125 to about 133, about 125 to about 132, about 126 to about 130, about 127 to about 129, or about 128 hours after the last daily administration to the gilt of the hormone for synchronizing estrus. In alternative embodiments the gonadotropin-releasing hormone can be administered at about 125, about 126, about 127, about 128, about 129, about 130, about 131, or about 132 hours after the last daily administration to the gilt of the hormone for synchronizing estrus.

In another embodiment, gilts receiving treatment with the gonadotropin-releasing hormone are inseminated one or two times. The gilts can be inseminated in combination with administration of the gonadotropin-releasing hormone, if the gilt is in estrus on the fifth day after the last daily administration of the hormone for synchronizing estrus (e.g., altrenogest). As used herein, "in combination with administration of the gonadotropin-releasing hormone" means that the gilt is inseminated on the fifth day after the last daily administration of the hormone for synchronizing estrus and the gonadotropin-releasing hormone is administered to the gilt on the same day (i.e., the fifth day). The insemination and the administration of the gonadotropin-releasing hormone to the gilt can be done in any order. For example, the gilt can be inseminated in the morning of the fifth day after the last daily administration of the hormone for synchronizing estrus, and the gonadotropin-releasing hormone can be administered to the gilt at any time thereafter during the fifth day. In this embodiment, the gonadotropin-releasing hormone is preferably administered to the gilt at least two hours after the gilt is inseminated. In another embodiment, the gonadotropin-releasing hormone can be administered to the gilt first, for example, in the morning of the fifth day after the last daily administration of the hormone for synchronizing estrus. The gilt can then be inseminated at any time thereafter during the fifth day after the gonadotropin-releasing hormone has been administered to the gilt. In this embodiment, the gilt is preferably inseminated at least two hours after the gonadotropin-releasing hormone is administered. In various other embodiments, the gilt is inseminated within about two hours of the time the gonadotropin-releasing hormone is administered. For example, the insemination can be done within about 10 minutes, within about 20 minutes, within about 30 minutes, within about 45 minutes, within about 60 minutes, within about 75 minutes, or within about 120 minutes of the time of administration of the gonadotropin-releasing hormone regardless of the order of insemination of the gilt and administration of the gonadotropin-releasing hormone to the gilt.

Accordingly, in another embodiment, the insemination on the fifth day can be done at about 108 to about 120, at about 108 to about 132, at about 116 to about 126, about 117 to about 125, about 117 to about 124, about 118 to about 122, about 119 to about 121, or about 120 hours after the last daily administration to the gilt of the hormone for synchronizing estrus. In other illustrative embodiments, the insemination on the fifth day can be done at about 124 to about 134, about 125 to about 133, about 125 to about 132, about 126 to about 130, about 127 to about 129, or about 128 hours after the last daily administration to the gilt of the hormone for synchronizing estrus.

In another embodiment, the gilts are inseminated on the sixth day at 22 hours (or 22 hours±2 hr), 23 hours (or 23 hours±2 hr), 24 hours (or 24 hours±2 hr), 25 hours (or 25 hours±2 hr), 26 hours (or 26 hours±2 hr), 27 hours (or 27 hours±2 hr), 28 hours (or 28 hours±2 hr), 29 hours (or 29 hours±2 hr), or 30 hours (or 30 hours±2 hr) post administration of the gonadotropin-releasing hormone.

In another embodiment, the gilt can be inseminated on the sixth day after the last daily administration of the hormone for synchronizing estrus, for example, about 24 to about 28 hours after administration of the gonadotropin-releasing hormone. In various further illustrative embodiments, the gilt is inseminated on the sixth day after the last daily administration of the hormone for synchronizing estrus at about 22 to about 30 hours after administration of the gonadotropin-releasing hormone, about 10 to about 40 hours, about 23 to about 29 hours, about 24 to about 27 hours, or about 23 to about 30 hours after administration of the gonadotropin-releasing hormone. In this embodiment, the gilt is inseminated on the fifth day after the last daily administration of the hormone for synchronizing estrus if the gilt is in estrus (i.e., estrus is monitored on the fifth day after the last daily administration of the hormone for synchronizing estrus). The gilt is inseminated on the sixth day after the last daily administration of the hormone for synchronizing estrus without monitoring estrus.

A method for synchronizing time of insemination in a gilt is provided. The method comprises the steps of 1) administering to the gilt a hormone for synchronizing estrus, 2) administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration to the gilt of the hormone for synchronizing estrus, 3) inseminating the gilt a first time at about 2 to about 7 hours after administration of the gonadotropin-releasing hormone, and 4) inseminating the gilt a second time on the sixth day after the last daily administration of the hormone for synchronizing estrus wherein the first and second inseminations are done without monitoring estrus.

Illustratively, in the embodiment of the preceding paragraph, gilts typically receive a single dose of the gonadotropin-releasing hormone, without administration of any other hormone for synchronizing ovulation, on the fifth day after the last daily administration to the gilt of a hormone for synchronizing estrus (e.g., altrenogest). In this embodiment, the gonadotropin-releasing hormone can be administered, for example, on the fourth day after the last daily administration to the gilt of the hormone for synchronizing estrus. In another illustrative embodiment, the gonadotropin-releasing hormone can be administered on the fifth day after the last daily administration to the gilt of the hormone for synchronizing estrus, e.g., about 120 or about 128 hours after the last daily administration to the gilt of the hormone for synchronizing estrus. For this embodiment, the phrases "the fourth day after the last daily administration of the hormone for synchronizing estrus", "the fifth day after the last daily administration of the hormone for synchronizing estrus", and "the sixth day after the last daily administration of the hormone for synchronizing estrus" mean day 4, day 5, or day 6, respectively, after the last daily administration to the gilt of the hormone for synchronizing estrus, where the last daily administration to the gilt of the hormone for synchronizing estrus is day 0.

In another embodiment, the gonadotropin-releasing hormone can be administered in this embodiment at about 105 to about 120, at about 105 to about 136, at about 116 to about 126, about 117 to about 125, about 117 to about 124, about 118 to about 122, about 119 to about 121, or about 120 hours after the last daily administration to the gilt of the hormone for synchronizing estrus. In alternative embodiments the gonadotropin-releasing hormone can be administered at about 117, about 118, about 119, about 120, about 121, about 122, about 123, or about 124 hours after the last daily administration to the gilt of the hormone for synchronizing estrus.

In another embodiment, the gonadotropin-releasing hormone can be administered at about 124 to about 134, about 125 to about 133, about 125 to about 132, about 126 to about 130, about 127 to about 129, or about 128 hours after the last daily administration to the gilt of the hormone for synchronizing estrus. In alternative embodiments the gonadotropin-releasing hormone can be administered at about 125, about 126, about 127, about 128, about 129, about 130, about 131, or about 132 hours after the last daily administration to the gilt of the hormone for synchronizing estrus.

In another embodiment, gilts receiving treatment with the gonadotropin-releasing hormone are typically inseminated two times. The gilts are inseminated a first time at about 2 hours to about 8 hours after administration of the gonadotropin-releasing hormone or about 2 hours to about 14 hours after administration of the gonadotropin-releasing hormone. In other embodiments the first insemination can be at about 2 hours to about 7 hours, at about 2 hours to about 6 hours, at about 2 hours to about 5 hours, or at about 2 hours to about 4 hours after administration of the gonadotropin-releasing hormone.

In another embodiment, the gilts are inseminated a second time at 22 hours (or 22 hours±2 hr), 23 hours (or 23 hours±2 hr), 24 hours (or 24 hours±2 hr), 25 hours (or 25 hours±2 hr), 26 hours (or 26 hours±2 hr), 27 hours (or 27 hours±2 hr), 28 hours (or 28 hours±2 hr), 29 hours (or 29 hours±2 hr), or 30 hours (or 30 hours±2 hr) post administration of the gonadotropin-releasing hormone.

In another embodiment, the gilt can also be inseminated the second time, for example, about 24 to about 28 hours after administration of the gonadotropin-releasing hormone. In various further illustrative embodiments, the gilt is inseminated the second time at about 22 to about 30 hours after administration of the gonadotropin-releasing hormone, about 10 to about 40 hours, about 23 to about 29 hours, about 24 to about 27 hours, or about 23 to about 30 hours after administration of the gonadotropin-releasing hormone. In this embodiment, the gilt is inseminated the first time and the second time without monitoring estrus. As used herein the phrase "without monitoring estrus" means that tests well known in the art for detecting whether an animal is in estrus are not done.

Any of the embodiments described below, are applicable to any of the above-described embodiments. Any of the embodiments described below, including any of the gonadotropin-releasing hormone embodiments and any methods of administration (e.g., injection or intravaginal administration in a gel composition described herein), are also applicable to a method for synchronizing time of insemination in a sow, except where the embodiments are specifically limited to gilts. The method comprises the steps of 1) administering to the sow a single dose of a gonadotropin-releasing hormone for synchronizing ovulation, without administration of any other hormone for synchronizing ovulation, wherein the gonadotropin-releasing hormone is administered on the fourth day after weaning, and 3) inseminating the sow, without monitoring estrus, only one time about 18 to about 24 hours after administration of the gonadotropin-releasing hormone, for example, about 20±2 hours or about 20±1 after administration of the gonadotropin-releasing hormone.

Breeding of the animal may be by any means, including artificial insemination (AI), or through natural breeding. In any embodiment described herein, a second breeding or subsequent breedings (e.g., artificial insemination) may be performed. In yet another embodiment, the swine is inseminated artificially only one time. In another illustrative aspect, there is no estrus detection (i.e., monitoring of estrus). In another illustrative embodiment, the methods described herein can further comprise the step of exposing the gilt or the sow to a boar during the process of monitoring estrus to establish the timing of artificial insemination.

In any embodiment described herein, compositions for synchronizing the time of insemination in a swine comprise: a) a gonadotropin-releasing hormone; and b) a pharmaceutically acceptable pH buffering agent to provide a pH in the range of about pH 4 to about pH 9. The pH of the composition described can range from about 4 to about 9. In other embodiments, the pH can range from about 4 to about 8, from about 4 to about 7, from about 4.5 to about 6.5, about 4.5 to about 6, or from about 5 to about 6.

Further, the gonadotropin-releasing hormone compositions can be produced, in accordance with the dosage form, through a routine method by appropriately mixing with, diluting with, or dissolving in an additive such as various excipients, disintegrants, binders, salts, lubricants, local anesthetics (e.g., lidocaine), diluents, preservatives, chelating agents, buffers, tonicity agents, antiseptic agents, wetting agents, emulsifiers, dispersants, stabilizers, a solution adjuvant, or combinations thereof.

Illustratively, the compositions comprising the gonadotropin-releasing hormone can be in the form of a gel and the composition can have, for example, a viscosity of about 10 cP (centipoise) to about 300,000 cP. In various illustrative embodiments, the viscosity of the composition can be about 100 cP to about 100,000 cP, about 250 cP to about 400 cP, about 300 cP to about 400 cP, about 500 cP to about 100,000 cP, about 700 cP to about 100,000 cP, about 200 cP to about 20,000 cP, about 200 cP to about 10,000 cP, about 200 cP to about 5,000 cP, about 200 to about 1,000 cP, about 200 cP to about 600 cP, about 100 cP to about 600 cP, about 100 cP to about 500 cP, about 200 cP to about 500 cP, about 200 cP to about 450 cP, or about 100,000 cP to about 250,000 cP. In accordance with various embodiments described herein, the viscosity of the composition can be about 200 cP, about 250 cP, about 300 cP, about 400 cP, about 500 cP, about 1,000 cP, about 15,000 cP, about 20,000 cP, about 30,000 cP, about 40,000 cP, about 50,000 cP, about 75,000 cP, about 100,000 cP, about 200,000 cP, or about 300,000 cP. The viscosity of a solution can be measured using a viscometer, such as a rheometer, based on techniques well-known in the art. The term gel includes viscous solutions that are not solidified.

Typically, the gels as described herein comprise about 0.001 to about 3.0% weight/weight (w/w) of the gonadotropin-releasing hormone or a salt thereof, more typically about 0.5-5.0% (w/w) or about 0.1-5.0% (w/w) of the gonadotropin-releasing hormone or a salt thereof, a preservative, a gel (i.e., a viscosity-modifying agent such as methylcellulose), a buffer to maintain a pH between about 5 to about 6, and a tonicity agent to maintain a tonicity between about 200 to about 400 mOsm/kG.

In accordance with any embodiment described herein, the composition is sufficiently viscous that the composition may adhere to the target tissue (e.g., vaginal tissue) for a sufficient time to deliver an effective amount of the gonadotropin-releasing hormone to the gilt or the sow. The typical viscosity will depend on factors such as, for example, the rate of penetration of the gonadotropin-releasing hormone and the quantity of the gonadotropin-releasing hormone that is applied. Suitable viscosity modulating agents include but are not limited to, ionic and non-ionic water soluble polymers; crosslinked acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof.

The viscosity modulating agent may be in the form of a gel, paste, cream, ointment, and the like. In one embodiment, the composition comprises a gonadotropin-releasing hormone and a gel (e.g., to form a viscous solution), as a viscosity modifying agent, and the gonadotropin-releasing hormone is administered in the composition comprising the gel. In one embodiment, the gel is a hydrogel, a lipogel, or a viscous sol. In another embodiment, the gel is a hydrogel. The gel may be prepared using any method known in the art, for example, such as those methods described in U.S. Pat. Nos. 6,908,623 and 7,456,207, incorporated herein by reference.

In any embodiment described herein, the gel (i.e., a viscosity modifying agent) comprises a polysaccharide. In accordance with the methods and compositions herein described, the polysaccharide may include, for example, alginates and glucose, such as glycogens, starches (e.g., amylose and amylopectin), celluloses, and dextrans. The polysaccharide can be, for example, a methyl, ethyl, or propyl cellulose ester, ether, hydroxy-ether, hydroxy-alkyl, or hydroxy-ester. To achieve the desired viscosity, a sufficient amount of one or more polysaccharides may be used. Typically, about 0.25 to about 10 weight % polysaccharide (based on the total weight of the composition) is desirable. In another embodiment, the weight % of the polysaccharide is about 0.25 weight % to about 3.0 weight %, about 1.0 weight % to about 7 weight %, about 1.0 weight % to about 4.0 weight %, or about 1.0 weight % to about 2.0 weight %. In other embodiments, the weight % of the polysaccharide is about 0.1%, about 0.5%, about 0.75%, about 0.8%, about 0.9%, about 1.0%, about 1.1%, about 1.2%, about 1.4%, about 1.8%, about 2.0%, about 5%, about 8%, or about 10% (all in weight/weight). To increase the viscosity of the composition, the polysaccharide may be used in conjunction with one or more non-polysaccharide viscosifiers known in the art. Examples of non-polysaccharide viscosifiers that can be used in conjunction with one or more polysaccharides include xantham gum, alginic acids and salts thereof, magnesium aluminum silicate, dextrins, sucrose and derivatives thereof, and mixtures thereof. The amount of non-polysaccharide viscosifier, if present, can be about 0.1 weight % to about 10 weight %, depending on the desired viscosity.

In any embodiment described herein, the gel can comprise a cellulose. Illustrative embodiments of the cellulose, as herein described, include methylcellulose, ethylcellulose, hydroxypropyl cellulose, carbomethyl cellulose, hydroxypropyl methyl cellulose, and hydroxyethyl methyl cellulose. The cellulose can be a cellulose derivative, preferably a non-ionic cellulose ester, ether, hydroxy-ether, or hydroxy-ester, or a non-ionic starch derivative. Typically, about 0.25 weight % to about 10 weight % of the cellulose (based on the total weight of the composition) is desirable. In another embodiment, the weight % of the cellulose is about 0.25 weight % to about 3.0 weight %, about 0.5 weight % to about 3.0 weight %, about 0.5 weight % to about 4.0 weight %, about 1.0 weight % to about 7 weight %, about 1.0 weight % to about 4.0 weight %, or about 1.0 weight % to about 2.0 weight %. In other embodiments, the weight % of the cellulose is about 0.1%, about 0.5%, about 0.75%, about 0.8%, about 0.9%, about 1.0%, about 1.1%, about 1.2%, about 1.4%, about 1.8%, about 2.0%, about 5%, about 8%, or about 10% (all in weight/weight). If a uniform gel is desired, dispersing agents such as alcohol, sorbitol, or glycerin can be added, or the gelling agent can be dispersed by tituration, mechanical mixing, or stirring, or combinations thereof.

Acceptable stabilizers for use in the compositions for the methods described herein include, an L-amino acid, such as an L-methionine. In other embodiments, stabilizers that can be used include, but are not limited to, polysaccharides such as acacia, agar, alginic acid, guar gum and tragacanth, gelatin and synthetic and semi-synthetic polymers such as carbomer resins, cellulose ethers, and carboxymethyl chitin. The stabilizer is generally in an amount of about 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume). In one embodiment, in the presence of a stabilizer as herein described, the shelf-life of the composition can be at least 12 months, at least 18 months, or at least 24 months. In another embodiment, the composition can be stored at temperatures ranging from about 2° C. to about 8° C. Inert carriers can also be included such as lactose, starch, dextrin, dicalcium phosphate, and calcium sulfate. In one embodiment including a stabilizer, the composition is chemically stable and remains at least 97%, at least 98%, at least 99% pure, at least 99.5% pure, or at least 99.7% pure, for at least three months.

The tonicity agent can be non-ionic or ionic. Illustratively, acceptable tonicity agents for use in the compositions for the methods described herein include, for example, ionic agents such as sodium chloride, potassium chloride, or a balanced salt solution. In accordance with one embodiment, the tonicity agent is present in an amount to achieve a tonicity between about 200-400 mOsm/kG, about 220-380 mOsm/kG, or about 250-340 mOsm/kG. Non-ionic tonicity agents include diols, such as glycerol, mannitol, erythritol, polyethylene glycol, propylene glycol; and sugars such as sucrose and dextrose. The tonicity agent is generally in an amount of about 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, 0.5 to about 2.0%, about 0.6 to about 2.0%, about 0.5 to about 1.8%, about 0.6 to about 1.8%, about 1.0 to about 5.0%, about 1.0 to about 10%, or about 1.0 to about 20% (all in weight/volume).

In any embodiment described herein, the pH buffering agents for use in the compositions for the methods described herein are those agents known to the skilled artisan to be pH buffering agents or compositions and include, for example, acetate, borate, carbonate, citrate, and phosphate buffers, as well as various biological buffers, for example, TAPS, Bicine, Tris, Tricine, HEPES, TES, MOPS, PIPES, Cacodylate, and MES. Other pH buffering agents include hydrochloric acid, sodium hydroxide, magnesium oxide, monopotassium phosphate, bicarbonate, ammonia, carbonic acid, sodium citrate, citric acid, acetic acid, disodium hydrogen phosphate, borax, boric acid, and the like. The buffering agent is generally in an amount of about 0.01 to about 10%, about 0.02 to about 10%, about 0.02 to about 5%, about 0.02 to about 2.0%, about 0.02 to about 1.0%, about 0.02 to about 0.5%, about 0.05 to about 10.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

The pH buffering agent used in the formulations described herein can be used at any concentration needed to obtain the desired pH range. For example, the buffering agent can be used at a concentration of about 0.001M to about 1M, about 0.001M to about 2M, about 0.001M to about 5M, about 0.05M to about 0.1M, about 0.05M to about 0.2M, about 0.05M to about 1M, 0.05M to about 2M, about 0.05 to about 5M, about 0.1M to about 1M, about 0.1M to about 2M, about 0.1M to about 5M. Any amount of buffering agent needed to obtain the desired pH range can be used in the formulations described herein. Typically, the pharmaceutically acceptable pH buffering agent can be used to provide a pH in the range of about pH 4 to about pH 9. The pH of the composition herein described can range from about 3 to about 10, or about 4 to about 9. In any embodiment described herein, the pH can range from about 4 to about 8, from about 4 to about 7, from about 4.5 to about 6.5, about 4.5 to about 6, from about 5 to about 6, about 5 to about 5.5, about 4 to about 6, or about 4.5 to about 5.5.

In any embodiment, the composition described herein can comprise one or more pharmaceutically acceptable preservatives. As used herein, the term "preservative" includes an agent or a combination of agents that aids in stabilizing the composition, inhibiting microbial growth, or both. Examples of suitable preservatives include parabens (e.g., methyl, ethyl, propyl, and butyl esters of parahydroxybenzoic acid), propyl gallate, sorbic acid and its sodium and potassium salts, propionic acid and its calcium and sodium salts, "Dioxin" (6-acetoxy-2,4-dimethyl-m-dioxane), "Bronopol" (2-bromo-2-nitropropane-1,3-diol) and salicylanilides such as disbromosalicylanilide, tribromosalicylamides, "Cinaryl" 100 and 200 or "Dowicil" 100 and 200 (Cis isomer of 1-(3-chloroallyl-3,5,7-triaza-1-azanidadamantane chloride), hexachlorophene, sodium benzoate, citric acid, ethylene diaminetetraacetic acid and its alkali metal and alkaline earth metal salts, butyl hydroxyanisol, butyl hydroxytoluene, phenolic compounds such as chloro- and bromocresols and chloro- and bromo-oxylenols, quaternary ammonium compounds like benzalkonium chloride, aromatic alcohols such as phenylethyl alcohol, benzyl alcohol, etc., chlorobutanol, quinoline derivatives such as iodochlorohydroxyquinolin, and the like. The total amount of preservative, when present, is about 0.005 weight % to about 2 weight %, about 0.001 weight % to 1.0 weight %, about 0.005 weight % to about 0.25 weight %, or about 0.05 weight % to about 0.2 weight %, typically about 0.01 weight % to about 0.1 weight % (all in weight/weight).

In any embodiment, the pharmaceutical composition for the methods described herein can contain a chelating agent, such as those known to those skilled in the art, for example, ethylenediamine tetraacetate (EDTA), diethylenetriaminepentaacetic acid (DTPA), and N,N-bis(carboxymethyl)glycine (NTA), or salts thereof. The composition can contain about 0.003 weight % to about 1.0 weight %, about 0.02 weight % to about 0.2 weight %, about 0.01 weight % to about 1.0 weight %, or about 0.02 weight % to about 0.5 weight % (all in weight/volume) of the chelating agent.

In any embodiment described herein, antimicrobial agents can be included in the compositions for the methods described herein. Such agents may include, but are not limited to 5-chloro-2-(2,4-dichlorophenoxy)-phenol, 8-hydroxyquinoline, copper II compounds, phthalic acid, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, iodine, sulfonamides, bisbiguanides, phenolics, delmopinol, octapinol, and other piperidino derivatives, and nicin preparations, any suitable antibiotics such as augmentin, amoxicillin, tetracycline, doxycycline, minocycline, metronidazole, neomycin, kanamycin, and clindamycin, and any salts of any of these compounds where applicable, and any combinations of these compounds. In yet another embodiment, anti-fungal compounds can be included, alone or in combination with any of the above-described antimicrobials. Anti-fungal agents that are suitable for use in the compositions described herein include, but are not limited to, nystatin, miconazole, econazole nitrate, clotrimazole, and flucytosine. The antimicrobial or anti-fungal agents can be added to the formulations herein described in an amount of about 0.01 to about 10%, about 0.01 to about 5%, about 0.01 to about 2.0%, about 0.01 to about 1.0%, about 0.01 to about 0.5%, about 0.01 to about 0.2%, 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

In any embodiment of the compositions for the methods described herein, antioxidants can also be added. For example, antioxidants used herein can include beta-carotene, vitamin E, vitamin C, vitamin A, tocopherol, butylated hydroxytoluene, butylated hydroxyanisole, tertiary-butylhydroquinone, propyl gallate, ascorbic acid, sodium metabisulfite, uric acid, carotenoids, flavonoids, melatonin, and ethoxyquin. The antioxidants can be added to the formulations herein described in an amount of about 0.01 to about 10%, about 0.01 to about 5%, about 0.01 to about 2.0%, about 0.01 to about 1.0%, about 0.01 to about 0.5%, about 0.01 to about 0.2%, 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

In one embodiment, the gonadotropin-releasing hormone for use in the methods described herein is in a composition and the composition comprises methylparaben, propylparaben, sodium chloride, sodium citrate, L-methionine, citric acid, triptorelin, and methylcellulose. In another aspect, the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount of about 1.2% weight per volume (or with a viscosity of about 250 cP to about 400 cP).

The gonadotropin-releasing hormone composition for the methods described herein contains a gonadotropin-releasing hormone in an amount effective to synchronize the time of insemination in a gilt when used in the methods described herein. As used herein, "gonadotropin-releasing hormone" refers to any gonadotropin releasing hormone, including gonadotropin releasing hormone analogs and derivatives, and gonadotropin releasing hormone agonists and antagonists. In other embodiments, luteinizing hormone or human chorionic gonadotropin, or derivatives or analogs thereof, and combinations thereof can be used in place of, or in combination with the gonadotropin-releasing hormone. As used herein, "luteinizing hormone" refers to any luteinizing hormone, including luteinizing hormone analogs and derivatives, and luteinizing hormone agonists and antagonists. In one embodiment, the luteinizing hormone can be synthetic. In another embodiment, the luteinizing hormone can be LH (see, for example, U.S. Pat. No. 5,444,167, incorporated herein by reference). As used herein, "human chorionic gonadotropin" refers to any human chorionic gonadotropin, including human chorionic gonadotropin analogs and derivatives, and human chorionic gonadotropin agonists and antagonists. In one embodiment, the human chorionic gonadotropin can be synthetic. In another embodiment, the human chorionic gonadotropin can be hCG (see, for example, U.S. Pat. Nos. 6,469,139, 4,400,316, and 4,804,626, incorporated herein by reference). In yet another embodiment, eCG, hCG, and LH are not used in the methods described herein.

In one embodiment, the gonadotropin-releasing hormone can be synthetic. In another embodiment, the gonadotropin-releasing hormone can be in acetate form. In another embodiment, the gonadotropin-releasing hormone can be GnRH (pGlu-His-Trp-Ser-Tyr-Gly-Leu-Arg-Pro-GlyNH$_2$) (see, for example, U.S. Pat. No. 5,688,506, incorporated herein by reference) or triptorelin (pGlu-His-Trp-Ser-Tyr-D-Trp-Leu-Arg-Pro-Gly-NH$_2$).

Examples of gonadotropin releasing hormone agonists for use herein include, but are not limited to, leuprolide, nafarelin, buserelin, [DAla$^6$, des Gly-NH$_2$$^{10}$]GnRH, [DLys$^6$]GnRH, [DAla$^6$]GnRH, [2-Me-Ala$^6$]GnRH, [D-α-aminobutyroyl$^6$, des-GlyNH$_2$$^{10}$]GnRH, triptorelin, lutrelin, goserelin, deslorelin, and histrelin. Generally, gonadotropin-releasing hormone agonists are modeled after the natural gonadotropin releasing hormone decapeptide with specific amino acid substitutions typically at positions 6 and 10. Triptorelin is an example of a gonadotropin releasing hormone agonist with only a single substitution at position 6.

Examples of gonadotropin releasing hormone antagonists include Antide (a decapeptide represented by the formula D-Ac-D-2-Nal$^1$-DpClPhe$^2$-D-3-Pal$^3$-Ser4-NiLys$^5$-D-Nic-Lys$^6$-Leu$^7$-ILys$^8$-Pro$^9$-D-Ala$^{10}$), [Ac-D4ClDPhe$^1$, D4ClDPhe$^2$, DTrp$^3$, DArg$^6$, DAla$^{10}$]GnRH, [Ac-4ClDPhe$^2$, D$_3$Pal$^3$, Arg$^5$, D$_2$Nal$^6$, DAla$^{10}$]GnRH, [Ac-D2-Na$^1$1, 4ClD-Phe$^2$, DTrp$^3$, DArg$^6$, DAla$^{10}$]GnRH, [Ac-D2 Nal$^1$, 4FDPhe$^2$, DTrp$^3$, DArg$^6$]GnRH, [Ac-D2Nal$^1$, 4ClDPhe2, DTrp$^3$, DhArg(Et$_2$)$^6$, DAla$^{10}$]GnRH, and [Ac-Na$^1$1, DME4ClPhe$^2$, DPal$^3$, Ser$^4$, Tyr$^5$, DArg$^6$, Le$^7$, ILys$^8$, Pro$^9$, DAla$^{10}$]GnRH.

In any embodiment described herein, a gonadotropin-releasing hormone of formula (I) can be used

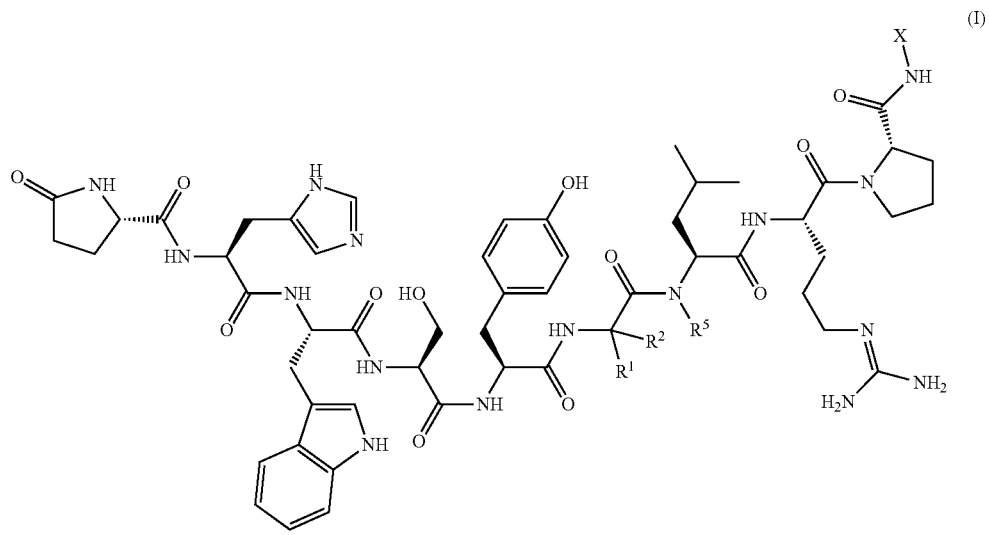

(I)

or a solvate, a hydrate, or a pharmaceutically acceptable salt thereof wherein

R$^1$ and R$^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or R$^1$ and R$^2$ and the attached carbon form a carbocycle or heterocycle;

R$^5$ is hydrogen or alkyl; and

X is hydrogen, or X is selected from the group consisting of alkyl, cycloalkyl, heteroalkyl, optionally substituted alkylene-carboxamide, and HNC(O)NR$^3$R$^4$, where R$^3$ and R$^4$ are in each instance independently selected from the group consisting of hydrogen, alkyl, heteroalkyl and haloalkyl.

In another embodiment, R$^1$ is a methylene-aryl. In another embodiment, the aryl is phenyl or 4-hydroxyphenyl. In another embodiment, R$^1$ is a methylene-heteroaryl. In yet another embodiment, the heteroaryl is selected from the group consisting of pyridyl, thiazolyl, pyridazolyl, pyrimidinyl, quinolinyl, pyrazolyl, imidazolyl, pyrrolyl, indolyl, benzopyrazolyl, and benzimidazolyl; and $R^2$ is hydrogen or methyl. In various other embodiments, $R^1$ is 2-methylpropyl, $R^1$ is 2-naphthylmethyl, $R^1$ is t-butoxymethyl, $R^1$ is methyl, $R^1$ is 4-aminobutyl, $R^1$ is ethyl, $R^1$ and $R^2$ are methyl, $R^1$ is 1H-indol-3-yl-methyl, $R^1$ is 1H-1-benzyl-imidazol-4-yl-methyl, or $R^1$ is benzyl.

In additional embodiments, $R^2$ is hydrogen, $R^2$ is hydrogen and the gonadotropin-releasing hormone has the R-configuration at the carbon to which $R^1$ is attached, $R^2$ is hydrogen and the gonadotropin-releasing hormone has the S-configuration at the carbon to which $R^1$ is attached, or $R^2$ is hydrogen and the gonadotropin-releasing hormone is a mixture of gonadotropin-releasing hormones having the R-configuration at the carbon to which $R^1$ is attached and the S-configuration at the carbon to which $R^1$ is attached.

In still additional embodiments, X is $CH_2(CO)NH_2$, X is $HN(CO)NH_2$, X is ethyl, X is hydrogen, $R^5$ is hydrogen, or $R^5$ is methyl.

In another embodiment, the gonadotropin-releasing hormone is a hormone of formula I where $R^1$ is 1H-indol-3-yl-methyl, $R^2$ is hydrogen, X is $CH_2(CO)NH_2$; $R^5$ is hydrogen; and the configuration of the carbon to which $R^1$ is attached is R.

In another embodiment, the gonadotropin-releasing hormone is a hormone of formula I where $R^1$ is hydrogen, $R^2$ is hydrogen, X is $CH_2(CO)NH_2$; and $R^5$ is hydrogen.

In another embodiment, the gonadotropin-releasing hormone is a hormone of formula I where $R^1$ is 1H-1-benzyl-imidazol-4-yl-methyl, $R^2$ is hydrogen, X is ethyl; and $R^5$ is hydrogen.

In another embodiment, the gonadotropin-releasing hormone is a hormone of formula I where $R^1$ is 2-methylpropyl, $R^2$ is hydrogen, X is ethyl; and $R^5$ is hydrogen.

In yet another embodiment, any one of the previously described embodiments wherein X is $CH_2C(O)NH_2$ is provided.

In another embodiment, the gonadotropin-releasing hormone is a hormone of formula I where R1 is 2-naphthlymethyl, R2 is hydrogen, X is CH2(CO)NH2; and R5 is hydrogen.

In another embodiment, the gonadotropin-releasing hormone is a hormone of formula I where R1 is t-butoxymethyl, R2 is hydrogen, X is ethyl; R5 is hydrogen; and the configuration of the carbon to which R1 is attached is R.

In another embodiment, the gonadotropin-releasing hormone is a hormone of formula I where R1 is benzyl, R2 is hydrogen, X is CH2(CO)NH2; R5 is hydrogen; and the configuration of the carbon to which R1 is attached is R.

In another embodiment, the gonadotropin-releasing hormone is a hormone of formula I where R1 is t-butoxymethyl, R2 is hydrogen, X is HN(CO)NH2; and R5 is hydrogen.

In another embodiment, the gonadotropin-releasing hormone is a hormone of formula I where R1 is 1H-indol-3-yl-methyl, R2 is hydrogen, X is ethyl; and R5 is hydrogen.

In another embodiment, the gonadotropin-releasing hormone is a hormone of formula I where R1 is methyl, R2 is hydrogen, X is hydrogen; R5 is hydrogen; and the configuration of the carbon to which R1 is attached is R.

In another embodiment, the gonadotropin-releasing hormone is a hormone of formula I where R1 is 1H-indol-3-yl-methyl, R2 is hydrogen, X is ethyl; R5 is methyl; and the configuration of the carbon to which R1 is attached is R.

In another embodiment, the gonadotropin-releasing hormone is a hormone of formula I where R1 is methyl, R2 is hydrogen, X is CH2(CO)NH2; R5 is hydrogen; and the configuration of the carbon to which R1 is attached is R.

The gonadotropin-releasing hormones, such as those described in the formula above, used herein can be administered in the form of pharmaceutically acceptable non-toxic salts or complexes. The salts include acid addition salts such as, for example, hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

Additional examples of acceptable hormones for use in the methods described herein include, prostaglandins, progestogens, progesterones, angrogens, testosterones, estrogens, and estradiols, derivatives and analogs thereof, combinations thereof, and the like. In the methods described herein the hormone used to synchronize estrus can be altrenogest (MATRIX® from Intervet, Inc. Summit, N.J.). The hormone used to synchronize estrus (e.g., altrenogest or any other suitable progestin) can be administered to the gilt by feeding, for example, by mixing the hormone with the gilt's feed or applying the hormone to the gilt's feed. Methods for feeding altrenogest to gilts are well known in the art. For example, in one embodiment, a 0.22% altrenogest solution (or any other suitable concentration) can be used to administer 15 mg of altrenogest per gilt once daily for 14 days in the gilt's feed. In another embodiment, a 0.22% altrenogest solution (or any other suitable concentration) can be used to administer 20 mg of altrenogest per gilt once daily for 18 days in the gilt's feed. Any other suitable regimen for the administration of altrenogest or another hormone for synchronizing estrus (e.g., any other suitable progestin) can be used in accordance with the invention. The hormone for synchronizing estrus can be administered to the gilt by any suitable method known in the art, including by feeding.

The amount of the gonadotropin-releasing hormone effective for use in accordance with the methods and compositions described herein depends on many parameters, including the molecular weight of the gonadotropin-releasing hormone, its route of administration, and whether it is in its native form. As in described herein an "effective amount" of the hormone is an amount sufficient to synchronize ovulation or to synchronize the time of insemination in a gilt or a sow using the methods described herein.

The effective amount of the gonadotropin-releasing hormone to be administered to a gilt or a sow can range from about 100 ng to about 2000 µg, about 100 ng to about 1000 µg, about 100 ng to about 500 µg, about 1 µg to about 2000 µg, about 1 µg to about 500 µg, about 1 µg to about 100 µg, about 1 µg to about 50 µg, about 1 µg to about 10 µg, about 10 µg to about 2000 µg, about 10 µg to about 1000 µg, about 10 µg to about 500 µg, about 10 µg to about 100 µg, about 10 µg to about 50 µg, about 50 µg to about 2000 µg, about 50 µg to about 1000 µg, about 50 µg to about 500 µg, about 50 µg to about 300 µg, about 50 µg to about 200 µg, about 100 µg to about 200 µg, about 100 µg to about 300 µg, about 100 µg to about 500 µg, about 100 µg to about 1000 µg, about 200 µg to about 2000 µg, or about 0.05 mg to about 50 mg. In various illustrative aspects, the gonadotropin-releasing hormone can be administered to a gilt or a sow at a dose of about 1 µg, about 2 µg, about 5 µg, about 10 µg, 20 µg, about 50 µg, about 75 µg, about 100 µg, about 150 µg, about 180 µg, about 200 µg, about 225 µg, about 250 µg, about 300 µg, about 400 µg, about 500 µg, about 750 µg, about 1000 µg, about 1500 µg, or about 2000 µg of the gonadotropin-releasing hormone. The gonadotropin-releasing hormone can be administered in one or more doses.

Typically, the gonadotropin-releasing hormone is administered without any additional hormone to synchronize ovulation.

The gonadotropin-releasing hormone in the composition used for the methods described herein can be administered at a concentration of, for example, about 0.1 µg/mL, about 0.5 µg/mL, about 1 µg/mL, about 5 µg/mL, about 10 µg/mL, about 50 µg/mL to about 500 µg/mL, about 50 µg/mL to about 400 µg/mL, about 50 µg/mL to about 300 µg/mL, about 50 µg/mL to about 200 µg/mL, about 50 µg/mL to about 150 µg/mL, about 50 µg/mL to about 250 µg/mL, or about 100 µg/mL. In illustrative embodiments, the composition can be administered in various volumes including for example a dosage volume of 0.1 mL, 0.5 mL, 1 mL, 2 mL, 3 mL, 4 mL, or 5 mL. Any suitable volume for administration can be used, depending on, for example, the route of administration to the animal, the size of the animal to which the hormone is being administered, the species of the animal to which the hormone is being administered, and other factors known to those skilled in the art.

In any embodiment described herein, the gonadotropin-releasing hormone is administered in an amount effective to stimulate ovarian follicle ovulation and to synchronize ovulation according to the methods described herein. The dose of the gonadotropin-releasing hormone can be administered using a method selected from the group consisting of 1) use of a deposition catheter, 2) manual administration, 3) injection, or any other art recognized means for administering a pharmaceutical composition, for example, any other art recognized means for vaginally administering a pharmaceutical composition, such as a composition containing a hormone. In one embodiment, the gonadotropin-releasing hormone can be administered to more than one gilt or sow.

Examples of methods for effective gonadotropin-releasing hormone administration, other than vaginal administration, include parenteral administration to the gilt or sow, for example, subcutaneously, intramuscularly, intraperitoneally, intrathecally, or intravenously, or in combination with an acceptable carrier. Suitable means for parenteral administration include needle (including microneedle) injectors, needle-free injectors, and infusion techniques. The parenteral compositions for use in accordance with this invention can be in the form of a reconstitutable lyophilizate comprising one or more doses of the gonadotropin-releasing hormone composition. Examples of parenteral dosage forms include aqueous solutions of the gonadotropin-releasing hormone composition in well-known acceptable liquid carriers such as liquid alcohols, glycols (e.g., polyethylene glycols), glucose solutions (e.g., 5%), esters, amides, sterile water, buffered saline (including buffers like phosphate or acetate; e.g., isotonic saline).

In any embodiment described herein, the gonadotropin-releasing hormone composition for use in the methods described herein can be administered to the gilt or sow locally. Examples of local administration methods for use herein include, topical, intravaginal, and intrarectal. Examples of dosage forms for use in this embodiment include creams, ointments, gels, pastes, powders, lotions, transdermal patches, intrauterine devices, vaginal rings, and vaginal tablets. In one illustrative embodiment, the gonadotropin-releasing hormone composition is administered into the anterior vagina of the gilt or sow. The gonadotropin-releasing hormones may also be formulated in vaginal or rectal compositions such as suppositories, e.g., containing conventional suppository bases such as cocoa butter, carbowaxes, polyethylene glycols or other glycerides, all of which melt at body temperature, yet are solidified at room temperature.

The gonadotropin-releasing hormone may be administered to the gilt or sow by any useful procedures and any effective dose and suitable dosage form can be used, including oral dosage forms known in the art, such as pills, pellets, or capsules, and effective doses can be administered in standard or modified release dosage forms. Modified release dosage formulations include delayed, sustained, pulsed, controlled, targeted, and programmed release formulations.

The gonadotropin-releasing hormone compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In another illustrative aspect, the gonadotropin-releasing hormone for use in the methods described herein may be in the form of a kit. The kit can comprise a dose or multiple doses of a gonadotropin-releasing hormone as described herein. In this embodiment, the kit can further comprise an applicator for manual administration, a deposition catheter, and/or a syringe for application of the hormone composition to the gilt or sow. In yet another embodiment, the gonadotropin-releasing hormone is in a composition comprising a gel as described herein. In one illustrative embodiment, the kit may comprise the gonadotropin-releasing hormone and the gel separately for mixing before administration to the gilt or sow, or they can be together in one composition. In another embodiment, the kit may comprise the gonadotropin-releasing hormone and the gel admixed in a vessel for immediate administration.

In yet another embodiment, the kit contains instructions for use. The instructions may indicate that the insemination should be through one or more artificial inseminations. The instructions can also provide the timing for administration of the gonadotropin-releasing hormone and the hormone for synchronizing estrus to the gilt as described herein, and the timing for artificial insemination.

In yet another embodiment, an article of manufacture is provided. The article of manufacture can comprise any of the gonadotropin-releasing hormone compositions described herein for use in the methods described herein. The gonadotropin-releasing hormone composition can be in a primary container, for example, a glass vial, such as an amber glass vial with a rubber stopper and/or an aluminum tear-off seal. In another embodiment, the primary container can be plastic or aluminum, and the primary container can be sealed. In another embodiment, the primary container may be contained within a secondary container to further protect the composition from light. The secondary container can be, for example, cardboard.

Any of these embodiments also apply to the kit embodiments described above, and any of the gonadotropin-releasing hormone composition embodiments described herein can apply to the article of manufacture.

EXAMPLES

Example 1

Study Design and Treatments

All gilts were individually fed MATRIX® as a top-dress for 14 days at the recommended rate of 15 mg/gilt/day. Gilts were withdrawn from MATRIX® feeding (last top feed in the morning on Day 0) and allotted to treatments. Controls were treated with a 1.2% methylcellulose gel formulation without triptorelin at 96 hours following MATRIX® withdrawal (last top-dress). The remaining gilts received 200 mcg triptorelin, as the acetate, in a 1.2% methylcellulose gel formulation intravaginally at various times after MATRIX® withdrawal. The four treatments were: 1) vehicle gel (VG) treatment at 96 hours after MATRIX® withdrawal, 2) triptorelin gel (TG) treatment at 96 hours after MATRIX® withdrawal, 3) TG treatment at 120 hours after MATRIX® withdrawal and 4) TG treatment at 144 hours after MATRIX® withdrawal. All gilts were monitored for their estrous and ovulatory status as described below. Gilts included in replicate 1 were selected from terminal line commercial production gilts located in grow/finish barns. Sexual maturity, as indicated by one or more estrous periods, was not verified prior to the start of MATRIX® feeding. Gilts included in replicate 2 were selected from a maternal line gilt population. Sexual maturity was verified by at least one estrous period verified and recorded prior to starting MATRIX® feeding.

Test Substance

Triptorelin (pGlu-His-Trp-Ser-Tyr-D-Trp-Leu-Arg-Pro-Gly-NH$_2$) was supplied in the acetate form, from Bachem, Torrance, Calif. (Item H-4075 CGMP grade). Triptorelin gel (200 µg/2 mL) was formulated by Argenta (Auckland, NZ) in a gel composed of Methocel Premium A4000 (Dow Chemical), citrate buffer (pH 5.5), NaCl, methionine and EDTA (as potential stabilizers) and methyl and propyl parabens (as preservatives). Fifty-four milliliters of triptorelin gel (100 mcg triptorelin acetate/mL) was packaged in Amber Borosilicate Glass Serum Vials (610206-50) with a Gray Butyl Pharmaceutical Serum Vial Stopper (73828A-SS) with a Standard Aluminum Seal (SAS20NAT). The triptorelin gel vehicle contained the same formulation excipients as in triptorelin gel, except it did not contain triptorelin or the potential stabilizers, methionine and EDTA. MATRIX® was supplied as the US commercially available form.

Estrus Observation

For post-treatment estrus detection, gilts were housed in individual pens. Boars were housed in separate rooms, and/or at least 12 m away and downwind. To elicit signs of estrus, a mature boar was walked slowly in the alley in front of the gilts' crates, exposing each test gilt to visual, auditory and olfactory signals from the boar for up to 5 minutes. In keeping with standard practice at commercial farms, while the boar was near the front of the gilt's crate, estrus was tested by an experienced person applying back pressure to the midsection of the gilt combined with side rubbing. Estrus was confirmed when a gilt stood rigidly to the back pressure, with no vocalization and with some indication of an ear reflex.

For replicate one, estrus detection was performed on gilts once daily from Day 5 to Day 8. For replicate two, estrus detection was performed on gilts once daily from Day 0 to Day 8.

Ovulation Monitoring

The ovulatory status of all gilts was monitored by transrectal ultrasonography. For replicate one, ovulation was monitored two times on Day 5, then three times a day from Day 6 to Day 8. For replicate two, ovulation was monitored three times a day from Day 5 to Day 8. An Aloka 500 ultrasound machine with a 7.5 MHz linear array transducer attached to a fixed-angle PVC stabilizing rod to facilitate insertion into the rectum was used for this purpose. The transducer and PVC rod were coated with a gynecological lubricant and gently inserted into the rectum until the ovaries were visualized, one at a time. The diameters of the three largest follicles were recorded (to the nearest 0.1 mm) at each scanning. A gilt was declared to have ovulated when the number of large follicles (≥6.5 mm) fell to less than 3.

Administration

A single 2 mL dose of triptorelin gel or vehicle gel was deposited within approximately 1-2 cm posterior to the cervix with a catheter similar to those used for artificial insemination. The dose was delivered using a standard multi-dose applicator attached to the catheter. A new disposable sheath, which surrounds the catheter, was used for each gilt.

Statistical Analysis

Data were analyzed using the Mixed Models procedures of SAS. Models included main effects of time of treatment following the last feeding of MATRIX®, replicate, and treatment by replicate interaction. Differences between treatments were tested on least squares means estimates using the T test at $P<0.05$. Data for analysis were tested for assumptions of data normality.

Results

Five gilts in replicate 1 and three gilts in replicate 2 were removed from the data analysis for reasons not related to the treatment. Results are presented in FIGS. 1 and 2, with tabular data presented in Tables 1 and 2 for Replicates 1 and 2, respectively. More gilts in replicate 2 were detected in estrus following MATRIX® compared with replicate 1.

Replicate 1 was conducted in a finishing research facility with crossbred PIC C-22×line 337 terminal line females at a lower level of sexual maturity compared to PIC C-22 maternal line females, which were more sexually mature and were in a highly maintained environmental breeding facility in replicate 2. A lower percentage of gilts had displayed their first estrus before MATRIX® feeding in replicate 1 compared to replicate 2. Not only was replicate 2 conducted at a different location than replicate 1, but the sexual maturity was also greater for gilts in replicate 2, as evidenced by documented estrous cycles in all the gilts before initiation of MATRIX® feeding. In replicate 1, estrous cycles could not be reliably documented in all gilts before initiation of MATRIX® feeding.

Figure 3:
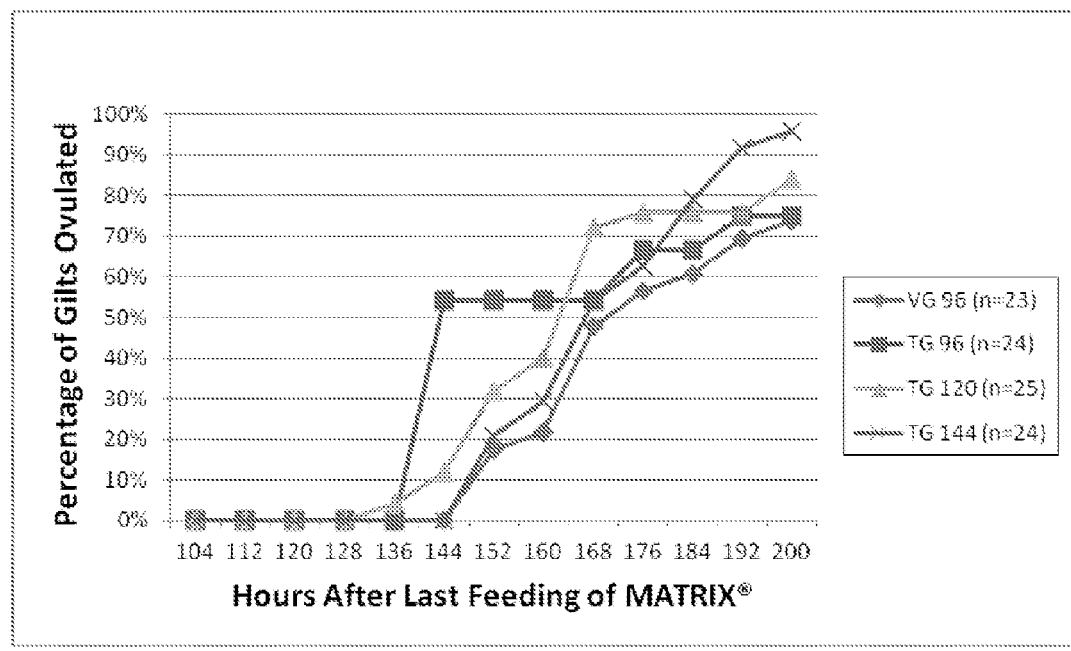
FIG. 3 shows the cumulative percentage of gilts, which ovulated after administration of vehicle gel at 96 hours (VG 96) or triptorelin gel containing 200 μg triptorelin at 96 hours (TG 96), 120 hours (TG 120) or 144 hours (TG 144) after last MATRIX® feeding in replicates 1 and 2 combined.

The interval from last MATRIX® feeding to ovulation was influenced by treatment and replicate. The interval from triptorelin gel treatment to ovulation is expected to peak at 40-48 hours following treatment. Therefore, the interval from MATRIX® to ovulation is expected to differ when triptorelin gel is administered at 96, 120 or 144 hours post-MATRIX®. This is shown in Table 4 and depicted in FIG. 3. The ovulatory peak occurred at 48 hours following treatment for each group. However, the peak was at 144, 168 and 192 hours post-MATRIX® for 96, 120 and 140 hours treatment groups, respectively. The vehicle treated group did not exhibit a synchronous ovulatory peak, but rather a steady increase in percent ovulated that never attained the same level as observed for triptorelin gel treated gilts.

Figure 2:
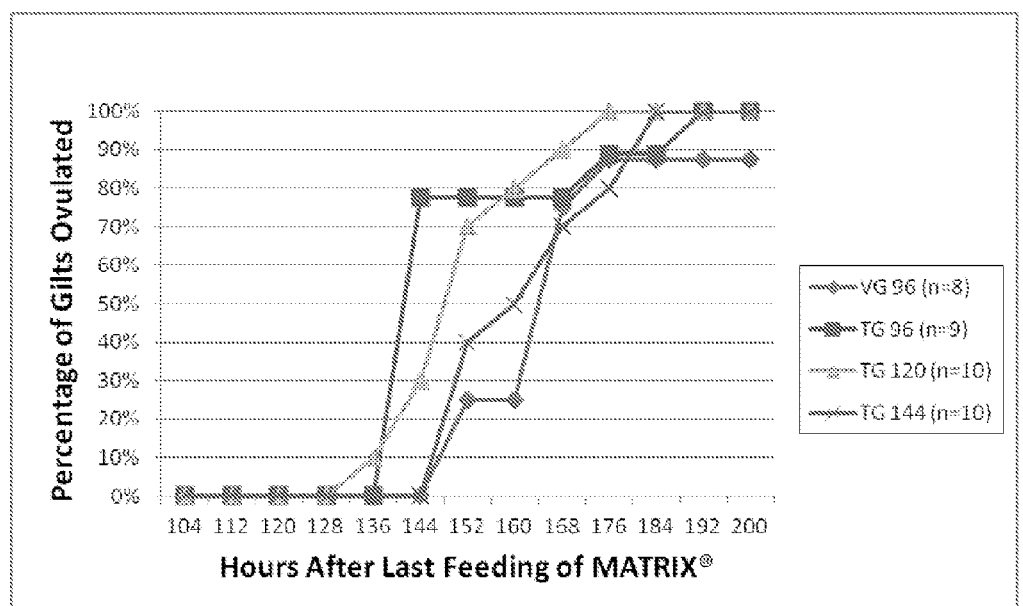
FIG. 2 shows the cumulative percentage of gilts, which ovulated after administration of vehicle gel at 96 hours (VG 96) or triptorelin gel containing 200 μg triptorelin at 96 hours (TG 96), 120 hours (TG 120) or 144 hours (TG 144) after last MATRIX® feeding in replicate 2.

The effect of replicate or perhaps more important the impact of sexual maturity is shown by comparison of Table 1 and Table 2. The gilts presented in Table 2 were confirmed to be sexually mature, whereas those in replicate or Table 1 were not. The differences can be seen in FIGS. 1 and 2. The sexually mature gilts (FIG. 2) demonstrated a higher ovulatory response at 48 hours following triptorelin gel treatment for each of the three treatment times. For example, 90% for replicate 2 compared with 60% for replicate 1 in the TG 120 treatment time. Even though the level of sexual maturity differed between these two groups of gilts, consistent trends are apparent when comparing FIG. 1 with FIG. 2 and the data presented in FIG. 3. The time of ovulation curves for vehicle control and triptorelin gel gilts treated at 144 hours are nearly identical, regardless of whether immature (FIG. 1) or mature (FIG. 2) and the combined plot in FIG. 3 suggests that treatment with triptorelin gel at 144 hours did not effectively synchronize ovulation. The 144 hour treatment time is apparently after the endogenous release of LH in many of the gilts and thus, too late to induce a synchronized ovulation. However, it is interesting to note that treatment at 144 hours did advance and synchronize ovulation in the immature gilts (FIG. 1) between 40 and 48 hours post-triptorelin gel, whereas 100% of the gilts had already ovulated by 40 hours in the sexually mature gilts (FIG. 2). These data suggest that a different time of treatment may be advised for sexually immature as compared with mature gilts.

Triptorelin gel treatment at either 96 or 120 hours did advance and produce a more synchronous ovulation than vehicle control treated gilts or gilts treated at 144 hours. The proportion of gilts ovulating within 48 hours and the synchrony of ovulation was greater for gilts treated at 120 hours (72%) compared with gilts treated at 96 hours (54.2%) (Table 4). For sexually mature gilts (FIG. 2 and Table 2), the difference was more pronounced with 90.0% and 77.8% ovulating within 48 hours for TG 120 and TG 96, respectively. These data demonstrate that 120 hours following the last MATRIX® feeding is the more effective time for treatment.

TABLE 1

Cumulative percentage of gilts ovulating at various time intervals following the last feeding of MATRIX ® and VG or TG treatment in replicate 1.

| | VG 96 (n = 15) | | TG 96 (n = 15) | | TG 120 (n = 15) | | TG 144 (n = 14) | |
|---|---|---|---|---|---|---|---|---|
| Hours Post-MATRIX | Hours Post-VG | Percent Gilts Ovulated | Hours Post-TG | Percent Gilts Ovulated | Hours Post-TG | Percent Gilts Ovulated | Hours Post-TG | Percent Gilts Ovulated |
| 128 | 32 | 0.0% | 32 | 0.0% | 8 | 0.0% | −16 | 0.0% |
| 136 | 40 | 0.0% | 40 | 0.0% | 16 | 0.0% | −8 | 0.0% |
| 144 | 48 | 0.0% | 48 | 40.0% | 24 | 0.0% | 0 | 0.0% |
| 152 | 56 | 13.3% | 56 | 40.0% | 32 | 6.7% | 8 | 7.1% |
| 160 | 64 | 20.0% | 64 | 40.0% | 40 | 13.3% | 16 | 14.3% |
| 168 | 72 | 33.3% | 72 | 40.0% | 48 | 60.0% | 24 | 42.9% |
| 176 | 80 | 40.0% | 80 | 53.3% | 56 | 60.0% | 32 | 50.0% |
| 184 | 88 | 46.7% | 88 | 53.3% | 64 | 60.0% | 40 | 64.3% |
| 192 | 96 | 60.0% | 96 | 60.0% | 72 | 60.0% | 48 | 85.7% |
| 200 | 104 | 66.7% | 104 | 60.0% | 80 | 73.3% | 56 | 92.9% |

TABLE 2

Cumulative percentage of gilts ovulating at various time intervals following the last feeding of MATRIX ® and VG or TG treatment in replicate 2.

| | VG 96 (n = 8) | | TG 96 (n = 9) | | TG 120 (n = 10) | | TG 144 (n = 10) | |
|---|---|---|---|---|---|---|---|---|
| Hours Post-MATRIX | Hours Post-VG | Percent Gilts Ovulated | Hours Post-TG | Percent Gilts Ovulated | Hours Post-TG | Percent Gilts Ovulated | Hours Post-TG | Percent Gilts Ovulated |
| 128 | 32 | 0.0% | 32 | 0.0% | 8 | 0.0% | −16 | 0.0% |
| 136 | 40 | 0.0% | 40 | 0.0% | 16 | 10.0% | −8 | 0.0% |
| 144 | 48 | 0.0% | 48 | 77.8% | 24 | 30.0% | 0 | 0.0% |
| 152 | 56 | 25.0% | 56 | 77.8% | 32 | 70.0% | 8 | 40.0% |
| 160 | 64 | 25.0% | 64 | 77.8% | 40 | 80.0% | 16 | 50.0% |
| 168 | 72 | 75.0% | 72 | 77.8% | 48 | 90.0% | 24 | 70.0% |
| 176 | 80 | 87.5% | 80 | 88.9% | 56 | 100.0% | 32 | 80.0% |
| 184 | 88 | 87.5% | 88 | 88.9% | 64 | 100.0% | 40 | 100.0% |
| 192 | 96 | 87.5% | 96 | 100.0% | 72 | 100.0% | 48 | 100.0% |
| 200 | 104 | 87.5% | 104 | 100.0% | 80 | 100.0% | 56 | 100.0% |

TABLE 3

Least squares means for response variables measured for post-MATRIX ® gilts assigned to receive VG at 96 hours after MATRIX ® withdrawal, or TG at 96, 120, or 144 hours after last MATRIX ® feeding in replicates 1 and 2 combined.

|  | VG 96 | TG 96 | TG 120 | TG 144 | SEM | P |
|---|---|---|---|---|---|---|
| N | 23 | 24 | 25 | 24 |  |  |
| Estrous Expression (%) | 79.8 | 63.1 | 79.9 | 78.2 | 8.6 | 0.45 |
| Interval from MATRIX ® withdrawal to Estrus (h) | 147.7 | 143.8 | 143.3 | 146.5 | 4.8 | 0.90 |
| Interval from MATRIX ® Withdrawal to Ovulation (h) | $169.4^x$ | $154.7^y$ | $162.8^{xy}$ | $171.1^x$ | 3.4 | 0.0049 |
| MOV136 (%) | 0.4 | 0.3 | 4.3 | 0.2 | 2.1 | 0.43 |
| MOV144 (%) | $2.6^x$ | $56.3^y$ | $13.7^x$ | $1.4^x$ | 6.1 | 0.0001 |
| MOV152 (%) | $23.1^x$ | $58.8^y$ | $35.7^x$ | $23.9^x$ | 8.5 | 0.0117 |
| MOV160 (%) | $27.4^x$ | $58.8^y$ | $43.7^{xy}$ | $32.3^x$ | 9.1 | 0.0745 |
| MOV168 (%) | 53.0 | 58.4 | 75.4 | 57.0 | 9.7 | 0.36 |
| MOV176 (%) | 62.3 | 71.4 | 79.8 | 65.7 | 9.1 | 0.54 |
| MOV184 (%) | 66.7 | 71.4 | 79.8 | 82.3 | 8.6 | 0.54 |
| MOV192 (%) | 74.2 | 78.9 | 79.1 | 94.2 | 8.0 | 0.31 |
| MOV200 (%) | 77.3 | 80.7 | 86.3 | 97.7 | 7.4 | 0.23 |

Replicate is significant in every one of these except MOV 136.

TABLE 4

Cumulative percentage of gilts ovulating at various time intervals following the last feeding of MATRIX ® and VG or TG treatment in replicates 1 and 2 combined.

| | VG 96 (n = 23) | | TG 96 (n = 24) | | TG 120 (n = 25) | | TG 144 (n = 24) | |
|---|---|---|---|---|---|---|---|---|
| Hours Post-MATRIX | Hours Post-VG | Percent Gilts Ovulated | Hours Post-TG | Percent Gilts Ovulated | Hours Post-TG | Percent Gilts Ovulated | Hours Post-TG | Percent Gilts Ovulated |
| 128 | 32 | 0% | 32 | 0% | 8 | 0% | −16 | 0% |
| 136 | 40 | 0% | 40 | 0% | 16 | 4.0% | −8 | 0% |
| 144 | 48 | 0% | 48 | 54.2% | 24 | 12.0% | 0 | 0% |
| 152 | 56 | 17.4% | 56 | 54.2% | 32 | 32.0% | 8 | 20.8% |
| 160 | 64 | 21.7% | 64 | 54.2% | 40 | 40.0% | 16 | 29.2% |
| 168 | 72 | 47.8% | 72 | 54.2% | 48 | 72.0% | 24 | 54.2% |
| 176 | 80 | 56.5% | 80 | 66.7% | 56 | 76.0% | 32 | 62.5% |
| 184 | 88 | 60.9% | 88 | 66.7% | 64 | 76.0% | 40 | 79.2% |
| 192 | 96 | 69.6% | 96 | 75.0% | 72 | 76.0% | 48 | 91.7% |
| 200 | 104 | 73.9% | 104 | 75.0% | 80 | 84.0% | 56 | 95.8% |

Example 2

Study Design and Treatments

Two hundred ninety-seven (297) gilts were fed MATRIX® as a top-dress for 14 days at the recommended rate of 15 mg/gilt/day. The last feeding of MATRIX® was at 5:30 AM (Day 0). Approximately one hundred gilts were allocated to each of the following treatments:
1. Group 1, Controls (n=100); MATRIX® treated, but not OvuGel™ treated, inseminated daily during estrus, as is normally practiced (average of 1.9 inseminations per gilt).
2. Group 2 (n=98); OvuGel™ treated at 6:30 am (+/−1 hr) on Day 5 and inseminated at 2 to 11 hours post-OvuGel™ treatment on Day 5 if expressing estrus. All gilts inseminated once on Day 6, 26 hours (+/−2.5 hrs) post-OvuGel™ treatment, regardless of estrus status.
3. Group 3 (n=99); OvuGel™ treated at 6:30 am (+/−1 hr) on Day 5 and inseminated once at 2.5 to 9.5 hours post-OvuGel™ treatment on Day 5 and again on Day 6, 26.5 hours (+/−3 hrs) post-OvuGel™ treatment, without regard to estrus on either day.

Test Substance

Triptorelin (pGlu-His-Trp-Ser-Tyr-D-Trp-Leu-Arg-Pro-Gly-NH$_2$) was supplied in the acetate form, from Bachem, Torrance, Calif. (Item H-4075 CGMP grade). Triptorelin gel (200 mcg/2 mL) was formulated by DPT Laboratories (San Antonio, Tex.) in a gel composed of Methocel Premium A4000 (Dow Chemical) and other inactive formulation excipients. Fifty-four milliliters of triptorelin gel (100 mcg triptorelin acetate/mL) was packaged in Amber Borosilicate Glass Serum Vials (610206-50) with a Gray Butyl Pharmaceutical Serum Vial Stopper (73828A-SS) with a Standard Aluminum Seal (SAS20NAT).

Estrus Observation

Gilts were housed in individual pens. Boars were housed at least 12 m away and downwind. To determine onset and duration of estrus, gilts were observed for estrus daily from 4 days until 8 days after last feeding of MATRIX® or until the end of estrus was confirmed, whichever came first. To facilitate detection of estrus, a mature boar was walked slowly in the alley in front of the gilt's pen, exposing each gilt to visual, auditory and olfactory signals from the boar for up to 5 minutes. While the boar was near the front of the gilt's pen, estrus was tested by an experienced person applying back pressure to the midsection of the gilt combined with side rubbing. Estrus was confirmed when a gilt stood rigidly to the back pressure, with no vocalization and with some indication of an ear reflex.

Drug Administration

A single 2 mL dose of OvuGel™ was deposited within approximately 1-2 cm posterior to the cervix with a catheter similar to those used for artificial insemination. The dose was delivered using a standard multi-dose applicator attached to the catheter. A new disposable sheath, which surrounds the catheter, was used for each gilt.

Statistical Analysis

Data were subjected to analysis of variance using the PROC MIX procedure of SAS (version 9.2) to determine the main effect of treatment, replicate and treatment by replicate interaction on farrowing rate and litter size. Differences between treatments were tested on least squares means estimates using the T test at P<0.05.

Results

Two hundred ninety-seven (297) gilts were allotted to treatment groups (Group 1: 100, Group 2: 98, Group 3: 99). One Control gilt was removed from the study due to an injury before post-weaning estrus status was completed on Day 8 and was therefore removed from the final data set. Tables 5 through 8 present the least square means and statistical analysis for all gilts. There was a time difference between replicates when gilts were inseminated on Day 5. Replicate 1 gilts were inseminated on Day 5, 7.5 to 11 hours post-OvuGel™ treatment. Gilts inseminated on Day 5 in replicate 2 were bred 2.25 to 4.5 hours after OvuGel™ administration. Because of this difference, the least square means and statistical analysis for pregnancy, farrowing and born alive data are presented by replicate in Table 9. There were no treatment by replicate interactions (P>0.60) for any of these variables and only a tendency (P<0.09) for a replicate effect for farrowing rate. Raw data and unadjusted means are shown in Tables 10 through 13. As shown in Table 5, the percentage of gilts pregnant at 30 days post-insemination was the same for all treatments (P>0.94), as was the percentage of gilts that farrowed (P>0.79). Total piglets born per litter (P>0.74) and piglets born live per litter (P>0.44) was not different among treatments. Nor was there a treatment difference in the piglet index (P>0.80). Table 6 presents the least squares means for the expression of estrus post-MATRIX®. There was no difference due to treatment in the percentage of gilts first expressing estrus on Day 5 (P>0.35) or on Day 6 (P>0.15).

The pregnancy rate based on when gilts first expressed estrus is shown in Table 7. Control and Treatment 2 gilts that expressed estrus on Day 5 had a greater percentage pregnant at 30 days than did the Treatment 3 gilts (P<0.04). There was a trend (P=0.10) for a higher percentage of pregnancy among the Control gilts that expressed estrus on Day 6 compared to gilts on Treatments 2 and 3. However, when comparing overall pregnancy rate for all gilts expressing estrus there was no difference between treatments (P>0.94). Table 8 shows the farrowing rate of gilts based on when they first expressed estrus. The only difference among treatments is for gilts that expressed estrus on Day 5. Those gilts in Treatment 2 had a greater farrowing rate (P<0.03) than the Control or Treatment 3 gilts (94.1% vs. 76.0 and 66.7%, respectively).

The results of this study demonstrate the farrowing rate and litter size in gilts inseminated at a fixed-time following MATRIX® and OvuGel™ treatment are not different from gilts inseminated at detected estrus following MATRIX® treatment. These data are also consistent with previous trials in weaned sows in which 30 to 60% of sows or gilts that did not express estrus conceived following the fixed-time insemination. The timing of insemination on Day 5 and 6 is consistent with the time of ovulation data observed in the Example 1 trials.

This protocol was conducted at two separate locations with different results. The gilts at the first site all had expressed estrus a minimum of three times and many of them had experienced 4 or 5 estrus cycles prior to starting on MATRIX®. The gilts at the second site only had a single confirmed estrus before starting the MATRIX®. The farrowing rate for control gilts was higher than for OvuGel™ treated gilts at the other location. The age difference in gilts could have contributed to the difference in results. An average of 30.1% of the older gilts at the first site first expressed estrus on Day 5 post-MATRIX®. Only 7.4% of the younger gilts at the second site showed estrus on Day 5. By Day 7 post-MATRIX®, only 16.2% of the older Control gilts and 2% of the older gilts that received OvuGel™ were expressing estrus for the first time. At the second site, among the younger gilts there were still 41.3% of the Controls and 18.3% of the OvuGel™ gilts that expressed estrus for the first time on Day 7.

Results at the first site, with sexually mature gilts, demonstrate that OvuGel™ given at ~120 hours after the last feeding of MATRIX® and followed with either a conditional insemination on Day 5 paired with a fixed-time insemination on Day 6 or a double fixed-time insemination on Day 5 and Day 6, results in a similar farrowing rate and litter size compared to gilts inseminated following detection of estrus.

TABLE 5

Gilt Performance

|  | Control | Group 2 | Group 3 | SEM | P < |
|---|---|---|---|---|---|
| No. Gilts | 99 | 98 | 99 | — | — |
| Pregnant at 30 days, % | 71.7 | 73.2 | 73.7 | 4.51 | 0.9469 |
| Percent Farrowed of Allotted | 64.6 | 69.1 | 65.7 | 4.78 | 0.7906 |
| Piglets Born Live per Litter | 13.2 | 12.8 | 12.5 | 0.30 | 0.4479 |
| Total Piglets Born per Litter | 13.7 | 13.5 | 13.4 | 0.32 | 0.7416 |
| Piglet Index | 850 | 883 | 819 | 73.0 | 0.8008 |

TABLE 6

Expression of Estrus post-MATRIX ®

|  | Control | Group 2 | Group 3 | SEM | P < |
|---|---|---|---|---|---|
| No. Gilts | 99 | 98 | 99 | — | — |
| 1st Expression of Estrus on Day 5, % | 25.3 | 34.7 | 30.3 | 4.62 | 0.3526 |
| 1st Expression of Estrus on Day 6, % | 35.4 | 44.9 | 48.5 | 4.98 | 0.1565 |
| 1st Expression of Estrus on Day 7, % | 16.2 | 2.0 | — | — | — |

TABLE 6-continued

Expression of Estrus post-MATRIX ®

|  | Control | Group 2 | Group 3 | SEM | P < |
|---|---|---|---|---|---|
| 1st Expression of Estrus on Day 8, % | 6.1 | — | — | — | — |
| Percent not confirmed in Estrus by Day 8 | 17.2 | 18.4 | 21.2 | 3.96 | 0.7581 |

Estrus checks were not reliable on gilts that received OvuGel ™ (treatments 2 and 3) after Day 6. Estrus checks continued on Control gilts until all gilts expressed estrus and were mated (9 to 32 days post-MATRIX ®).

TABLE 7

Pregnancy Rate Based on When Gilts Expressed Estrus

|  | Control | Group 2 | Group 3 | SEM | P < |
|---|---|---|---|---|---|
| Pregnant (%) - Day 5 Estrus | 92.0 | 97.1 | 76.7 | 5.44 | 0.0313 |
| Pregnant (%) - Day 6 Estrus | 91.4 | 72.1 | 79.2 | 5.88 | 0.1029 |
| Pregnant (%) - Day 7 Estrus | 81.3 | 50.0 | — | — | — |
| Pregnant (%) - Day 8 Estrus | 50.0 | — | — | — | — |
| Pregnant (%) - No Estrus or Estrus after Day 8 | — | 33.3 | 57.1 | 11.25 | 0.1422 |

Group 2 gilts expressing estrus on Day 5 post-MATRIX ® received 2 inseminations, Day 5 and Day 6. All other Group 2 gilts only received a single insemination on Day 6. All Group 3 gilts received an insemination on Day 5 and on Day 6, regardless of when estrus was expressed.

TABLE 8

Farrowing Rate Based on When Gilts Expressed Estrus

|  | Control | Group 2 | Group 3 | SEM | P < |
|---|---|---|---|---|---|
| Farrow (%) - Day 5 Estrus | 76.0 | 94.1 | 66.7 | 7.19 | 0.0217 |
| Farrow (%) - Day 6 Estrus | 85.7 | 67.4 | 70.8 | 6.62 | 0.1605 |
| Farrow (%) - Day 7 Estrus | 81.3 | 50.0 | — | — | — |
| Farrow (%) - Day 8 Estrus | 33.3 | — | — | — | — |
| Farrow (%) - No Estrus or Estrus after Day 8 | — | 27.8 | 52.4 | 11.17 | 0.1243 |

Group 2 gilts expressing estrus on Day 5 post-MATRIX ® received 2 inseminations, Day 5 and Day 6. All other Group 2 gilts only received a single insemination on Day 6. All Group 3 gilts received an insemination on Day 5 and on Day 6, regardless of when estrus was expressed.

TABLE 9

Performance by Replicate

|  | Replicate 1 | | | Replicate 2 | | | | Trt, | Rep, | Trt* Rep |
|---|---|---|---|---|---|---|---|---|---|---|
|  | Control | Grp 2 | Grp 3 | Control | Grp 2 | Grp 3 | SEM | P < | P < | P < |
| Pregnant at 30 days, % | 74.5 | 76.5 | 76.0 | 68.8 | 69.6 | 71.4 | 6.39 | 0.95 | 0.28 | 0.99 |
| Percent Farrowed of Allotted | 70.6 | 70.6 | 72.0 | 58.3 | 67.4 | 59.2 | 6.76 | 0.79 | 0.09 | 0.73 |
| Piglets Born Live per Litter | 12.8 | 12.8 | 12.5 | 13.6 | 12.9 | 12.5 | 0.43 | 0.26 | 0.39 | 0.62 |

Group 2 gilts expressing estrus on Day5 post-MATRIX ® received 2 inseminations, Day 5 and Day 6. All other Group 2 gilts only received a single insemination on Day 6. All Group 3 gilts received an insemination on Day 5 and on Day 6, regardless of when estrus was expressed. Group 2 and 3 gilts in replicate 1 that were bred on Day 5 were inseminated 9.5 to 11 hours post-OvuGel ™ treatment. Replicate 2 gilts in Groups 2 and 3 were inseminated on Day 5, 2.25 to 4.5 hours post-OvuGel ™ administration.

TABLE 10

Performance - Unadjusted Means

|  | Control | Group 2 | Group 3 |
|---|---|---|---|
| No. Gilts | 99 | 98 | 99 |
| Pregnant at 30 days, % | 71.7 | 73.2 | 73.7 |
| Percent Farrowed of Allotted | 64.6 | 69.1 | 65.7 |
| Piglets Born Live per Litter | 13.2 | 12.8 | 12.5 |
| Total Piglets Born per Litter | 13.7 | 13.5 | 13.4 |
| Piglet Index | 851 | 885 | 819 |

TABLE 11

Expression of Estrus post-MATRIX ® - Unadjusted Means

|  | Control | Group 2 | Group 3 |
|---|---|---|---|
| No. Gilts | 99 | 98 | 99 |
| 1st Expression of Estrus on Day 5, % | 25.3 | 34.7 | 30.3 |
| 1st Expression of Estrus on Day 6, % | 35.4 | 44.9 | 48.5 |
| 1st Expression of Estrus on Day 7, % | 16.2 | 2.0 | — |
| 1st Expression of Estrus on Day 8, % | 6.1 | — | — |
| Percent not confirmed in Estrus by Day 8 | 17.2 | 18.4 | 21.2 |

Estrus checks were not reliable on gilts that received OvuGel ™ (treatments 2 and 3) after Day 6. Estrus checks continued on Control gilts until all gilts expressed estrus and were mated (9 to 32 days post-MATRIX ®).

TABLE 12

Pregnancy Rate Based on When Gilts Expressed Estrus - Unadjusted Means

|  | Control | Group 2 | Group 3 |
|---|---|---|---|
| Pregnant (%) - Day 5 Estrus | 92.0 | 97.1 | 76.7 |
| Pregnant (%) - Day 6 Estrus | 91.4 | 72.1 | 79.2 |
| Pregnant (%) - Day 7 Estrus | 81.3 | 50.0 | — |
| Pregnant (%) - Day 8 Estrus | 50.0 | — | — |
| Pregnant (%) - No Estrus or Estrus after Day 8 | — | 33.3 | 57.1 |

Group 2 gilts expressing estrus on Day 5 post-MATRIX ® received 2 inseminations, Day 5 and Day 6. All other Group 2 gilts only received a single insemination on Day 6. All Group 3 gilts received an insemination on Day 5 and on Day 6, regardless of when estrus was expressed.

TABLE 13

Farrowing Rate Based on When Gilts Expressed Estrus - Unadjusted Means

| | Control | Group 2 | Group 3 |
|---|---|---|---|
| Farrow (%) - Day 5 Estrus | 76.0 | 94.1 | 66.7 |
| Farrow (%) - Day 6 Estrus | 85.7 | 67.4 | 70.8 |
| Farrow (%) - Day 7 Estrus | 81.3 | 50.0 | — |
| Farrow (%) - Day 8 Estrus | 33.3 | — | — |
| Farrow (%) - No Estrus or Estrus after Day 8 | — | 27.8 | 52.4 |

Group 2 gilts expressing estrus on Day 5 post-MATRIX ® received 2 inseminations, Day 5 and Day 6. All other Group 2 gilts only received a single insemination on Day 6. All Group 3 gilts received an insemination on Day 5 and on Day 6, regardless of when estrus was expressed.

Example 3

Study Design and Treatments

Three hundred twelve (312) gilts were fed MATRIX® as a top-dress for 14 days at the recommended rate of 15 mg/gilt/day. The last feeding of MATRIX® was at 6:30 AM (Day 0). One hundred four gilts were allocated to each of the following treatments:

1. Group 1, Controls (n=104); MATRIX® treated, but not OvuGel™ treated, inseminated daily during estrus, as is normally practiced at the site (average of 1.8 inseminations per gilt).
2. Group 2 (n=104); OvuGel™ treated at 7:00 am (+/−1.5 hours) on Day 5 and inseminated at 2 to 4 hours post-OvuGel™ treatment on Day 5 if expressing estrus. All gilts inseminated once on Day 6, 26 hours (+/−2 hrs) post-OvuGel™ treatment, regardless of estrus status.
3. Group 3 (n=104); OvuGel™ treated at 7:00 am (+/−1.5 hours) on Day 5 and inseminated once at 2 to 4 hours post-OvuGel™ treatment on Day 5 and again on Day 6, 26 hours (+/−2 hrs) post-OvuGel™ treatment, without regard to estrus on either day.

Test Substance

Triptorelin (pGlu-His-Trp-Ser-Tyr-D-Trp-Leu-Arg-Pro-Gly-NH$_2$) was supplied in the acetate form, from Bachem, Torrance, Calif. (Item H-4075 CGMP grade). Triptorelin gel (200 mcg/2 mL) was formulated by DPT Laboratories (San Antonio, Tex.) in a gel composed of Methocel Premium A4000 (Dow Chemical) and other inactive formulation excipients. Fifty-four milliliters of triptorelin gel (100 mcg triptorelin acetate/mL) was packaged in Amber Borosilicate Glass Serum Vials (610206-50) with a Gray Butyl Pharmaceutical Serum Vial Stopper (73828A-SS) with a Standard Aluminum Seal (SAS20NAT).

Estrus Observation

Gilts were housed in individual pens. Boars were housed at least 12 m away and downwind. To determine onset and duration of estrus, gilts were observed for estrus daily from 4 days until 8 days after last feeding of MATRIX® or until the end of estrus was confirmed, whichever came first. To facilitate detection of estrus, a mature boar was walked slowly in the alley in front of the gilt's pen, exposing each gilt to visual, auditory and olfactory signals from the boar for up to 5 minutes. While the boar was near the front of the gilt's pen, estrus was tested by an experienced person applying back pressure to the midsection of the gilt combined with side rubbing. Estrus was confirmed when a gilt stood rigidly to the back pressure, with no vocalization and with some indication of an ear reflex.

Drug Administration

A single 2 mL dose of OvuGel™ was deposited within approximately 1-2 cm posterior to the cervix with a catheter similar to those used for artificial insemination. The dose was delivered using a standard multi-dose applicator attached to the catheter. A new disposable sheath, which surrounds the catheter, was used for each gilt.

Statistical Analysis

Data were subjected to analysis of variance using the PROC MIX procedure of SAS (version 9.2) to determine the main effect of treatment, replicate, site, treatment by site, and treatment by replicate interaction on farrowing rate and litter size. Differences between treatments were tested on least squares means estimates using the T test at P<0.05.

Results

Three hundred twelve (312) gilts were allotted to treatment groups (Group 1: 104, Group 2: 104, Group 3: 104). Since these data were collected at two different sites within the farm by two different crews, the pregnancy, farrowing, and litter size data were analyzed for a site effect and site by treatment interactions. There was not a site effect for number of piglets born alive (P>0.94), pregnant at 30 days (P>0.77) or farrowing (P>0.68) rate. Nor was there a treatment by site interaction (P>0.46) for any of these variables. Thus, the data presented in Tables 14 through 21 shows the combined results from both sites. Tables 14 through 17 present the least squares means and statistical analysis for all gilts. Raw data and unadjusted means are shown in Tables 18 through 21.

The percentage of gilts pregnant at 30 days in Table 14 was greater (P<0.02) for the Control group (91.3%) than for Group 2 or 3 (76.9 and 82.7%, respectively). The Control gilts also had a higher (P<0.01) farrowing rate compared to the gilts in Groups 2 and 3 (90.1%, 72.8%, and 80.8%, respectively). The average number of piglets born live per litter (P>0.22) and total piglets born per litter (P>0.28) was not different among the groups. Piglet index was higher (P<0.02) for the gilts in the Control group (989) compared to the gilts in Group 2 (773) or Group 3 (822).

Table 15 presents the least squares means for the expression of estrus post-MATRIX®. There was no difference among treatments for the percentage of gilts that expressed estrus on Days 5 and 6 post-MATRIX® (P>0.53), but the Control gilts had a higher percentage (P<0.0001) that expressed estrus for the first time on Day 7 (41.3%) than did Groups 2 and 3 (16.3 and 20.2%, respectively). The OvuGel™ treated gilts (Groups 2 and 3) had a greater percentage (P<0.0001) that did not express estrus by Day 8 post-MATRIX® (26.0 and 23.1%, respectively) than did the Control group (2.9%).

The pregnancy rate based on when gilts first expressed estrus is shown in Table 16. There was no difference in pregnancy rate among treatments for gilts that first expressed estrus on Days 5 and 6 (P>0.16). Control gilts that expressed estrus on Day 7 had a greater (P<0.003) percentage pregnant at 30 days (97.7%) than did the Group 2 gilts (64.7%).

Table 17 shows the farrowing rate of gilts based on when they first expressed estrus. Control gilts that expressed estrus on Day 7 had a greater (P<0.003) percentage that farrowed (97.7%) than did the Group 2 gilts (64.7%). OvuGel™ gilts in Groups 2 and 3 that did not express estrus had a farrowing rate of approximately 78% (40 farrowed out of 51 not expressing estrus).

Results at this farm, demonstrate that OvuGel™ given at ~120 hours after the last feeding of MATRIX® (Day 0) and followed with either an estrus dependent conditional insemination on Day 5 paired with a fixed-time insemination on Day 6 or a double fixed-time insemination on Day 5 and Day 6 results in similar litter size compared to gilts inseminated daily during estrus.

TABLE 14

Gilt Performance

|  | Control | Group 2 | Group 3 | SEM | P < |
|---|---|---|---|---|---|
| No. Gilts | 104 | 104 | 104 | — | — |
| Pregnant at 30 days, % | 91.3 | 76.9 | 82.7 | 3.55 | 0.0184 |
| Percent Farrowed of Allotted | 90.1 | 72.8 | 80.8 | 3.76 | 0.0069 |
| Piglets Born Live per Litter | 10.9 | 10.6 | 10.2 | 0.31 | 0.2234 |
| Total Piglets Born per Litter | 12.1 | 11.5 | 11.3 | 0.35 | 0.2840 |
| Piglet Index | 989 | 773 | 822 | 51.33 | 0.0160 |

Includes only pregnancy and farrowing data for gilts bred within 8 days post-MATRIX®.

TABLE 15

Expression of Estrus post-MATRIX®

|  | Control | Group 2 | Group 3 | SEM | P < |
|---|---|---|---|---|---|
| No. Gilts | 104 | 104 | 104 | — | — |
| 1$^{st}$ Expression of Estrus on Day 5, % | 7.7 | 6.7 | 7.7 | 2.57 | 0.9543 |
| 1$^{st}$ Expression of Estrus on Day 6, % | 40.4 | 48.1 | 44.2 | 4.88 | 0.5370 |
| 1$^{st}$ Expression of Estrus on Day 7, % | 41.3 | 16.3 | 20.2 | 4.15 | 0.0001 |
| 1$^{st}$ Expression of Estrus on Day 8, % | 6.7 | 1.9 | 4.8 | 1.98 | 0.2426 |
| 1$^{st}$ Expression of Estrus on Day 9, % | 1.0 | — | — | — | — |
| Percent not expressing Estrus | 2.9 | 26.0 | 23.1 | 3.37 | 0.0001 |

TABLE 16

Pregnancy Rate Based on When Gilts Expressed Estrus

|  | Control | Group 2 | Group 3 | SEM | P < |
|---|---|---|---|---|---|
| Pregnant (%) - Day 5 Estrus | 100 | 100 | 87.5 | 12.50 | 0.3916 |
| Pregnant (%) - Day 6 Estrus | 95.2 | 84.0 | 82.6 | 4.74 | 0.1600 |
| Pregnant (%) - Day 7 Estrus | 97.7 | 64.7 | 85.7 | 7.37 | 0.0023 |
| Pregnant (%) - Day 8 Estrus | 71.4 | 0 | 40.0 | 21.47 | 0.1982 |
| Pregnant (%) - Day 9 Estrus | 100 | — | — | — | — |
| Pregnant (%) - No Estrus | 0 | 74.1 | 87.5 | 7.75 | 0.0040 |

Group 2 gilts expressing estrus on Day 5 post-MATRIX® received 2 inseminations, Day 5 and Day 6. All other Group 2 gilts only received a single insemination on Day 6. All Group 3 gilts received an insemination on Day 5 and on Day 6, regardless of when estrus was expressed.

TABLE 17

Farrowing Rate Based on When Gilts Expressed Estrus

|  | Control | Group 2 | Group 3 | SEM | P < |
|---|---|---|---|---|---|
| Farrow (%) - Day 5 Estrus | 100 | 100 | 87.5 | 12.50 | 0.3916 |
| Farrow (%) - Day 6 Estrus | 95.0 | 76.0 | 82.6 | 5.08 | 0.0511 |
| Farrow (%) - Day 7 Estrus | 97.6 | 64.7 | 85.7 | 7.38 | 0.0026 |
| Farrow (%) - Day 8 Estrus | 57.1 | 0 | 20.0 | 20.10 | 0.2428 |
| Farrow (%) - Day 9 Estrus | 100 | — | — | — | — |
| Farrow (%) - No Estrus | 0 | 73.1 | 83.3 | 8.32 | 0.0093 |

Group 2 gilts expressing estrus on d 5 post-MATRIX® received 2 inseminations, Day 5 and Day 6. All other Group 2 gilts only received a single insemination on Day 6. All Group 3 gilts received an insemination on Day 5 and on Day 6, regardless of when estrus was expressed.

TABLE 18

Performance - Unadjusted Means

|  | Control | Group 2 | Group 3 |
|---|---|---|---|
| No. Gilts | 104 | 104 | 104 |
| Pregnant at 30 days, % | 91.3 | 76.9 | 82.7 |
| Percent Farrowed of Allotted | 90.1 | 72.8 | 80.8 |
| Piglets Born Live per Litter | 10.9 | 10.6 | 10.2 |
| Total Piglets Born per Litter | 12.1 | 11.5 | 11.3 |
| Piglet Index | 986 | 771 | 820 |

Includes only pregnancy and farrowing data for gilts bred within 8 days post-MATRIX®.

TABLE 19

Expression of Estrus post-MATRIX® - Unadjusted Means

|  | Control | Group 2 | Group 3 |
|---|---|---|---|
| No. Gilts | 104 | 104 | 104 |
| 1$^{st}$ Expression of Estrus on Day 5, % | 7.7 | 6.7 | 7.7 |
| 1$^{st}$ Expression of Estrus on Day 6, % | 40.4 | 48.1 | 44.2 |
| 1$^{st}$ Expression of Estrus on Day 7, % | 41.3 | 16.3 | 20.2 |
| 1$^{st}$ Expression of Estrus on Day 8, % | 6.7 | 1.9 | 4.8 |
| 1$^{st}$ Expression of Estrus on Day 9, % | 1.0 | — | — |
| Percent not expressing Estrus | 2.9 | 26.0 | 23.1 |

TABLE 20

Pregnancy Rate Based on When Gilts Expressed Estrus - Unadjusted Means

|  | Control | Group 2 | Group 3 |
|---|---|---|---|
| Pregnant (%) - Day 5 Estrus | 100 | 100 | 87.5 |
| Pregnant (%) - Day 6 Estrus | 95.2 | 84.0 | 82.6 |
| Pregnant (%) - Day 7 Estrus | 97.7 | 64.7 | 85.7 |
| Pregnant (%) - Day 8 Estrus | 71.4 | 0 | 40.0 |
| Pregnant (%) - Day 9 Estrus | 100 | — | — |
| Pregnant (%) - No Estrus | 0 | 74.1 | 87.5 |

Group 2 gilts expressing estrus on d 5 post-MATRIX® received 2 inseminations, Day 5 and Day 6.
All other Group 2 gilts only received a single insemination on Day 6.
All Group 3 gilts received an insemination on Day 5 and on Day 6, regardless of when estrus was expressed.

TABLE 21

Farrowing Rate Based on When Gilts Expressed Estrus - Unadjusted Means

|  | Control | Group 2 | Group 3 |
|---|---|---|---|
| Farrow (%) - Day 5 Estrus | 100 | 100 | 87.5 |
| Farrow (%) - Day 6 Estrus | 95.0 | 76.0 | 82.6 |
| Farrow (%) - Day 7 Estrus | 97.6 | 64.7 | 85.7 |

TABLE 21-continued

Farrowing Rate Based on When Gilts Expressed
Estrus - Unadjusted Means

|  | Control | Group 2 | Group 3 |
|---|---|---|---|
| Farrow (%) - Day 8 Estrus | 57.1 | 0 | 20.0 |
| Farrow (%) - Day 9 Estrus | 100 | — | — |
| Farrow (%) - No Estrus | 0 | 73.1 | 83.3 |

Group 2 gilts expressing estrus on d 5 post-MATRIX ® received 2 inseminations, Day 5 and Day 6.
All other Group 2 gilts only received a single insemination on Day 6.
All Group 3 gilts received an insemination on Day 5 and on Day 6, regardless of when estrus was expressed.

Example 4

Study Design and Treatments

Three hundred (300) gilts were fed MATRIX® as a top-dress for 14 days at the recommended rate of 15 mg/gilt/day. The last feeding of MATRIX® was at 7:00 AM (Day 0). One hundred gilts were allocated to each of the following treatments:
1. Group 1, Controls (n=100); MATRIX® treated, but not OvuGel™ treated, inseminated daily following detection of estrus, as is normally practiced at the site (average number of inseminations per gilt=1.9).
2. Group 2 (n=100); OvuGel™ treated at 8:00 am (+/−1 hr) on Day 5 and inseminated at 4 to 6 hours post-OvuGel™ treatment on Day 5, regardless of estrus status.
3. Group 3 (n=100); OvuGel™ treated at 8:00 am (+/−1 hr) on Day 5 and inseminated on Day 6, 25 hours (+/−1 hr) post-OvuGel™ treatment, without regard to estrus.

Test Substance

Triptorelin (pGlu-His-Trp-Ser-Tyr-D-Trp-Leu-Arg-Pro-Gly-$NH_2$) was supplied in the acetate form, from Bachem, Torrance, Calif. (Item H-4075 CGMP grade). Triptorelin gel (200 mcg/2 mL) was formulated by DPT Laboratories (San Antonio, Tex.) in a gel composed of Methocel Premium A4000 (Dow Chemical) and other inactive formulation excipients. Fifty-four milliliters of triptorelin gel (100 mcg triptorelin acetate/mL) was packaged in Amber Borosilicate Glass Serum Vials (610206-50) with a Gray Butyl Pharmaceutical Serum Vial Stopper (73828A-SS) with a Standard Aluminum Seal (SAS20NAT).

Estrus Observation

Gilts were housed in individual pens. Boars were housed at least 12 m away and downwind. To determine onset and duration of estrus, gilts were observed for estrus daily from 4 days until 8 days after last feeding of MATRIX® or until the end of estrus was confirmed, whichever came first. To facilitate detection of estrus, a mature boar was walked slowly in the alley in front of the gilt's pen, exposing each gilt to visual, auditory and olfactory signals from the boar for up to 5 minutes. While the boar was near the front of the gilt's pen, estrus was tested by an experienced person applying back pressure to the midsection of the gilt combined with side rubbing. Estrus was confirmed when a gilt stood rigidly to the back pressure, with no vocalization and with some indication of an ear reflex.

Drug Administration

A single 2 mL dose of OvuGel™ was deposited within approximately 1-2 cm posterior to the cervix with a catheter similar to those used for artificial insemination. The dose was delivered using a standard multi-dose applicator attached to the catheter. A new disposable sheath, which surrounds the catheter, was used for each gilt.

Statistical Analysis

Data were subjected to analysis of variance using the PROC MIX procedure of SAS (version 9.2) to determine the main effect of treatment, replicate and treatment by replicate interaction on farrowing rate and litter size. Differences between treatments were tested on least squares means estimates using the T test at $P<0.05$.

Results

Three hundred (300) gilts were allotted to treatment groups (Group 1: 100, Group 2: 100, Group 3: 100). Two Control gilts were removed from the study due to injuries and were removed from the final data set. Tables 22 through 25 present the least squares means and statistical analysis for all gilts. Raw data and unadjusted means are shown in Tables 26 through 29.

As shown in Table 22, the percentage of gilts, which expressed estrus by Day 8 post-MATRIX® was greater ($P<0.0001$) for the Control gilts (90.8%) compared to the gilts in Groups 2 (72.0%) and 3 (65.0%). OvuGel™ gilts (Groups 2 and 3) had a shorter ($P<0.01$) MATRIX® to estrus interval (5.9 d) compared to Control gilts (6.3 d). The percentage of gilts pregnant at 30 days post-insemination was the same for all treatments ($P>0.26$). The percentage of gilts that farrowed was not different ($P>0.16$) among treatments, nor was the piglet index ($P>0.18$), but the Control gilts did have a numerically higher farrowing rate and piglet index than did Groups 2 and 3 (76.5 vs. 67.0 and 64.6%, and 888 vs. 727 and 789, respectively). There was a trend ($P<0.09$) for Group 3 gilts to have more piglets born live per litter than the Control or Group 2 gilts. Total piglets born per litter was higher ($P<0.05$) for Group 3 gilts (13.5) than Control (12.8) or Group 2 gilts (11.9).

Table 23 presents the least squares means for the expression of estrus post-MATRIX®. There were more Group 2 gilts expressing estrus on Day 5 ($P<0.05$, 23.0%), but no difference due to treatment on Day 6 ($P>0.48$). On Day 7 post-MATRIX® there were fewer OvuGel™ gilts (Groups 2 and 3) expressing estrus for the first time compared to the Control gilts ($P<0.002$). Percentage of gilts not expressing estrus by Day 9 post-MATRIX® was greater ($P<0.0001$) for Groups 2 and 3 compared to the Controls (24.0%, 33.0%, 8.2%, respectively).

The pregnancy rate based on when gilts first expressed estrus is shown in Table 24. Regardless of treatment, gilts first expressing estrus on Days 5, 6, and 7 had similar pregnancy rates within each day ($P>0.73$).

Table 25 shows the farrowing rate of gilts based on when they first expressed estrus. As seen with the pregnancy data, those gilts expressing estrus on Days 5, 6, or 7, regardless of treatment, had similar farrowing rates within each day. Gilts in Groups 2 and 3 that did not express estrus had a farrowing rate of approximately 49%.

Results indicate that OvuGel™, given at ~120 hours after the last feeding of MATRIX®, and followed with either a single insemination on Day 5 or a single insemination on Day 6, have similar farrowing rates and litter sizes compared to gilts inseminated following detection of estrus.

TABLE 22

Gilt Performance

| | Control | Group 2 | Group 3 | SEM | P < |
|---|---|---|---|---|---|
| No. Gilts | 98 | 100 | 100 | — | — |
| Gilts Expressing Estrus by Day 8 post-MATRIX ®, % | 90.8 | 72.0 | 65.0 | 4.08 | 0.0001 |
| MATRIX ® to Estrus Interval, days | 6.3 | 5.9 | 5.9 | 0.13 | 0.0098 |
| Pregnant at 30 days, % | 76.5 | 67.0 | 67.7 | 4.58 | 0.2640 |
| Percent Farrowed of Allotted | 76.5 | 67.0 | 64.6 | 4.62 | 0.1608 |
| Piglets Born Live per Litter | 11.5 | 10.8 | 12.1 | 0.40 | 0.0844 |
| Total Piglets Born per Litter | 12.8 | 11.9 | 13.5 | 0.41 | 0.0422 |
| Piglet Index | 888 | 727 | 789 | 69.6 | 0.1818 |

Includes only pregnancy and farrowing data for gilts bred within 8 days post-MATRIX ®.

TABLE 23

Expression of Estrus post-MATRIX ®

| | Control | Group 2 | Group 3 | SEM | P < |
|---|---|---|---|---|---|
| No. Gilts | 98 | 100 | 100 | — | — |
| 1st Expression of Estrus on Day 4, % | 2.0 | 1.0 | 5.0 | 1.54 | 0.1937 |
| 1st Expression of Estrus on Day 5, % | 17.3 | 23.0 | 10.0 | 3.70 | 0.0482 |
| 1st Expression of Estrus on Day 6, % | 34.7 | 35.0 | 42.0 | 4.86 | 0.4841 |
| 1st Expression of Estrus on Day 7, % | 24.5 | 12.0 | 7.0 | 3.40 | 0.0016 |
| 1st Expression of Estrus on Day 8, % | 12.2 | 1.0 | 1.0 | 1.78 | 0.0001 |
| 1st Expression of Estrus on Day 9, % | 1.0 | 4.0 | 2.0 | 1.47 | 0.3699 |
| Percent not expressing Estrus | 8.2 | 24.0 | 33.0 | 3.93 | 0.0001 |

TABLE 24

Pregnancy Rate Based on When Gilts Expressed Estrus

| | Control | Group 2 | Group 3 | SEM | P < |
|---|---|---|---|---|---|
| Pregnant (%) - Day 4 Estrus | 100 | 100 | 25.0 | 25.00 | 0.1850 |
| Pregnant (%) - Day 5 Estrus | 70.6 | 78.3 | 70.0 | 11.82 | 0.8208 |
| Pregnant (%) - Day 6 Estrus | 85.3 | 80.0 | 85.7 | 6.16 | 0.7648 |
| Pregnant (%) - Day 7 Estrus | 83.3 | 75.0 | 71.4 | 13.09 | 0.7349 |
| Pregnant (%) - Day 8 Estrus | 100 | 0 | 0 | 0 | 0.0015 |
| Pregnant (%) - Day 9 Estrus | 100 | 0 | 0 | 0 | 0.0498 |
| Pregnant (%) - No Estrus | 0 | 45.8 | 54.5 | 9.60 | 0.0218 |

All Group 2 gilts received an insemination on Day 5, regardless of when estrus was expressed.
All Group 3 gilts received an insemination on Day 6, regardless of when estrus was expressed.

TABLE 25

Farrowing Rate Based on When Gilts Expressed Estrus

| | Control | Group 2 | Group 3 | SEM | P < |
|---|---|---|---|---|---|
| Farrow (%) - Day 4 Estrus | 100 | 100 | 25.0 | 25.00 | 0.1850 |
| Farrow (%) - Day 5 Estrus | 70.6 | 78.3 | 70.0 | 11.82 | 0.8208 |
| Farrow (%) - Day 6 Estrus | 85.3 | 80.0 | 81.0 | 6.39 | 0.8301 |
| Farrow (%) - Day 7 Estrus | 83.3 | 75.0 | 71.4 | 13.09 | 0.7349 |
| Farrow (%) - Day 8 Estrus | 100 | 0 | 0 | 0 | 0.0015 |
| Farrow (%) - Day 9 Estrus | 100 | 0 | 0 | 0 | 0.0498 |
| Farrow (%) - No Estrus | 0 | 45.8 | 51.5 | 9.61 | 0.0305 |

All Group 2 gilts received an insemination on Day 5, regardless of when estrus was expressed.
All Group 3 gilts received an insemination on Day 6, regardless of when estrus was expressed.

TABLE 26

Performance - Unadjusted Means

| | Control | Group 2 | Group 3 |
|---|---|---|---|
| No. Gilts | 98 | 100 | 100 |
| Gilts Expressing Estrus by Day 8 post-MATRIX ®, % | 90.8 | 72.0 | 65.0 |
| MATRIX ® to Estrus Interval, days | 6.3 | 5.9 | 5.9 |
| Pregnant at 30 days, % | 76.5 | 67.0 | 67.7 |
| Percent Farrowed of Allotted | 76.5 | 67.0 | 64.6 |
| Piglets Born Live per Litter | 11.5 | 10.8 | 12.1 |
| Total Piglets Born per Litter | 12.8 | 11.9 | 13.5 |
| Piglet Index | 883 | 722 | 785 |

TABLE 27

Expression of Estrus post-MATRIX ® - Unadjusted Means

| | Control | Group 2 | Group 3 |
|---|---|---|---|
| No. Gilts | 98 | 100 | 100 |
| 1st Expression of Estrus on Day 4, % | 2.0 | 1.0 | 5.0 |
| 1st Expression of Estrus on Day 5, % | 17.3 | 23.0 | 10.0 |
| 1st Expression of Estrus on Day 6, % | 34.7 | 35.0 | 42.0 |
| 1st Expression of Estrus on Day 7, % | 24.5 | 12.0 | 7.0 |
| 1st Expression of Estrus on Day 8, % | 12.2 | 1.0 | 1.0 |
| 1st Expression of Estrus on Day 9, % | 1.0 | 4.0 | 2.0 |
| Percent not expressing Estrus | 8.2 | 24.0 | 33.0 |

TABLE 28

Pregnancy Rate Based on When Gilts Expressed Estrus - Unadjusted Means

| | Control | Group 2 | Group 3 |
|---|---|---|---|
| Pregnant (%) - Day 4 Estrus | 100 | 100 | 25.0 |
| Pregnant (%) - Day 5 Estrus | 70.6 | 78.3 | 70.0 |
| Pregnant (%) - Day 6 Estrus | 85.3 | 80.0 | 85.7 |
| Pregnant (%) - Day 7 Estrus | 83.3 | 75.0 | 71.4 |
| Pregnant (%) - Day 8 Estrus | 100 | 0 | 0 |
| Pregnant (%) - Day 9 Estrus | 100 | 0 | 0 |
| Pregnant (%) - No Estrus | 0 | 45.8 | 54.5 |

All Group 2 gilts received an insemination on Day 5, regardless of when estrus was expressed.
All Group 3 gilts received an insemination on Day 6, regardless of when estrus was expressed.

TABLE 29

Farrowing Rate Based on When Gilts Expressed Estrus - Unadjusted Means

| | Control | Group 2 | Group 3 |
|---|---|---|---|
| Farrow (%) - Day 4 Estrus | 100 | 100 | 25.0 |
| Farrow (%) - Day 5 Estrus | 70.6 | 78.3 | 70.0 |

TABLE 29-continued

Farrowing Rate Based on When Gilts Expressed
Estrus - Unadjusted Means

|  | Control | Group 2 | Group 3 |
|---|---|---|---|
| Farrow (%) - Day 6 Estrus | 85.3 | 80.0 | 81.0 |
| Farrow (%) - Day 7 Estrus | 83.3 | 75.0 | 71.4 |
| Farrow (%) - Day 8 Estrus | 100 | 0 | 0 |
| Farrow (%) - Day 9 Estrus | 100 | 0 | 0 |
| Farrow (%) - No Estrus | 0 | 45.8 | 51.5 |

All Group 2 gilts received an insemination on Day 5, regardless of when estrus was expressed.
All Group 3 gilts received an insemination on Day 6, regardless of when estrus was expressed.

Example 5

Study Design and Treatments

All gilts were individually fed MATRIX® as a top-dress for 14 or 15 days at the recommended rate of 15 mg/gilt/day. Gilts were withdrawn from MATRIX® feeding (last top-dress in the morning on Day 0) and allocated to each of the following treatments. Controls were vehicle gel treated (vehicle gel without triptorelin) at 120 (+/−2) hours following MATRIX® withdrawal (last top dress). The other gilts were given 100, 200 or 400 mcg triptorelin as the acetate in a methylcellulose gel formulation 120 (+/−2) hours following MATRIX® withdrawal. The four treatments were:
1. Vehicle gel (VG): vehicle gel without triptorelin at 120 (+/−2) hours after MATRIX® withdrawal.
2. TG 100: 100 mcg (2 mL 50 mcg/mL) triptorelin gel at 120 (+/−2) hours after MATRIX® withdrawal.
3. TG 200: 200 mcg (2 mL 100 mcg/mL) triptorelin gel at 120 (+/−2) hours after MATRIX® withdrawal.
4. TG 400: 400 mcg (2 mL 200 mcg/mL) triptorelin gel at 120 (+/−2) hours after MATRIX® withdrawal.

Test Substance

Triptorelin (pGlu-His-Trp-Ser-Tyr-D-Trp-Leu-Arg-Pro-Gly-NH$_2$) was supplied in the acetate form, from Bachem, Torrance, Calif. (Item H-4075 CGMP grade). Triptorelin gel (100-400 mcg/2 mL dose) was formulated by Argenta (Auckland, NZ) in a gel composed of Methocel Premium A4000 (Dow Chemical), citrate buffer (pH 5.5), NaCl, methionine, and methyl and propyl parabens. Fifty-four milliliters of triptorelin gel (100 mcg triptorelin acetate/mL) was packaged in Amber Borosilicate Glass Serum Vials (610206-50) with a Gray Butyl Pharmaceutical Serum Vial Stopper (73828A-SS) with a Standard Aluminum Seal (SAS20NAT). The triptorelin gel vehicle contained the same formulation excipients as in triptorelin gel, except it did not contain triptorelin. MATRIX® was supplied as the US commercially available form.

Estrus Observation

For post-treatment estrus detection, gilts were housed in individual pens. Boars were housed in separate rooms, and/or at least 12 m away and downwind. To elicit signs of estrus, a mature boar was walked slowly in the alley in front of the gilts' crates, exposing each test gilt to visual, auditory and olfactory signals from the boar for up to 5 minutes. In keeping with standard practice at commercial farms, while the boar was near the front of the gilt's crate, estrus was tested by an experienced person applying back pressure to the midsection of the gilt combined with side rubbing. Estrus was confirmed when a gilt stood rigidly to the back pressure, with no vocalization and with some indication of an ear reflex. Gilts were not exposed to boars during the first three days after withdrawal of MATRIX® (Day 0 to Day 2). Estrus detection was performed daily on all gilts from Day 3 to Day 7.

Ovulation Monitoring

Ovulation was monitored twice on Day 5 (8 hours and 16 hours post-treatment) and every 8 hours on Day 6 and Day 7 or until ovulation was confirmed or 176 hours following last MATRIX® feeding. The ovulatory status of all gilts was monitored by transrectal ultrasonography. An Aloka 500 ultrasound machine is used for this purpose, with a 7.5 MHz linear array transducer attached to a fixed-angle PVC stabilizing rod to facilitate insertion into the rectum. The transducer and PVC rod are coated with a gynecological lubricant and gently inserted into the rectum until the ovaries can be visualized, one at a time. The diameters of the three largest follicles were recorded (to the nearest 0.1 mm) at each scanning. A gilt was declared to have ovulated when the number of large follicles (≥6.5 mm) fell to less than 3.

Blood Collection and LH Analysis

A catheter was inserted non-surgically into the jugular vein (Kraeling et al. 1982) of a subpopulation of gilts in each treatment group (vehicle gel, n=8; 100 mcg triptorelin, n=6; 200 mcg triptorelin, n=7 and 400 mcg triptorelin, n=6). Ten mL blood samples were collected every 15 minutes for one hour prior to treatment, immediately following treatment (0) and at 0.5, 1, 2, 4, 6, 12, 18, 24, 36 and 48 hours after treatment. Blood samples were maintained at 4° C. until centrifuged at 800×g for 15 minutes within 12 hours of collection. The resulting serum was stored frozen until assayed for LH using validated procedures for pig serum (Kesner et al., 1987 and Kraeling et al., 1982). Onset, duration, and magnitude of the LH surge were analyzed. The LH data were analyzed with the General Linear Models procedure of SAS. Differences between treatments were tested on least squares means estimates using the T test at P<0.05. Onset of the LH surge is when serum LH concentration is greater than or equal to two standard deviations of the mean of the pre-treatment serum LH concentrations. Duration of the LH surge is the period between onset and when serum LH concentration is again less than or equal to two standard deviations of the mean of the pre-treatment serum LH concentrations. Magnitude of the LH surge is the maximum serum LH concentration reached during the LH surge.

Administration

A single 2 mL dose of triptorelin gel or vehicle gel was deposited within approximately 1-2 cm posterior to the cervix with a catheter similar to those used for artificial insemination. The dose was delivered using a standard multi-dose applicator attached to the catheter. A new disposable sheath, which surrounds the catheter, was used for each gilt.

Results

Figure 4:
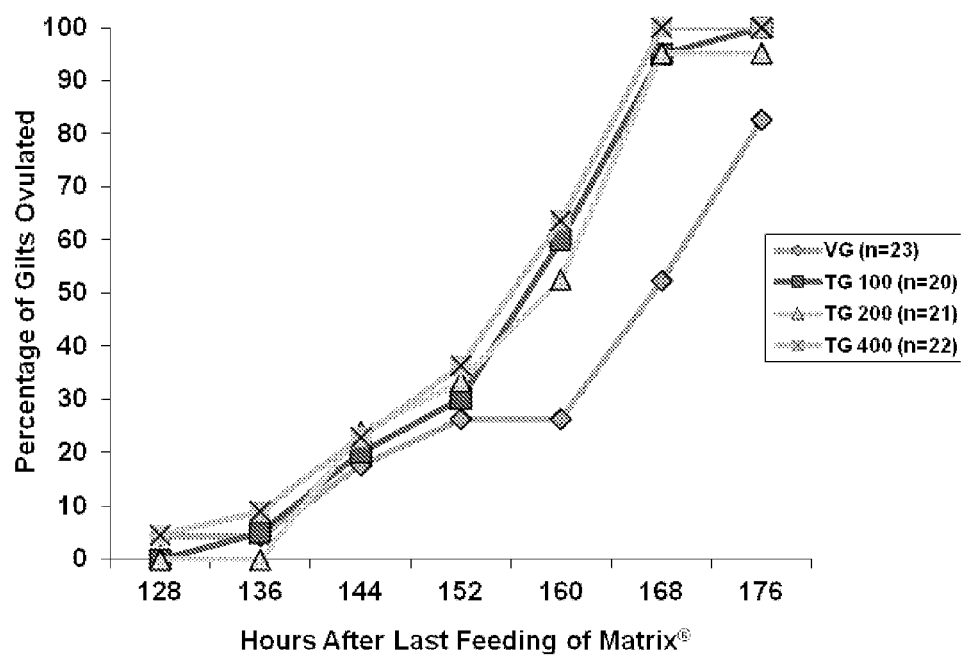
FIG. 4 shows the mean cumulative percentage of gilts, which ovulated after administration of vehicle or, triptorelin gel containing 100, 200, or 400 mcg triptorelin at 120 hours after last feeding of MATRIX®.

In this study, gilts were 171±7 days of age and 130±9 kg body weight at last MATRIX® feeding. The percentage of gilts which expressed estrus after the last feeding of MATRIX® (97%) and interval from last feeding of MATRIX® to estrus (146±22 hours) did not differ among treatments. Eight gilts were removed from the final data set for reasons not related to the treatment. No replicate by treatment interactions were detected for any parameters measured and therefore, data were combined for the two replicates. Results are presented in FIG. 4 and Tables 30-32.

Overall, 94% of gilts ovulated within the experimental period. More gilts ovulated (P<0.01) in the triptorelin gel (TG) treatment groups compared to vehicle gel (VG) by 48 hours post-treatment or by 168 hours following last MATRIX® feeding. The interval from last MATRIX® feeding until ovulation was not affected by treatment and averaged 160 hours or 6.7 days. There was no effect of treatment on the cumulative percentage of gilts, which ovulated by 128-152 hours after last feeding of MATRIX® (32 hours post-treatment). However, there was a significant effect of treatment on the cumulative percentage of gilts, which ovulated by 160-176 hours after last feeding of MATRIX® (40-56 hours post-treatment). A higher cumulative percentage of gilts ovulated by 168 hours (48 hours post-treatment) in the treated groups than in the vehicle gel group (Table 30). Time at which ovulation was detected and percentage of gilts, which ovulated at each ultrasound observation after treatment with triptorelin gel are presented in Table 30. There were no significant differences in mean hour that ovulation was detected after triptorelin gel treatment among any treatment group. The percentage of gilts which ovulated by 48 hours after triptorelin gel treatment was greater for gilts receiving triptorelin compared to the controls, but not different among triptorelin treatment groups (P>0.05).

Results demonstrate that triptorelin gel doses between 100-400 mcg triptorelin advanced ovulation compared to vehicle at 168 hours after last feeding of MATRIX®, suggesting that this dose range of triptorelin gel is effective for synchronizing ovulation after estrous cycle synchronization with MATRIX® in gilts.

In a previous study, we demonstrated that 100 mcg of triptorelin in triptorelin gel stimulated LH release in estrogen-primed ovariectomized gilts. The number of gilts, which displayed a LH surge, parameters of the LH surge, time that ovulation was detected and percentage of gilts, which ovulated by 48 hours after treatment with triptorelin gel containing 0, 100, 200 or 400 mcg of triptorelin acetate are presented in Table 31. There were no significant differences in mean onset of the LH surge, time to maximum serum LH concentration or magnitude of the LH surge among the treatment groups. However, duration of the LH surge was greater (P=0.04) for the 0 mcg group compared to the treated gilts. In general, these parameters of the LH surge were similar to those of our previous study in which intravaginal administration of triptorelin in triptorelin gel stimulated surge release of LH in estrogen-primed ovariectomized gilts. When the data from individual gilts were examined, it appeared that those gilts, which did not display a LH surge during the period of blood sampling, were either completing a LH surge at the time of triptorelin gel treatment or may have already had a LH surge before triptorelin gel treatment. Although the statistical analysis did not reveal significant differences among treatment groups for onset of the LH surge, time to maximum serum LH concentration or magnitude of the LH surge, all three means for these parameters suggest that the LH surge occurred earlier in the triptorelin treated gilts than in the 0 mcg control gilts. In addition, magnitude of the LH surge appeared to follow a dose response pattern. Similar to the data presented for all gilts in Table 30, the percentage of gilts, which ovulated by 48 hours after triptorelin gel treatment was greater for gilts receiving triptorelin than for controls.

Collectively, there was a beneficial effect of the triptorelin gel treatments on ovulation synchrony from last MATRIX® feeding. Results also demonstrate that triptorelin gel doses between 100-400 mcg triptorelin, administered at 120 hours after last feeding of MATRIX® advanced ovulation compared to vehicle at 168 hours after last feeding of MATRIX®, suggesting that this dose range of triptorelin gel is effective for synchronizing ovulation after estrous cycle synchronization with MATRIX® in gilts. The serum LH data are consistent with these conclusions.

TABLE 30

Least squares means for response variables measured for post-MATRIX ® gilts assigned to receive vehicle, 100, 200, or 400 mcg triptorelin as Triptorelin Gel (TG) at 120 hours after MATRIX ® withdrawal.

|  |  | Vehicle | 100 mcg TG | 200 mcg TG | 400 mcg TG | SEM | P |
|---|---|---|---|---|---|---|---|
| N |  | 23 | 20 | 21 | 22 |  |  |
| Estrous Expression (%) |  | 96.7 | 76.1 | 81.8 | 87.6 | 11.9 | 0.28 |
| Interval from MATRIX ® withdrawal to Estrus (h) |  | 143.2 | 136.7 | 138.9 | 137.1 | 3.8 | 0.55 |
| Interval from MATRIX ® Withdrawal to Ovulation |  | 164.5 | 160.4 | 160.0 | 158.5 | 2.6 | 0.41 |
| % of Sows Ovulating Post- |  |  |  |  |  |  |  |
| MATRIX ® | TG |  |  |  |  |  |  |
| 128 h | 8 h | 3.7 | 0 | 0 | 3.8 | 5.0 | 0.63 |
| 136 h | 16 h | 3.1 | 3.7 | 0 | 7.6 | 4.7 | 0.61 |
| 144 h | 24 h | 13.7 | 16.2 | 20.6 | 18.4 | 9.0 | 0.95 |
| 152 h | 32 h | 21.6 | 25.4 | 29.5 | 31.2 | 10.3 | 0.90 |
| 160 h | 40 h | 22.9$^x$ | 56.8$^y$ | 49.7$^{xy}$ | 60.0$^y$ | 10.7 | 0.0512 |
| 168 h | 48 h | 50.0$^x$ | 92.8$^y$ | 93.4$^y$ | 97.5$^y$ | 6.7 | 0.0001 |
| 176 h | 56 h | 82.1$^x$ | 99.5$^y$ | 94.8$^{xy}$ | 99.4$^y$ | 5.1 | 0.0417 |

Replicate is significant in Matrix to Estrus Interval, Matrix to OV Interval, MOV 144, and MOV152.

TABLE 31

Number of gilts displaying an LH surge, parameters of the LH surge, time (hours) at which ovulation was detected and percentage of gilts, which ovulated by 48 hours after treatment with triptorelin containing 0, 100, 200 or 400 mcg of triptorelin.

|  | Vehicle and Triptorelin (T) Treatments | | | |
| --- | --- | --- | --- | --- |
| Parameters relative to time of triptorelin gel treatment | Vehicle (n = 8) | 100 mcg T (n = 6) | 200 mcg T (n = 7) | 400 mcg T (n = 6) |
| Gilts, which displayed a LH surge | 6 | 4 | 1 | 5 |
| Onset of LH surge* | 11 ± 9 | 4 ± 3 | 0.5 | 4 ± 4 |
| Time of maximum LH conc.* | 20 ± 14 | 11 ± 7 | 4 | 12 ± 4 |
| Magnitude of LH surge* | 3.01 ± 1.62 | 3.94 ± 1.22 | 8.98 | 11.65 ± 12.35 |
| Duration of LH surge* | 30 ± 10 | 19 ± 2 | 18 | 17 ± 4 |
| Time at which ovulation detected* | 37 ± 19 | 40 ± 10 | 34 ± 9 | 40 ± 8 |
| Percentage ovulated by 48 hours | 63 | 100 | 100 | 100 |

*Least Squares Mean ± SE

TABLE 32

Raw averages for response variables measured for post-MATRIX ® gilts assigned to receive a vehicle (V), 100, 200, or 400 mcg triptorelin (T) at 120 hours after MATRIX ® withdrawal (includes rep 3 from PTK 1-07).

|  |  | PTK 2-07 | | | | PTK 1-07 (rep 3) | |
| --- | --- | --- | --- | --- | --- | --- | --- |
|  |  | Vehicle | 100 mcg T | 200 mcg T | 400 mcg T | Vehicle | 200 mcg T |
| N | | 23 | 20 | 21 | 22 | 8 | 10 |
| Estrous Expression (%) | | 95.7 | 75.0 | 81.0 | 86.4 | 87.5 | 100.0 |
| Interval from MATRIX ® withdrawal to Estrus (h) | | 140.7 | 134.4 | 136.9 | 133.9 | 140.6 | 129.6 |
| Interval from MATRIX ® Withdrawal to Ovulation | | 163.4 | 159.2 | 158.8 | 157.1 | 164.6 | 153.6 |
| % of Sows Ovulating Post- | | | | | | | |
| MATRIX ® | V or T | | | | | | |
| 128 h | 8 h | 4.3 | 0.0 | 0.0 | 4.5 | 0.0 | 0.0 |
| 136 h | 16 h | 4.3 | 5.0 | 0.0 | 9.1 | 0.0 | 10.0 |
| 144 h | 24 h | 17.4 | 20.0 | 23.8 | 22.7 | 0.0 | 30.0 |
| 152 h | 32 h | 26.1 | 30.0 | 33.3 | 36.4 | 25.0 | 70.0 |
| 160 h | 40 h | 26.1 | 60.0 | 52.4 | 63.6 | 25.0 | 80.0 |
| 168 h | 48 h | 52.2 | 95.0 | 95.2 | 100.0 | 75.0 | 90.0 |
| 176 h | 56 h | 82.6 | 100.0 | 95.2 | 100.0 | 87.5 | 100.0 |

Example 6

Preparation of Triptorelin-Containing Composition

Methylparaben sodium salt and propylparaben sodium salt were added to purified water with mixing and mixing continued for 5-10 minutes. Sodium chloride USP was then added with mixing for another 10-15 minutes followed by the addition of L-methionine with mixing for 10-15 minutes. Sodium citrate USP was then also added with mixing for another 10-20 minutes.

In a separate mixer, citric acid was added to purified water and was mixed 5-10 minutes before the addition of triptorelin acetate, and mixing then continued for 10-20 minutes. The paraben-containing composition was then added to the triptorelin-containing composition and mixed for 10-15 minutes. Methylcellulose was then slowly added to avoid clumping and mixing continued for another 30-60 minutes.

The pH of the mixture was then checked and citric acid in purified water was added as necessary to adjust the pH of the composition.

Example 7

Example Formulations

Example formulations for the composition described in this application are shown in Tables 33 and 34.

TABLE 33

| Ingredient | Function | Weight (% w/v) |
| --- | --- | --- |
| Methylparaben, sodium salt (USNF) | Anti-microbial preservative | 0.0900 |
| Propylparaben, sodium salt (USNF) | Anti-microbial preservative | 0.0100 |
| Sodium chloride, laboratory reagent | Tonicity agent | 0.910 |

TABLE 33-continued

| Ingredient | Function | Weight (% w/v) |
|---|---|---|
| Sodium citrate, dihydrate | Buffering agent | 0.186 |
| L-Methionine, laboratory reagent | Stabilizing agent | 0.100 |
| Citric acid, anhydrous | Buffer | 0.0700 |
| Triptorelin acetate | Active Pharmaceutical Ingredient (API) | 0.0100 |
| Water (USNF) | Dissolving solvent | 98.4 |
| Methylcellulose (A4M Premium) (USP) | Thickening agent | 1.20 |

TABLE 34

| Component | Quality Standard | Function | Amount per 100 mg % w/w |
|---|---|---|---|
| Triptorelin Acetate | In house | Drug Substance | 11.0 mg 0.011%* |

TABLE 34-continued

| Component | Quality Standard | Function | Amount per 100 mg % w/w |
|---|---|---|---|
| Purified Water | USP | Solvent | 97.6 g 97.54%* |
| Methylparaben, Sodium Salt** | NF | Preservative | 89.0 mg 0.089%* |
| Propylparaben, Sodium Salt** | NF | Preservative | 10.0 mg 0.010* |
| Sodium Chloride | USP | Tonicity agent | 901 mg 0.901% |
| L-Methionine | USP | Stabilizing agent | 99.0 mg 0.099% |
| Sodium Citrate | USP | Buffering agent | 184 mg 0.184% |
| Citric Acid | USP | Buffering agent | 69.0 mg 0.069%* |
| Methycellulose | USP | Viscosity modifier | 1.1 g 1.10%* |

*Nominal amount
**Tested to compendial standard

What is claimed is:

1. A method for synchronizing time of ovulation in a gilt, the method comprising the steps of:
    administering to the gilt a hormone for synchronizing estrus;
    administering to the gilt a single dose of a gonadotropin-releasing hormone for synchronizing ovulation, without administration of any other hormone for synchronizing ovulation, wherein the gonadotropin-releasing hormone is administered on the fifth day after the last daily administration of the hormone for synchronizing estrus; and
    inseminating the gilt, without monitoring estrus, only one time on the sixth day after the last daily administration of the hormone for synchronizing estrus
    wherein the last daily administration to the gilt of the hormone for synchronizing estrus is day 0.

2. The method of claim 1 wherein the gonadotropin releasing hormone has the formula

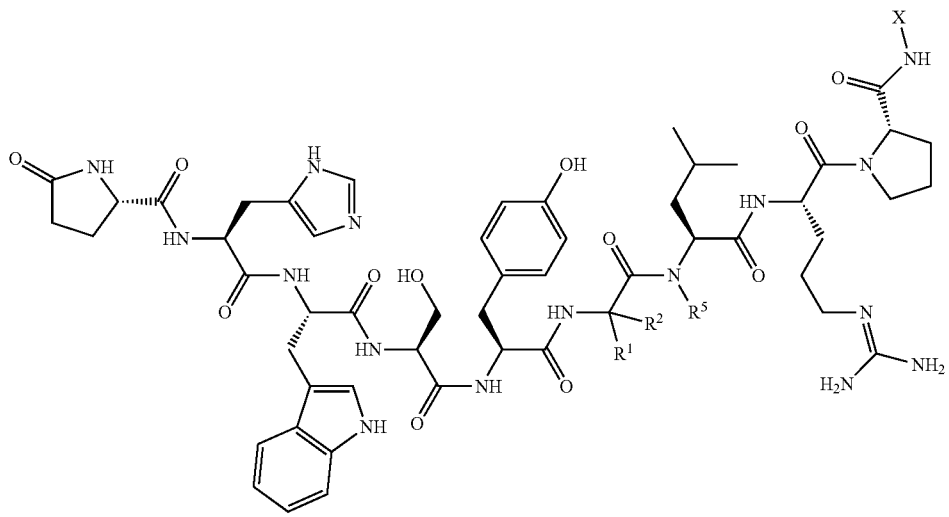

or a solvate, a hydrate, or a pharmaceutically acceptable salt thereof wherein
$R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
$R^5$ is hydrogen or alkyl; and
X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

3. The method of claim 2 wherein the gonadotropin-releasing hormone is selected from the group consisting of compounds of the formula of claim 2 wherein
a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
b) $R^1$ is hydrogen, $R^2$ is hydrogen, X is $CH_2(CO)NH_2$; and $R^5$ is hydrogen;

c) R¹ is 1H-1-benzyl-imidazol-4-yl-methyl, R² is hydrogen, X is ethyl; and R⁵ is hydrogen;
d) R¹ is 2-methylpropyl, R² is hydrogen, X is ethyl; and R⁵ is hydrogen;
e) R¹ is 2-naphthlymethyl, R² is hydrogen, X is CH₂(CO)NH₂; and R⁵ is hydrogen;
f) R¹ is t-butoxymethyl, R² is hydrogen, X is ethyl; R⁵ is hydrogen; and the configuration of the carbon to which R¹ is attached is R;
g) R¹ is benzyl, R² is hydrogen, X is CH₂(CO)NH₂; R⁵ is hydrogen; and the configuration of the carbon to which R¹ is attached is R;
h) R¹ is t-butoxymethyl, R² is hydrogen, X is HN(CO)NH₂; and R⁵ is hydrogen;
i) R¹ is 1H-indol-3-yl-methyl, R² is hydrogen, X is ethyl; and R⁵ is hydrogen;
j) R¹ is methyl, R² is hydrogen, X is hydrogen; R⁵ is hydrogen; and the configuration of the carbon to which R¹ is attached is R;
k) R¹ is 1H-indol-3-yl-methyl, R² is hydrogen, X is ethyl; R⁵ is methyl; and the configuration of the carbon to which R¹ is attached is R;
l) R¹ is methyl, R² is hydrogen, X is CH₂(CO)NH₂; R⁵ is hydrogen; and the configuration of the carbon to which R¹ is attached is R;
m) R¹ is 4-aminobutyl, R² is hydrogen, X is HN(CO)NH₂; R⁵ is hydrogen; and the configuration of the carbon to which R¹ is attached is R;
n) R¹ is methyl, R² is methyl, X is HN(CO)NH₂; and R⁵ is hydrogen; and
o) R¹ is ethyl, R² is hydrogen, X is hydrogen; R⁵ is hydrogen; and the configuration of the carbon to which R¹ is attached is R.

4. The method of claim 1 wherein the insemination is an artificial insemination.

5. The method of claim 1 wherein the gonadotropin-releasing hormone is administered in an effective amount and the effective amount of the gonadotropin-releasing hormone is about 200 µg.

6. The method of claim 1 wherein the dose of the gonadotropin-releasing hormone is administered using a method selected from the group consisting of use of a deposition catheter, manual administration, and injection.

7. The method of claim 6 wherein the gonadotropin-releasing hormone is administered using a deposition catheter.

8. The method of claim 6 wherein the gonadotropin-releasing hormone is administered by injection.

9. The method of claim 2 wherein in the formula X is H₂CC(O)NH₂, R₁ is hydrogen, and R₂ is

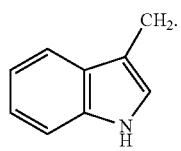

10. The method of claim 1 wherein the gonadotropin-releasing hormone is triptorelin.

11. The method of claim 10 wherein the hormone that synchronizes estrus is altrenogest.

12. The method of claim 1 wherein the gonadotropin-releasing hormone is in a composition and the composition comprises methylparaben in an amount of about 0.09% weight per volume, propylparaben in an amount of about 0.01% weight per volume, sodium chloride in an amount of about 0.91% weight per volume, sodium citrate in an amount of about 0.186% weight per volume, L-methionine in an amount of about 0.1% weight per volume, citric acid in an amount of about 0.07% weight per volume, triptorelin in an amount of about 0.01% weight per volume, and methycellulose in an amount that provides a viscosity of about 250 cP to about 400 cP.

13. The method of claim 1 wherein the gonadotropin-releasing hormone is in an excipient selected from the group consisting of buffered saline, a liquid alcohol, a glycol, a glucose solution, an ester, an amide, and sterile water.

14. The method of claim 13 wherein the excipient further comprises a pH buffering agent selected from the group consisting of an acetate buffer, a borate buffer, a carbonate buffer, a citrate buffer, a phosphate buffer, hydrochloric acid, sodium hydroxide, magnesium oxide, monopotassium phosphate, bicarbonate, ammonia, carbonic acid, sodium citrate, citric acid, acetic acid, and disodium hydrogen phosphate.

15. The method of claim 1 wherein the gonadotropin-releasing hormone is administered about 125 to about 133 hours after the last daily administration of the hormone for synchronizing estrus.

16. The method of claim 1 wherein the gonadotropin-releasing hormone is administered about 126 to about 130 hours after the last daily administration of the hormone for synchronizing estrus.

17. The method of claim 1 wherein the gonadotropin-releasing hormone is administered about 126 hours after the last daily administration of the hormone for synchronizing estrus.

18. The method of claim 1 wherein the gonadotropin-releasing hormone is administered about 128 hours after the last daily administration of the hormone for synchronizing estrus.

19. The method of claim 1 wherein the gonadotropin-releasing hormone is administered about 130 hours after the last daily administration of the hormone for synchronizing estrus.

20. The method of claim 1 wherein the gonadotropin-releasing hormone is administered about 132 hours after the last daily administration of the hormone for synchronizing estrus.

21. The method of claim 1 wherein the gilt is inseminated about 24 to about 28 hours after administration of the gonadotropin-releasing hormone.

22. The method of claim 1 wherein the gilt is inseminated about 20 to about 24 hours after administration of the gonadotropin-releasing hormone.

* * * * *